US012570738B2

(12) United States Patent
Khan et al.

(10) Patent No.: US 12,570,738 B2
(45) Date of Patent: Mar. 10, 2026

(54) MULTI-SPECIFIC ANTIBODY WITH BINDING SPECIFICITY FOR HUMAN IL-13 AND IL-17

(71) Applicant: UCB BIOPHARMA SRL, Brussels (BE)

(72) Inventors: Adnan Rahman Khan, Slough (GB); Sam Philip Heywood, Slough (GB); David Paul Humphreys, Slough (GB); Daniel John Lightwood, Slough (GB); Emma Dave, Slough (GB); Emily Mary Cairistine Barry, Slough (GB); Sarah Jayne Stanyon, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 893 days.

(21) Appl. No.: 17/786,996

(22) PCT Filed: Dec. 18, 2020

(86) PCT No.: PCT/EP2020/087046
§ 371 (c)(1),
(2) Date: Jun. 17, 2022

(87) PCT Pub. No.: WO2021/123186
PCT Pub. Date: Jun. 24, 2021

(65) Prior Publication Data
US 2023/0087378 A1 Mar. 23, 2023

(30) Foreign Application Priority Data
Dec. 20, 2019 (GB) ...................................... 1919061

(51) Int. Cl.
*C07K 16/24* (2006.01)
*A61K 39/00* (2006.01)
*A61P 37/08* (2006.01)

(52) U.S. Cl.
CPC ............ *C07K 16/244* (2013.01); *A61P 37/08* (2018.01); *A61K 2039/505* (2013.01); *C07K 2317/31* (2013.01); *C07K 2317/565* (2013.01); *C07K 2317/622* (2013.01)

(58) Field of Classification Search
None
See application file for complete search history.

(56) References Cited

U.S. PATENT DOCUMENTS

| | | |
|---|---|---|
| 4,741,900 A | 5/1988 | Alvarez et al. |
| 5,219,996 A | 6/1993 | Bodmer et al. |
| 5,223,409 A | 6/1993 | Ladner et al. |
| 5,403,484 A | 4/1995 | Ladner et al. |
| 5,427,908 A | 6/1995 | Dower et al. |
| 5,516,637 A | 5/1996 | Huang et al. |
| 5,545,806 A | 8/1996 | Lonberg et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,667,425 A | 9/1997 | Pineau et al. |
| 5,698,426 A | 12/1997 | Huse |
| 5,733,743 A | 3/1998 | Johnson et al. |
| 5,750,753 A | 5/1998 | Kimae et al. |
| 5,770,429 A | 6/1998 | Lonberg et al. |
| 5,780,225 A | 7/1998 | Wigler et al. |
| 5,821,047 A | 10/1998 | Garrard et al. |
| 5,969,108 A | 10/1999 | Mccafferty et al. |
| 6,267,964 B1 | 7/2001 | Nygren et al. |

FOREIGN PATENT DOCUMENTS

| | | |
|---|---|---|
| EP | 0392745 A2 | 10/1990 |
| EP | 0438474 A1 | 7/1991 |
| EP | 0463151 A1 | 1/1992 |
| EP | 0486525 A1 | 5/1992 |
| EP | 0546073 B1 | 9/1997 |
| EP | 0948544 A1 | 10/1999 |
| EP | 1090037 A1 | 4/2001 |
| WO | 86/01533 A1 | 3/1986 |
| WO | 89/00195 A1 | 1/1989 |
| WO | 89/01476 A1 | 2/1989 |
| WO | 90/02809 A1 | 3/1990 |
| WO | 91/01743 A1 | 2/1991 |
| WO | 91/09967 A1 | 7/1991 |
| WO | 91/10737 A1 | 7/1991 |
| WO | 92/01047 A1 | 1/1992 |

(Continued)

OTHER PUBLICATIONS

Johns Hopkins. Eczema and Atopic Dermatitis. website saved May 7, 2025. (Year: 2025).*
USZ. Eosinophilic Esophagitis (EoE). website saved May 7, 2025. (Year: 2025).*
Cleveland Clinic. Food Allergies Management and Treatment. website saved May 7, 2025. (Year: 2025).*
Penn Medicine. Nasal Polyps. website saved May 7, 2025. (Year: 2025).*
NCI Dictionary. Polyposis Definition. saved May 7, 2025. (Year: 2025).*
Merriam-Webster Dictionary. Prevent Definition. saved Apr. 24, 2025. (Year: 2025).*
Yang et al., Clinical Review: Pruritus in allergy and immunology, J. Allergy Clin. Immunol., 144(2):353-360 (2019).

(Continued)

*Primary Examiner* — Julie Wu
*Assistant Examiner* — Amy M. Chattin
(74) *Attorney, Agent, or Firm* — MARSHALL, GERSTEIN & BORUN LLP

(57) ABSTRACT

The present invention relates to a multi-specific antibody having specificity for human IL-13, human IL-17A and/or human IL-17F. The invention further relates to methods for producing the multi-specific antibody and to its therapeutic use for the treatment of atopic dermatitis and other diseases.

28 Claims, 19 Drawing Sheets

Specification includes a Sequence Listing.

(56) References Cited

FOREIGN PATENT DOCUMENTS

| WO | 92/02551 | A1 | 2/1992 | | |
|----|----------|----|--------|--|--|
| WO | 92/18619 | A1 | 10/1992 | | |
| WO | 92/22583 | A2 | 12/1992 | | |
| WO | 93/06231 | A1 | 4/1993 | | |
| WO | 93/11236 | A1 | 6/1993 | | |
| WO | 95/15982 | A2 | 6/1995 | | |
| WO | 95/20401 | A1 | 8/1995 | | |
| WO | 96/27011 | A1 | 9/1996 | | |
| WO | 97/34631 | A1 | 9/1997 | | |
| WO | 98/25791 | A1 | 6/1998 | | |
| WO | 98/37200 | A2 | 8/1998 | | |
| WO | 98/50431 | A2 | 11/1998 | | |
| WO | 99/37791 | A1 | 7/1999 | | |
| WO | 99/64460 | A1 | 12/1999 | | |
| WO | 01/45746 | A2 | 6/2001 | | |
| WO | 02/76489 | A1 | 10/2002 | | |
| WO | 03/31581 | A2 | 4/2003 | | |
| WO | 2004/001064 | A2 | 12/2003 | | |
| WO | 2004/003019 | A2 | 1/2004 | | |
| WO | 2004/051268 | A1 | 6/2004 | | |
| WO | 2004/106377 | A1 | 12/2004 | | |
| WO | 2005/003169 | A2 | 1/2005 | | |
| WO | 2005/003170 | A2 | 1/2005 | | |
| WO | 2005/003171 | A2 | 1/2005 | | |
| WO | 2005/117984 | A2 | 12/2005 | | |
| WO | 2005/118642 | A2 | 12/2005 | | |
| WO | 2006/059106 | A2 | 6/2006 | | |
| WO | 2007/109254 | A2 | 9/2007 | | |
| WO | 2008/096158 | A2 | 8/2008 | | |
| WO | 2009/040562 | A1 | 4/2009 | | |
| WO | 2010/035012 | A1 | 4/2010 | | |
| WO | 2011/006915 | A2 | 1/2011 | | |
| WO | 2011/030107 | A1 | 3/2011 | | |
| WO | 2011/061246 | A2 | 5/2011 | | |
| WO | 2011/061492 | A2 | 5/2011 | | |
| WO | 2011/086091 | A1 | 7/2011 | | |
| WO | 2011/117648 | A2 | 9/2011 | | |
| WO | 2011/131746 | A2 | 10/2011 | | |
| WO | 2012/058768 | A1 | 5/2012 | | |
| WO | 2012/095662 | A1 | 7/2012 | | |
| WO | 2013/068571 | A1 | 5/2013 | | |
| WO | 2013/102042 | A2 | 7/2013 | | |
| WO | 2015/127405 | A2 | 8/2015 | | |
| WO | 2015/197772 | A1 | 12/2015 | | |
| WO | 2015/197789 | A1 | 12/2015 | | |
| WO | 2016/073791 | A1 | 5/2016 | | |
| WO | WO-2019220109 | A1 * | 11/2019 | ....... | C07K 14/70521 |
| WO | WO-2020010250 | A2 * | 1/2020 | ............. | A61P 35/00 |
| WO | WO-2021/123190 | A1 | 6/2021 | | |

OTHER PUBLICATIONS

Young et al., Thermal stabilization of a single-chain Fv antibody fragment by introduction of a disulphide bond, FEBS Lett., 377(2):135-9 (1995).

Zhang et al., PowerBLAST: a new network BLAST application for interactive or automated sequence analysis and annotation, Genome Res., 7:649-656 (1997).

Zhu et al., Remodeling domain interfaces to enhance heterodimer formation, Protein Sci., 6(4):781-8 (1997).

Altschul et al., Basic local alignment search tool, J. Mol. Biol., 215(3):403-410 (1990).

Altschul et al., Gapped BLAST and PSI-BLAST: a new generation of protein database search programs, Nucleic Acids Research, 25:3389-3402 (1997).

Ames et al., Conversion of murine fabs isolated from a combinatorial phage display library to full length immunoglobulins, J. Immunol. Methods, 184(2):177-186 (1995).

Angal et al., A single amino acid substitution abolishes the heterogeneity of chimeric mouse/human (IgG4) antibody, Mol. Immunol., 30(1):105-8 (1993).

Babcook et al., A novel strategy for generating monoclonal antibodies from single, isolated lymphocytes producing antibodies of defined specificities, Proc. Natl. Acad. Sci. USA., 93:7843-78481 (1996).

Brinkman et al., Phage display of disulfide-stabilized Fv fragments, J. Immunol. Methods, 182(1):41-50 (1995).

Brinkman et al., The making of bispecific antibodies, mAbs, 9(2):182-212 (2017).

Brinkmann et al., A recombinant immunotoxin containing a disulfide-stabilized Fv fragment, Proc. Natl. Acad. Sci. USA, 90(16):7538-7542 (1993).

Burton et al., Human antibodies from combinatorial libraries, Adv. in Immun., 57:191-280 (1994).

Chapman, PEGylated antibodies and antibody fragments for improved therapy: a review, Advanced Drug Delivery Reviews, 54:531-545, (2002).

Chothia et al., Canonical Structures for the Hypervariable Regions of Immunoglobulins, Journal of Molecular Biology, 196(4):901-917 (1987).

Coloma et al., Design and production of novel tetravalent bispecific antibodies, Nat. Biotechnol., 15:159-63 (1997).

Dondelinger et al., Understanding the Significance and Implications of Antibody Numbering and Antigen-Binding Surface/Residue Definition, Frontiers in Immunology, 9:2278 (2018).

Dubowchik et al., Receptor-mediated and enzyme-dependent targeting of cytotoxic anticancer drugs, Pharm. Therapeutics, 83:67-123 (1999).

GB Patent Application No. 1919061.0, Search Report, mailed Jun. 16, 2020.

Gish et al., Identification of protein coding regions by database similarity search, Nat. Genet., 3:266-272 (1993).

Glockshuber et al., A comparison of strategies to stabilize immunoglobulin Fv-fragments, Biochem., 29:1362-1367 (1990).

Godar et al., Therapeutic bispecific antibody formats: a patent applications review (1994-2017), Exp. Opin. on Therap. Paten., 28(3):251-276 (2018).

Graille et al., Crystal structure of a *Staphylococcus aureus* protein A domain complexed with the Fab fragment of a human IgM antibody: Structural basis for recognition of B-cell receptors and superantigen activity, PNAS, 97(10):5399-404 (2000).

Griffin et al., Computer Analysis of Sequence Data, Computer Analysis of Sequence Data, Part 1, Humana Press, New Jersey (1994).

Hellstrom et al., Antibodies for Drug Delivery, Controlled Drug Delivery, 2nd ed, Marcel Dekker, Inc, 623-653 (1987).

Holt et al., Anti-serum albumin domain antibodies for extending the half-lives of short lived drugs, Protein Engineering, Design & Selection, 21(5):283-288 (2008).

International Application No. PCT/EP2020/087046, International Preliminary Report on Patentability, mailed Jun. 30, 2022.

International Application No. PCT/EP2020/087046, International Search Report and Written Opinion, mailed Mar. 18, 2021.

Jung et al., Design of Interchain Disulfide Bonds in the Framework Region of the Fv Fragment of the Monoclonal Antibody B3, Proteins, 19(1):35-47 (1994).

Junghans et al., Anti-Tac-H, a Humanized Antibody to the Interleukin2 Receptor with New Features for Immunotherapy in Malignant and Immune Disorders, Cancer Res., 50:1495-1502 (1990).

Kashmiri et al., SDR grafting—a new approach to antibody humanization, Methods, 36:25-34 (2005).

Kettleborough et al., Isolation of tumor cell-specific single-chain Fv from immunized mice using phage-antibody libraries and the reconstruction of whole antibodies from these antibody fragments, Eur. J. Immunol., 24:952-958 (1994).

Klein et al., Engineering therapeutic bispecific antibodies using CrossMab technology, Method., 154:21-31 (2019).

Kozbor et al., The production of monoclonal antibodies from human lymphocytes, Immunol. Today, 4:72-79 (1983).

Lee et al., BiP and immunoglobulin light chain cooperate to control the folding of heavy chain and ensure the fidelity of immunoglobulin assembly, Molecular biology of the cell, 10(7):2209-19 (1999).

(56)         References Cited

OTHER PUBLICATIONS

Luo et al., VI-linker-Vh orientation-dependent expression of single chain Fv-containing an engineered disulfide-stabilized bond in the framework regions, J. Biochem., 118:825-831 (1995).

Madden et al., Applications of network BLAST server, Meth. Enzymol., 266:131-41 (1996).

Medesan et al., Delineation of the amino acid residues involved in transcytosis and catabolism of mouse IgG1, J. Immunol., 158(5):2211-2217 (1997).

Milstein et al., Continuous cultures of fused cells secreting antibody of predefined specificity, Nature, 256:495-497 (1975).

Persic et al., An integrated vector system for the eukaryotic expression of antibodies or their fragments after selection from phage display libraries, Genes, 187:9-18 (1997).

Peters et al., Serum albumin, Adv. Protein Chem, 37:161-245 (1985).

Pierre et al., Antibodies to cell surface proteins redirect intracellular trafficking pathways, Exp. Mol. Pathol., 91(3):723-732 (2011).

Roben et al., VH3 family antibodies bind domain D of staphylococcal protein A, Journal of Immunology, 154(12):6437-45 (1995).

Schellekens et al., Immunogenicity of Therapeutic Proteins: Clinical Implications and Future Prospects, Clin. Ther., 24(11): 1720-40 (2002).

Schoonjans et al., Fab chains as an efficient heterodimerization scaffold for the production of recombinant bispecific and trispecific antibody derivatives, The Journal of Immunology, 165(12):7050-7057 (2000).

Smith et al., Prolonged in Vivo residence times of antibody fragments associated with Albumin, Bioconjug. Chem., 12(5):750-756 (2001).

Spiess et al., Alternative molecular formats and therapeutic applications for bispecific antibodies, Molecular Immunology, 67:95-106 (2015).

Staton et al., A phase I, randomized, observer-blinded, single and multiple ascending-dose study to investigate the safety, pharmacokinetics, and immunogenicity of BITS7201A, a bispecific antibody targeting IL-13 and IL-17, in healthy volunteers, BMC Pulmonary Medicine., 19(5):1-16 (2019).

Thorpe et al., The preparation and cytotoxic properties of antibody-toxin conjugates, Immunol. Ref., 62:119-58 (1982).

Tilegenova et al., Dissecting the molecular basis of high viscosity of monospecific and bispecific IgG antibodies, MABS., 12(1):e1692764 (2020).

Verma et al., Antibody engineering: comparison of bacterial, yeast, insect and mammalian expression systems, Journal of Immunological Methods, 216(1-2):165-181 (1998).

Waldemann et al., Metabolism of immunoglobulins, Prog Allergy, 13:1-110 (1969).

Weatherill et al., Towards a universal disulphide stabilised single chain Fv format: importance of interchain disulphide bond location and vL-vH orientation, Protein Engineering, Design & Selection, 25(7):321-329 (2012).

Wells et al., Cassette mutagenesis: an efficient method for generation of multiple mutations at defined sites, Gene., 34(2-3):315-23 (1985).

* cited by examiner

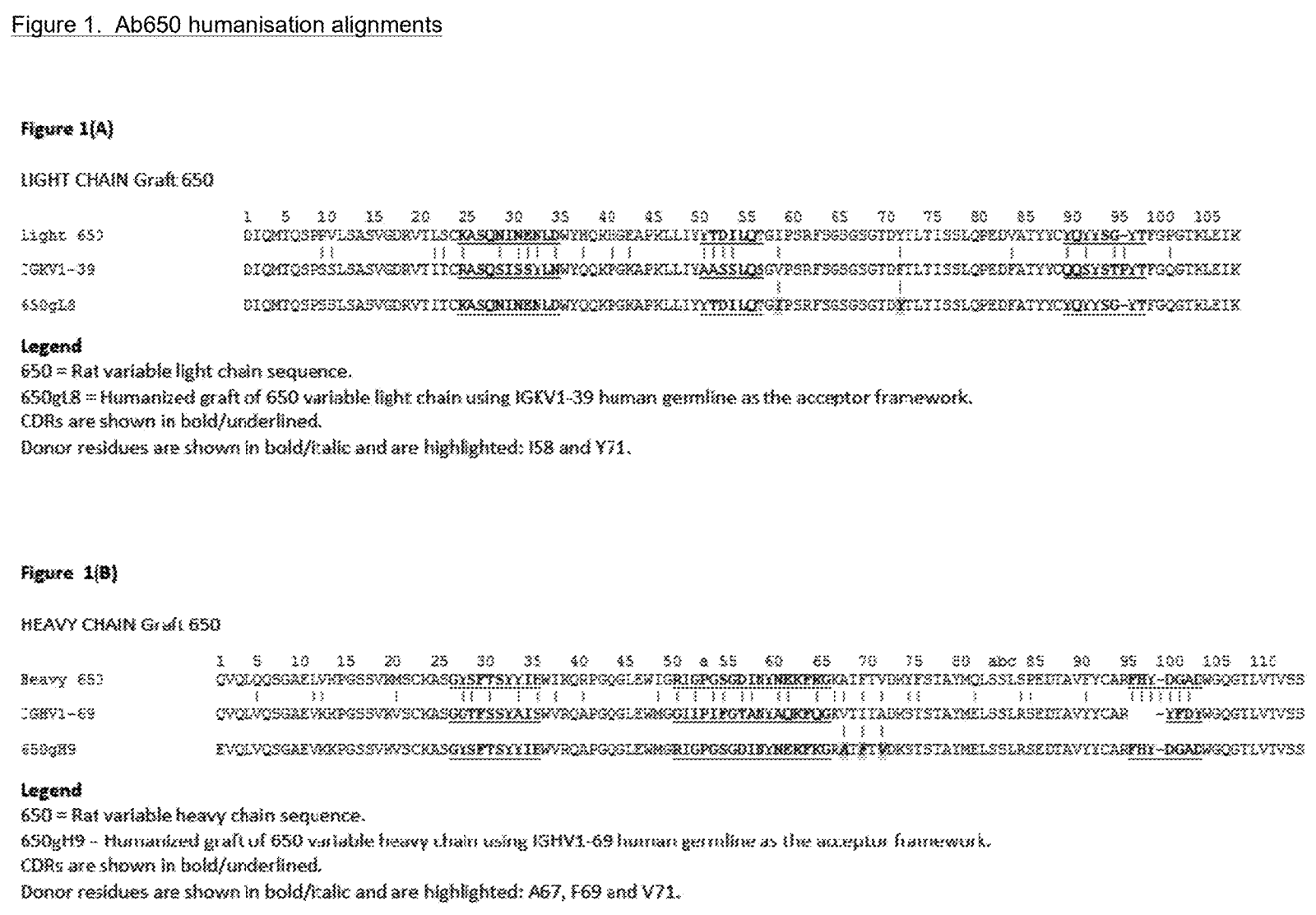

Figure 1. Ab650 humanisation alignments

Figure 1(A)

LIGHT CHAIN Graft 650

Light 650
IGKV1-39
650gL8

Legend

650 = Rat variable light chain sequence.

650gL8 = Humanised graft of 650 variable light chain using IGKV1-39 human germline as the acceptor framework.

CDRs are shown in bold/underlined.

Donor residues are shown in bold/italic and are highlighted: I58 and Y71.

Figure 1(B)

HEAVY CHAIN Graft 650

Heavy 650
IGHV1-69
650gH9

Legend

650 = Rat variable heavy chain sequence.

650gH9 = Humanised graft of 650 variable heavy chain using IGHV1-69 human germline as the acceptor framework.

CDRs are shown in bold/underlined.

Donor residues are shown in bold/italic and are highlighted: A67, F69 and V71.

Figure 2: Amino acid and DNA sequences

Anti-IL-17A/F

CDR sequences Ab 496.g3

SEQ ID NO:1  CDRL1 of 496.g3

RADESVRTLMH

SEQ ID NO:2  CDRL2 of 496.g3

LVSNSEI

SEQ ID NO:3  CDRL3 of 496.g3

QQTWSDPWT

SEQ ID NO:4  CDRH1 of 496.g3

GFTFSDYNMA

SEQ ID NO:5  CDRH2 of 496.g3

TITYEGRNTYYRDSVKG

SEQ ID NO:6  CDRH3 of 496.g3

PPQYYEGSIYRLWFAH

SEQ ID NO:7  Light chain variable region of 496.g3

AIQLTQSPSSLSASVGDRVTITCRADESVRTLMHWYQQKPGKAPKLLIYLVSNSEIGVPDRFSGSGSG
TDFRLTISSLQPEDFATYYCQQTWSDPWTFGQGTKVEIK

SEQ ID NO:8  Light chain variable region of 496.g3 gcaatccagctcacccagagtccaagcagtctctccgccagcgtaggcgaccgtgtgactattacctg
tagagcggacgagtcggtcaggactctcatgcactggtatcaacagaagcctggtaaagctcctaaac
tgctcatctatctggtgtccaactcggagataggtgtgccagatcggtttagtgggtctggttcaggc
actgatttcagactgaccatatcatctctacagccagaggacttcgccacatattactgtcagcaaac
ctggagtgacccgtggactttcggccagggcactaaagtagaaattaaa SEQ ID NO:9  Heavy chain variable region of 496.g3

EVQLVESGGGLVQPGGSLRLSCAASGFTFSDYNMAWVRQAPGKGLEWVATITYEGRNTYYRDSVKGRF
TISRDNAKNSLYLQMNSLRAEDTAVYYCASPPQYYEGSIYRLWFAHWGQGTLVTVSS

Fig. 2 cont'd

SEQ ID NO:10  Heavy chain variable region of 496.g3

```
gaagttcagctggtcgagtctggaggtggccttgtccaacctggagggagcctgcgtctctcttgtgc
agcaagcggattcacgttttctgattacaatatggcttgggttagacaggcaccgggtaagggccttg
aatgggttgcgacgattacatacgaaggcagaaatacctattacagggactcagtaaaagggcggttt
accataagccgagataatgctaaaaacagtctgtatttgcaaatgaacagcctacgagctgaagacac
tgccgtgtattactgcgcgagtccacctcagtattatgaaggatcaatctatcgcctctggttcgcac
attggggacaggggacccttgtgacagtctcgagt
```

SEQ ID NO:11  Light chain (VL-CL) 496.g3

```
AIQLTQSPSSLSASVGDRVTITCRADESVRTLMHWYQQKPGKAPKLLIYLVSNSEIGVPDRFSGSGSG
TDFRLTISSLQPEDFATYYCQQTWSDPWTFGQGTKVEIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLSSP
VTKSFNRGEC
```

SEQ ID NO:12  Light chain (VL-CL) 496.g3

```
gcaatccagctcacccagagtccaagcagtctctccgccagcgtaggcgaccgtgtgactattacctg
tagagcggacgagtcggtcaggactctcatgcactggtatcaacagaagcctggtaaagctcctaaac
tgctcatctatctggtgtccaactcggagataggtgtgccagatcggtttagtgggtctggttcaggc
actgatttcagactgaccatatcatctctacagccagaggacttcgccacatattactgtcagcaaac
ctggagtgacccgtggactttcggccagggcactaaagtagaaattaaacgtacggtggccgctccct
ccgtgttcatcttcccaccctccgacgagcagctgaagtccggcaccgcctccgtcgtgtgcctgctg
aacaacttctaccccgcgaggccaaggtgcagtggaaggtggacaacgccctgcagtccggcaactc
ccaggaatccgtcaccgagcaggactccaaggacagcacctactccctgtcctccaccctgaccctgt
ccaaggccgactacgagaagcacaaggtgtacgcctgcgaagtgacccaccagggcctgtccagcccc
gtgaccaagtccttcaaccggggcgagtgc
```

SEQ ID NO:13  Heavy chain (VH-CH1) 496.g3

```
EVQLVESGGGLVQPGGSLRLSCAASGFTFSDYNMAWVRQAPGKGLEWVATITYEGRNTYYRDSVKGRF
TISRDNAKNSLYLQMNSLRAEDTAVYYCASPPQYYEGSIYRLWFAHWGQGTLVTVSSASTKGPSVFPL
APSSKSTSGGTAALGCLVKDYFPEPVTVSWNSGALTSGVHTFPAVLQSSGLYSLSSVVTVPSSSLGTQ
TYICNVNHKPSNTKVDKKVEPKSC
```

SEQ ID NO:14  Heavy chain (VH-CH1) 496.g3

```
gaagttcagctggtcgagtctggaggtggccttgtccaacctggagggagcctgcgtctctcttgtgc
agcaagcggattcacgttttctgattacaatatggcttgggttagacaggcaccgggtaagggccttg
aatgggttgcgacgattacatacgaaggcagaaatacctattacagggactcagtaaaagggcggttt
accataagccgagataatgctaaaaacagtctgtatttgcaaatgaacagcctacgagctgaagacac
tgccgtgtattactgcgcgagtccacctcagtattatgaaggatcaatctatcgcctctggttcgcac
attggggacaggggacccttgtgacagtctcgagtgcgtccacaaaaggcccatcggtcttccccctg
gcaccctcctccaagagcacctctggggggcacagcggccctgggctgcctggtcaaggactacttccc
cgaaccagtgacggtgtcgtggaactcaggtgccctgaccagcggcgttcacaccttcccggctgtcc
tacagtcttcaggactctactccctgagcagcgtggtgaccgtgccctccagcagcttgggcacccag
```

Fig. 2 cont'd acctacatctgcaacgtgaatcacaagcccagcaacaccaaggtcgataagaaagttgagcccaaatc
ttgt

Anti- IL-13

CDR sequences Ab 650 (1539)

SEQ ID NO:15  CDRL1 of Ab 650 (1539)

KASQNINENLD

SEQ ID NO:16  CDRL2 of Ab 650 (1539)

YTDILQT

SEQ ID NO:17  CDRL3 of Ab 650 (1539)

YQYYSGYT

SEQ ID NO:18  CDRH1 of Ab 650 (1539)

GYSFTSYYIH

SEQ ID NO:19  CDRH2 of Ab 650 (1539)

RIGPGSGDINYNEKFKG

SEQ ID NO:20  CDRH3 of Ab 650 (1539)

FHYDGAD

SEQ ID NO:21  Rat Ab 650 (1539) VL-region

DIQMTQSPPVLSASVGDRVTLSCKASQNINENLDWYHQKHGEAPKLLIYYTDILQTGIPSRFSGSGSG
TDYTLTISSLQPEDVATYYCYQYYSGYTFGPGTKLEIK

SEQ ID NO:22  Rat Ab 650 (1539) VL-region gacatccagatgacccagtctcctccagtcctgtctgcatctgtgggagacagagtcactctcagttg
caaagcaagtcagaatattaatgagaacttagactggtatcatcaaaagcatggcgaagctccaaaac
tcctgatatattatacagacattttgcaaacgggcatcccatcaaggttcagtggcagtggatctggt
acagattacacactcaccatcagcagcctgcagcctgaagatgttgccacatattactgctatcagta
ttacagtgggtacacgtttggacctgggaccaagctggaaataaaa <u>Fig. 2 cont'd</u>

SEQ ID NO:23  Rat Ab 650 (1539) VH-region

```
QVQLQQSGAELVKPGSSVKMSCKASGYSFTSYYIHWIKQRPGQGLEWIGRIGPGSGDINYNEKFKGKA
TFTVDKYFSTAYMQLSSLSPEDTAVFYCARFHYDGADWGQGTLVTVSS
```

SEQ ID NO:24  Rat Ab 650 (1539) VH-region

```
caggtacaactgcagcagtctggagctgagttggtgaagcctgggtcttcagtgaagatgtcctgcaa
ggcttctggctacagtttcaccagctactacatacactggataaagcagaggcctggacagggccttg
agtggattgggcgtattggtcctggaagtggagatattaattacaatgagaagttcaagggcaaggcc
acatttactgtggacaaatatttcagcacagcctacatgcaactcagcagcctgtcacctgaggacac
tgcggtcttttactgtgcaagatttcactatgatggggctgactggggccaaggcactctggtcacag
tctcgagc
```

SEQ ID NO:25  Human IGKV1-39 IGKJ2 acceptor framework

```
DIQMTQSPSSLSASVGDRVTITCRASQSISSYLNWYQQKPGKAPKLLIYAASSLQSGVPSRFSGSGSG
TDFTLTISSLQPEDFATYYCQQSYSTPYTFGQGTKLEIK
```

SEQ ID NO:26  Human IGHV1-69 IGHJ4 acceptor framework

```
QVQLVQSGAEVKKPGSSVKVSCKASGGTFSSYAISWVRQAPGQGLEWMGGIIPIFGTANYAQKFQGRV
TITADKSTSTAYMELSSLRSEDTAVYYCARYFDYWGQGTLVTVSS
```

SEQ ID NO:27  Ab 650 (1539) gL8 V-region (unmutated*)

```
DIQMTQSPSSLSASVGDRVTITCKASQNINENLDWYQQKPGKAPKLLIYYTDILQTGIPSRFSGSGSG
TDYTLTISSLQPEDFATYYCYQYYSGYTFGQGTKLEIK
```

SEQ ID NO:28  Ab 650 (1539) gH9 V-region (unmutated*)

```
EVQLVQSGAEVKKPGSSVKVSCKASGYSFTSYYIHWVRQAPGQGLEWMGRIGPGSGDINYNEKFKGRA
TFTVDKSTSTAYMELSSLRSEDTAVYYCARFHYDGADWGQGTLVTVSS
```

SEQ ID NO:29  Ab 650 (1539) gL8 V-region (unmutated*)

```
gacatccagatgacccagtccccctcctccctgtccgcctccgtgggcgacagggtgaccatcacctg
caaggcctcccagaacatcaacgagaacctggactggtaccagcagaagcccggcaaggcccccaagc
tgctgatctactacaccgacatcctgcagaccggcatcccctccaggttctccggctccggctccggc
accgactacaccctgaccatctcctccctgcagcccgaggacttcgccacctactactgctaccagta
ctactccggctacaccttcggccagggcaccaagctggagatcaag
```

SEQ ID NO:30  Ab 650 (1539) gH9 V-region (unmutated*)

```
gaggtgcagctggtgcagtccggcgccgaggtgaagaagcccggctcctccgtgaaggtgtcctgcaa
ggcctccggctactccttcacctcctactacatccactgggtgaggcaggcccccggccagggcctgg
```

Fig. 2 cont'd

```
agtggatgggcaggatcggccccggctccggcgacatcaactacaacgagaagttcaagggcagggcc
accttcaccgtggacaagtccacctccaccgcctacatggagctgtcctccctgaggtccgaggacac
cgccgtgtactactgcgccaggttccactacgacggcgccgactggggccagggcaccctggtgaccg
tctcgagc
```

SEQ ID NO:31  Ab 650 (1539) gL8 V-region (mutated**)

```
DIQMTQSPSSLSASVGDRVTITCKASQNINENLDWYQQKPGKAPKLLIYYTDILQTGIPSRFSGSGSG
TDYTLTISSLQPEDFATYYCYQYYSGYTFGCGTKLEIK
```

SEQ ID NO:32  Ab 650 (1539) gH9 V-region (mutated**)

```
EVQLVQSGAEVKKPGSSVKVSCKASGYSFTSYYIHWVRQAPGQCLEWMGRIGPGSGDINYNEKFKGRA
TFTVDKSTSTAYMELSSLRSEDTAVYYCARFHYDGADWGQGTLVTVSS
```

SEQ ID NO:33  Ab 650 (1539) gL8 V-region (mutated**)

```
gacatccagatgacccagtccccctcctccctgtccgcctccgtgggcgacagggtgaccatcacctg
caaggcctcccagaacatcaacgagaacctggactggtaccagcagaagcccggcaaggcccccaagc
tgctgatctactacaccgacatcctgcagaccggcatcccctccaggttctccggctccggctccggc
accgactacaccctgaccatctcctccctgcagcccgaggacttcgccacctactactgctaccagta
ctactccggctacaccttcggctgcggcaccaagctggagatcaag
```

SEQ ID NO:34  Ab 650 (1539) gH9 V-region (mutated**)

```
gaggtgcagctggtgcagtccggcgccgaggtgaagaagcccggctcctccgtgaaggtgtcctgcaa
ggcctccggctactccttcacctcctactacatccactgggtgaggcaggcccccggccagtgcctgg
agtggatgggcaggatcggccccggctccggcgacatcaactacaacgagaagttcaagggcagggcc
accttcaccgtggacaagtccacctccaccgcctacatggagctgtcctccctgaggtccgaggacac
cgccgtgtactactgcgccaggttccactacgacggcgccgactggggccagggcaccctggtgaccg
tgtcctcc
```

SEQ ID NO:35  650 (1539) scFv (VH/VL) gH9gL8 (unmutated*)

```
EVQLVQSGAEVKKPGSSVKVSCKASGYSFTSYYIHWVRQAPGQGLEWMGRIGPGSGDINYNEKFKGRA
TFTVDKSTSTAYMELSSLRSEDTAVYYCARFHYDGADWGQGTLVTVSSGGGGSGGGGSGGGGSGGGGS
DIQMTQSPSSLSASVGDRVTITCKASQNINENLDWYQQKPGKAPKLLIYYTDILQTGIPSRFSGSGSG
TDYTLTISSLQPEDFATYYCYQYYSGYTFGQGTKLEIK
```

SEQ ID NO:36  650 (1539) scFv (VH/VL) gH9gL8 (unmutated*)

```
gaggtgcagctggtgcagtccggcgccgaggtgaagaagcccggctcctccgtgaaggtgtcctgcaa
ggcctccggctactccttcacctcctactacatccactgggtgaggcaggcccccggccagggcctgg
agtggatgggcaggatcggccccggctccggcgacatcaactacaacgagaagttcaagggcagggcc
accttcaccgtggacaagtccacctccaccgcctacatggagctgtcctccctgaggtccgaggacac
cgccgtgtactactgcgccaggttccactacgacggcgccgactggggccagggcaccctggtgaccg
tgtcctccggaggtggcggttctggcggtggcggttccggtggcggtggatcgggaggtggcggttct
```

Fig. 2 cont'd

```
gacatccagatgacccagtcccctcctccctgtccgcctccgtgggcgacagggtgaccatcacctg
caaggcctcccagaacatcaacgagaacctggactggtaccagcagaagcccggcaaggcccccaagc
tgctgatctactacaccgacatcctgcagaccggcatcccctccaggttctccggctccggctccggc
accgactacaccctgaccatctcctccctgcagcccgaggacttcgccacctactactgctaccagta
ctactccggctacaccttcggccagggcaccaagctggagatcaag
```

SEQ ID NO:37  650 (1539) dsscFv (VH/VL) gH9gL8 (mutated**)

```
EVQLVQSGAEVKKPGSSVKVSCKASGYSFTSYYIHWVRQAPGQCLEWMGRIGPGSGDINYNEKFKGRA
TFTVDKSTSTAYMELSSLRSEDTAVYYCARFHYDGADWGQGTLVTVSSGGGGSGGGGSGGGGSGGGGS
DIQMTQSPSSLSASVGDRVTITCKASQNINENLDWYQQKPGKAPKLLIYYTDILQTGIPSRFSGSGSG
TDYTLTISSLQPEDFATYYCYQYYSGYTFGCGTKLEIK
```

SEQ ID NO:38  650 (1539) dsscFv (VH/VL) gH9gL8 (mutated**)

```
gaggtgcagctggtgcagtccggcgccgaggtgaagaagcccggctcctccgtgaaggtgtcctgcaa
ggcctccggctactccttcacctcctactacatccactgggtgaggcaggcccccggccagtgcctgg
agtggatgggcaggatcggcccggctccggcgacatcaactacaacgagaagttcaagggcagggcc
accttcaccgtggacaagtccacctccaccgcctacatggagctgtcctccctgaggtccgaggacac
cgccgtgtactactgcgccaggttccactacgacggcgccgactggggccagggcaccctggtgaccg
tgtcctccggaggtggcggttctggcggtggcggttccggtggcggtggatcgggaggtggcggttct
gacatccagatgacccagtcccctcctccctgtccgcctccgtgggcgacagggtgaccatcacctg
caaggcctcccagaacatcaacgagaacctggactggtaccagcagaagcccggcaaggcccccaagc
tgctgatctactacaccgacatcctgcagaccggcatcccctccaggttctccggctccggctccggc
accgactacaccctgaccatctcctccctgcagcccgaggacttcgccacctactactgctaccagta
ctactccggctacaccttcggctgcggcaccaagctggagatcaag
```

* ie without cysteines engineered for a disulphide bond
** ie with cysteines engineered for a disulphide bond

Anti- HSA

CDR sequences Ab 645

SEQ ID NO:39  CDRL1 of Ab 645

```
QSSPSVWSNFLS
```

SEQ ID NO:40  CDRL2 of Ab 645

```
EASKLTS
```

SEQ ID NO:41  CDRL3 of Ab 645

```
GGGYSSISDTT
```

Fig. 2 cont'd

SEQ ID NO:42  CDRH1 of Ab 645

GIDLSNYAIN

SEQ ID NO:43  CDRH2 of Ab 645

IIWASGTTFYATWAKG

SEQ ID NO:44  CDRH3 of Ab 645

TVPGYSTAPYFDL

SEQ ID NO:45  Ab 645 VL-region (unmutated*)

DIQMTQSPSSVSASVGDRVTITCQSSPSVWSNFLSWYQQKPGKAPKLLIYEASKLTSGVPSRFSGSGS
GTDFTLTISSLQPEDFATYYCGGGYSSISDTTFGGGTKVEIK

SEQ ID NO:46  Ab 645 VH-region (unmutated*)

EVQLLESGGGLVQPGGSLRLSCAVSGIDLSNYAINWVRQAPGKGLEWIGIIWASGTTFYATWAKGRFT
ISRDNSKNTVYLQMNSLRAEDTAVYYCARTVPGYSTAPYFDLWGQGTLVTVSS

SEQ ID NO:47  Ab 645 VL-region (unmutated*)

gatattcagatgacgcaatcaccttcgagcgtatccgcctcggtgggagacagggtgacaatcacttg
tcagtcatccccctcagtctggagcaactttttgtcatggtatcagcagaagcccggaaaggctccga
aattgctgatctacgaggcatcgaagttgacgagcggtgtaccaagcagattctccggttcggggtcg
ggaactgacttcacccttacgatctcatcgctgcagccggaggattttgcgacctactactgtggggg
tgggtattcgtcgatttccgacacaacattcggggcggcacgaaagtggaaatcaag SEQ ID NO:48  Ab 645 VH-region (unmutated*)

gaagtgcagttgctggagtcaggtggagggctggtgcagcccggaggatcgctgcggttgtcatgcgc
ggtgtccggtattgatttgtccaattacgccatcaattgggtacgccaagcgccagggaagggccttg
agtggattggcatcatctgggcgtcggggacgaccttttatgctacttgggccaaaggaagattcaca
atctcccgagacaactcgaagaacaccgtgtatcttcaaatgaactcgctcagggccgaggacacggc
ggtctactactgtgcacggacagtgccgggttattcaacggcaccttactttgatctttggggccagg
ggaccctcgtgactgtctcaagt SEQ ID NO:49  Ab 645 VL-region (mutated**)

DIQMTQSPSSVSASVGDRVTITCQSSPSVWSNFLSWYQQKPGKAPKLLIYEASKLTSGVPSRFSGSGS
GTDFTLTISSLQPEDFATYYCGGGYSSISDTTFGCGTKVEIK

Fig. 2 cont'd

SEQ ID NO:50  Ab 645 VH-region (mutated**)

```
EVQLLESGGGLVQPGGSLRLSCAVSGIDLSNYAINWVRQAPGKCLEWIGIIWASGTTFYATWAKGRFT
ISRDNSKNTVYLQMNSLRAEDTAVYYCARTVPGYSTAPYFDLWGQGTLVTVSS
```

SEQ ID NO:51  Ab 645 VL-region (mutated**)

```
gatattcagatgacgcaatcaccttcgagcgtatccgcctcggtgggagacagggtgacaatcacttg
tcagtcatccccctcagtctggagcaactttttgtcatggtatcagcagaagcccggaaaggctccga
aattgctgatctacgaggcatcgaagttgacgagcggtgtaccaagcagattctccggttcggggtcg
ggaactgacttcacccttacgatctcatcgctgcagccggaggattttgcgacctactactgtggggg
tgggtattcgtcgatttccgacacaacattcgggtgcggcacgaaagtggaaatcaag
```

SEQ ID NO:52  Ab 645 VH-region (mutated**)

```
gaagtgcagttgctggagtcaggtggagggctggtgcagcccggaggatcgctgcggttgtcatgcgc
ggtgtccggtattgatttgtccaattacgccatcaattgggtacgccaagcgccagggaagtgccttg
agtggattggcatcatctgggcgtcggggacgacctttttatgctacttgggccaaaggaagattcaca
atctcccgagacaactcgaagaacaccgtgtatcttcaaatgaactcgctcagggccgaggacacggc
ggtctactactgtgcacggacagtgccgggttattcaacggcaccttactttgatctttggggccagg
ggaccctcgtgactgtctcaagt
```

SEQ ID NO:53  645 scFv (VH/VL) (unmutated*)

```
EVQLLESGGGLVQPGGSLRLSCAVSGIDLSNYAINWVRQAPGKGLEWIGIIWASGTTFYATWAKGRFT
ISRDNSKNTVYLQMNSLRAEDTAVYYCARTVPGYSTAPYFDLWGQGTLVTVSSGGGGSGGGGSGGGGS
GGGGSDIQMTQSPSSVSASVGDRVTITCQSSPSVWSNFLSWYQQKPGKAPKLLIYEASKLTSGVPSRF
SGSGSGTDFTLTISSLQPEDFATYYCGGGYSSISDTTFGGGTKVEIK
```

SEQ ID NO:54  645 scFv (VH/VL) (unmutated*)

```
gaagtgcagttgctggagtcaggtggagggctggtgcagcccggaggatcgctgcggttgtcatgcgc
ggtgtccggtattgatttgtccaattacgccatcaattgggtacgccaagcgccagggaagggccttg
agtggattggcatcatctgggcgtcggggacgacctttttatgctacttgggccaaaggaagattcaca
atctcccgagacaactcgaagaacaccgtgtatcttcaaatgaactcgctcagggccgaggacacggc
ggtctactactgtgcacggacagtgccgggttattcaacggcaccttactttgatctttggggccagg
ggaccctcgtgactgtctcaagtggaggtggcggttctggcggtggcggttccggtggcggtggatcg
ggaggtggcggttctgatattcagatgacgcaatcaccttcgagcgtatccgcctcggtgggagacag
ggtgacaatcacttgtcagtcatccccctcagtctggagcaacttttttgtcatggtatcagcagaagc
ccggaaaggctccgaaattgctgatctacgaggcatcgaagttgacgagcggtgtaccaagcagattc
tccggttcggggtcgggaactgacttcacccttacgatctcatcgctgcagccggaggattttgcgac
ctactactgtggggtgggtattcgtcgatttccgacacaacattcgggggcggcacgaaagtggaaa
tcaag
```

Fig. 2 cont'd

SEQ ID NO:55  645 dsscFv (VH/VL) (mutated**)

```
EVQLLESGGGLVQPGGSLRLSCAVSGIDLSNYAINWVRQAPGKCLEWIGIIWASGTTFYATWAKGRFT
ISRDNSKNTVYLQMNSLRAEDTAVYYCARTVPGYSTAPYFDLWGQGTLVTVSSGGGGSGGGGSGGGGS
GGGGSDIQMTQSPSSVSASVGDRVTITCQSSPSVWSNFLSWYQQKPGKAPKLLIYEASKLTSGVPSRF
SGSGSGTDFTLTISSLQPEDFATYYCGGGYSSISDTTFGCGTKVEIK
```

SEQ ID NO:56  645 dsscFv (VH/VL) (mutated**)

```
gaagtgcagttgctggagtcaggtggagggctggtgcagcccggaggatcgctgcggttgtcatgcgc
ggtgtccggtattgatttgtccaattacgccatcaattgggtacgccaagcgccagggaagtgccttg
agtggattggcatcatctgggcgtcggggacgaccttttatgctacttgggccaaaggaagattcaca
atctcccgagacaactcgaagaacaccgtgtatcttcaaatgaactcgctcagggccgaggacacggc
ggtctactactgtgcacggacagtgccgggttattcaacggcaccttactttgatctttggggccagg
ggaccctcgtgactgtctcaagtggaggtggcggttctggcggtggcggttccggtggcggtggatcg
ggaggtggcggttctgatattcagatgacgcaatcaccttcgagcgtatccgcctcggtgggagacag
ggtgacaatcacttgtcagtcatccccctcagtctggagcaactttttgtcatggtatcagcagaagc
ccggaaaggctccgaaattgctgatctacgaggcatcgaagttgacgagcggtgtaccaagcagattc
tccggttcggggtcgggaactgacttcacccttacgatctcatcgctgcagccggaggattttgcgac
ctactactgtgggggtgggtattcgtcgatttccgacacaacattcgggtgcggcacgaaagtggaaa
tcaag
```

Full-length chains

SEQ ID NO:57  496.g3 HC- 645 (VH/VL) scFv (unmutated*)

```
EVQLVESGGGLVQPGGSLRLSCAASGFTFSDYNMAWVRQAPGKGLEWVATITYEGRNTYYRDSVKGRF
TISRDNAKNSLYLQMNSLRAEDTAVYYCASPPQYYEGSIYRLWFAHWGQGTLVTVSSASTKGPSVFPL
APSSKSTSGGTAALGCLVKDYFPEPVTVSWNSGALTSGVHTFPAVLQSSGLYSLSSVVTVPSSSLGTQ
TYICNVNHKPSNTKVDKKVEPKSCSGGGGTGGGGSEVQLLESGGGLVQPGGSLRLSCAVSGIDLSNYA
INWVRQAPGKGLEWIGIIWASGTTFYATWAKGRFTISRDNSKNTVYLQMNSLRAEDTAVYYCARTVPG
YSTAPYFDLWGQGTLVTVSSGGGGSGGGGSGGGGSGGGGSDIQMTQSPSSVSASVGDRVTITCQSSPS
VWSNFLSWYQQKPGKAPKLLIYEASKLTSGVPSRFSGSGSGTDFTLTISSLQPEDFATYYCGGGYSSI
SDTTFGGGTKVEIKRT
```

SEQ ID NO:58  496.g3 HC- 645 (VH/VL) scFv (unmutated*)

```
gaagttcagctggtcgagtctggaggtggccttgtccaacctggagggagcctgcgtctctcttgtgc
agcaagcggattcacgttttctgattacaatatggcttgggttagacaggcaccgggtaagggccttg
aatgggttgcgacgattacatacgaaggcagaaatacctattacagggactcagtaaaagggcggttt
accataagccgagataatgctaaaaacagtctgtatttgcaaatgaacagcctacgagctgaagacac
tgccgtgtattactgcgcgagtccacctcagtattatgaaggatcaatctatcgcctctggttcgcac
attggggacaggggacccttgtgacagtctcgagtgcgtccacaaagggcccatcggtcttcccctg
gcacctcctccaagagcacctctggggcacagcggccctggctgcctggtcaaggactacttccc
cgaaccagtgacggtgtcgtggaactcaggtgccctgaccagcggcgttcacaccttcccggctgtcc
tacagtcttcaggactctactccctgagcagcgtggtgaccgtgccctccagcagcttgggcacccag
acctacatctgcaacgtgaatcacaagcccagcaacaccaaggtcgataagaaagttgagcccaaatc
ttgtagcggtggcggtggcaccggaggtggcggttcagaagtgcagttgctggagtcaggtggagggc
```

Fig. 2 cont'd

```
tggtgcagcccggaggatcgctgcggttgtcatgcgcggtgtccggtattgatttgtccaattacgcc
atcaattgggtacgccaagcgccagggaagggccttgagtggattggcatcatctgggcgtcggggac
gacctttatgctacttgggccaaaggaagattcacaatctcccgagacaactcgaagaacaccgtgt
atcttcaaatgaactcgctcagggccgaggacacggcggtctactactgtgcacggacagtgccgggt
tattcaacggcaccttactttgatctttggggccagggggaccctcgtgactgtctcaagtggaggtgg
cggttctggcggtggcggttccggtggcggtggatcgggaggtggcggttctgatattcagatgacgc
aatcaccttcgagcgtatccgcctcggtgggagacaggtgacaatcacttgtcagtcatccccctca
gtctggagcaacttttgtcatggtatcagcagaagcccggaaaggctccgaaattgctgatctacga
ggcatcgaagttgacgagcggtgtaccaagcagattctccggttcggggtcgggaactgacttcaccc
ttacgatctcatcgctgcagccggaggattttgcgacctactactgtggggtgggtattcgtcgatt
tccgacacaacattcggggcggcacgaaagtggaaatcaagcgtacc
```

SEQ ID NO:59 496.g3 HC- 645 (VH/VL) dsscFv (mutated**)

```
EVQLVESGGGLVQPGGSLRLSCAASGFTFSDYNMAWVRQAPGKGLEWVATITYEGRNTYYRDSVKGRF
TISRDNAKNSLYLQMNSLRAEDTAVYYCASPPQYYEGSIYRLWFAHWGQGTLVTVSSASTKGPSVFPL
APSSKSTSGGTAALGCLVKDYFPEPVTVSWNSGALTSGVHTFPAVLQSSGLYSLSSVVTVPSSSLGTQ
TYICNVNHKPSNTKVDKKVEPKSCSGGGGTGGGGSEVQLLESGGGLVQPGGSLRLSCAVSGIDLSNYA
INWVRQAPGKCLEWIGIIWASGTTFYATWAKGRFTISRDNSKNTVYLQMNSLRAEDTAVYYCARTVPG
YSTAPYFDLWGQGTLVTVSSGGGGSGGGGSGGGGSGGGGSDIQMTQSPSSVSASVGDRVTITCQSSPS
VWSNFLSWYQQKPGKAPKLLIYEASKLTSGVPSRFSGSGSGTDFTLTISSLQPEDFATYYCGGGYSSI
SDTTFGCGTKVEIKRT
```

SEQ ID NO:60 496.g3 HC- 645 (VH/VL) dsscFv (mutated**)

```
gaagttcagctggtcgagtctggaggtggccttgtccaacctggagggagcctgcgtctctcttgtgc
agcaagcggattcacgttttctgattacaatatggcttgggttagacaggcaccgggtaagggccttg
aatgggttgcgacgattacatacgaaggcagaaatacctattcagggactcagtaaaagggcggttt
accataagccgagataatgctaaaaacagtctgtatttgcaaatgaacagcctacgagctgaagacac
tgccgtgtattactgcgcgagtccacctcagtattatgaaggatcaatctatcgcctctggttcgcac
attggggacaggggacccttgtgacagtctcgagtgcgtccacaaagggcccatcggtcttccccctg
gcaccctcctccaagagcacctctggggcacagcggccctgggctgcctggtcaaggactacttccc
cgaaccagtgacggtgtcgtggaactcaggtgccctgaccagcggcgttcacaccttccggctgtcc
tacagtcttcaggactctactccctgagcagcgtggtgaccgtgccctccagcagcttgggcacccag
acctacatctgcaacgtgaatcacaagcccagcaacaccaaggtcgataagaaagttgagcccaaatc
ttgtagcggtggcggtggcaccggaggtggcggttcagaagtgcagttgctggagtcaggtggagggc
tggtgcagcccggaggatcgctgcggttgtcatgcgcggtgtccggtattgatttgtccaattacgcc
atcaattgggtacgccaagcgccagggaagtgccttgagtggattggcatcatctgggcgtcggggac
gacctttatgctacttgggccaaaggaagattcacaatctcccgagacaactcgaagaacaccgtgt
atcttcaaatgaactcgctcagggccgaggacacggcggtctactactgtgcacggacagtgccgggt
tattcaacggcaccttactttgatctttggggccagggggaccctcgtgactgtctcaagtggaggtgg
cggttctggcggtggcggttccggtggcggtggatcgggaggtggcggttctgatattcagatgacgc
aatcaccttcgagcgtatccgcctcggtgggagacaggtgacaatcacttgtcagtcatccccctca
gtctggagcaacttttgtcatggtatcagcagaagcccggaaaggctccgaaattgctgatctacga
ggcatcgaagttgacgagcggtgtaccaagcagattctccggttcggggtcgggaactgacttcaccc
ttacgatctcatcgctgcagccggaggattttgcgacctactactgtggggtgggtattcgtcgatt
tccgacacaacattcgggtgcggcacgaaagtggaaatcaagcgtacc
```

<u>Fig. 2 cont'd</u>

SEQ ID NO:61  496.g3 LC- 650 (1539) scFv (unmutated*)

```
AIQLTQSPSSLSASVGDRVTITCRADESVRTLMHWYQQKPGKAPKLLIYLVSNSEIGVPDRFSGSGSG
TDFRLTISSLQPEDFATYYCQQTWSDPWTFGQGTKVEIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLSSP
VTKSFNRGECSGGGGSGGGGSEVQLVQSGAEVKKPGSSVKVSCKASGYSFTSYYIHWVRQAPGQGLEW
MGRIGPGSGDINYNEKFKGRATFTVDKSTSTAYMELSSLRSEDTAVYYCARFHYDGADWGQGTLVTVS
SGGGGSGGGGSGGGGSGGGGSDIQMTQSPSSLSASVGDRVTITCKASQNINENLDWYQQKPGKAPKLL
IYYTDILQTGIPSRFSGSGSGTDYTLTISSLQPEDFATYYCYQYYSGYTFGQGTKLEIKRT
```

SEQ ID NO:62  496.g3 LC- 650 (1539) scFv (unmutated*)

```
gcaatccagctcacccagagtccaagcagtctctccgccagcgtaggcgaccgtgtgactattacctg
tagagcggacgagtcggtcaggactctcatgcactggtatcaacagaagcctggtaaagctcctaaac
tgctcatctatctggtgtccaactcggagataggtgtgccagatcggtttagtgggtctggttcaggc
actgatttcagactgaccatatcatctctacagccagaggacttcgccacatattactgtcagcaaac
ctggagtgacccgtggactttcggccaggcactaaagtagaaattaaacgtacggtggccgctccct
ccgtgttcatcttcccaccctccgacgagcagctgaagtccggcaccgcctccgtcgtgtgcctgctg
aacaacttctaccccgcgaggccaaggtgcagtggaaggtggacaacgccctgcagtccggcaactc
ccaggaatccgtcaccgagcaggactccaaggacagcacctactccctgtcctccaccctgaccctgt
ccaaggccgactacgagaagcacaaggtgtacgcctgcgaagtgacccaccagggcctgtccagcccc
gtgaccaagtccttcaaccggggcgagtgcagcggtggcggtggctccggaggtggcggttcagaggt
gcagctggtgcagtccggcgccgaggtgaagaagcccggctcctccgtgaaggtgtcctgcaaggcct
ccggctactccttcacctcctactacatccactgggtgaggcaggcccccggccagggcctggagtgg
atgggcaggatcggccccggctccggcgacatcaactacaacgagaagttcaagggcagggccacctt
caccgtggacaagtccacctccaccgcctacatggagctgtcctccctgaggtccgaggacaccgccg
tgtactactgcgccaggttccactacgacggcgccgactggggccagggcaccctggtgaccgtgtcc
tccggaggtggcggttctggcggtggcggttccggtggcggtggatcgggaggtggcggttctgacat
ccagatgacccagtccccctcctccctgtccgcctccgtgggcgacagggtgaccatcacctgcaagg
cctcccagaacatcaacgagaacctggactggtaccagcagaagcccggcaaggcccccaagctgctg
atctactacaccgacatcctgcagaccggcatcccctccaggttctccggctccggctccggcaccga
ctacaccctgaccatctcctccctgcagcccgaggacttcgccacctactactgctaccagtactact
ccggctacaccttcggccagggcaccaagctggagatcaagcgtacc
```

SEQ ID NO:63  496.g3 LC- 650 (1539) dsscFv (mutated**)

```
AIQLTQSPSSLSASVGDRVTITCRADESVRTLMHWYQQKPGKAPKLLIYLVSNSEIGVPDRFSGSGSG
TDFRLTISSLQPEDFATYYCQQTWSDPWTFGQGTKVEIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLSSP
VTKSFNRGECSGGGGSGGGGSEVQLVQSGAEVKKPGSSVKVSCKASGYSFTSYYIHWVRQAPGQCLEW
MGRIGPGSGDINYNEKFKGRATFTVDKSTSTAYMELSSLRSEDTAVYYCARFHYDGADWGQGTLVTVS
SGGGGSGGGGSGGGGSGGGGSDIQMTQSPSSLSASVGDRVTITCKASQNINENLDWYQQKPGKAPKLL
IYYTDILQTGIPSRFSGSGSGTDYTLTISSLQPEDFATYYCYQYYSGYTFGCGTKLEIKRT
```

SEQ ID NO:64  496.g3 LC- 650 (1539) dsscFv (mutated**)

```
gcaatccagctcacccagagtccaagcagtctctccgccagcgtaggcgaccgtgtgactattacctg
tagagcggacgagtcggtcaggactctcatgcactggtatcaacagaagcctggtaaagctcctaaac
```

Fig. 2 cont'd

```
tgctcatctatctggtgtccaactcggagataggtgtgccagatcggtttagtgggtctggttcaggc
actgatttcagactgaccatatcatctctacagccagaggacttcgccacatattactgtcagcaaac
ctggagtgacccgtggactttcggccagggcactaaagtagaaattaaacgtacggtggccgctccct
ccgtgttcatcttcccacctccgacgagcagctgaagtccggcaccgcctccgtcgtgtgcctgctg
aacaacttctacccccgcgaggccaaggtgcagtggaaggtggacaacgccctgcagtccggcaactc
ccaggaatccgtcaccgagcaggactccaaggacagcacctactccctgtcctcacccctgaccctgt
ccaaggccgactacgagaagcacaaggtgtacgcctgcgaagtgacccaccagggcctgtccagcccc
gtgaccaagtccttcaaccggggcgagtgcagcggtggcggtggctccggaggtggcggttcagaggt
gcagctggtgcagtccggcgccgaggtgaagaagcccggctcctccgtgaaggtgtcctgcaaggcct
ccggctactccttcacctcctactacatccactgggtgaggcaggcccccggccagtgcctggagtgg
atgggcaggatcggccccggctccggcgacatcaactacaacgagaagttcaagggcagggccacctt
caccgtggacaagtccacctccaccgcctacatggagctgtcctccctgaggtccgaggacaccgccg
tgtactactgcgccaggttccactacgacggcgccgactggggccagggcaccctggtgaccgtgtcc
tccggaggtggcggttctggcggtggcggttccggtggcggtggatcgggaggtggcggttctgacat
ccagatgacccagtcccctcctccctgtccgcctccgtgggcgacagggtgaccatcacctgcaagg
cctcccagaacatcaacgagaacctggactggtaccagcagaagcccggcaaggcccccaagctgctg
atctactacaccgacatcctgcagaccggcatcccctccaggttctccggctccggctccggcaccga
ctacaccctgaccatctcctccctgcagcccgaggacttcgccacctactactgctaccagtactact
ccggctacaccttcggctgcggcaccaagctggagatcaagcgtacc
```

\* ie without cysteines engineered for a disulphide bond
\*\* ie with cysteines engineered for a disulphide bond Linkers SEQ ID NO:65  Light chain linker between kappa constant region and 650 (1539) VH of scFv/dssFv
645 VH of scFv/dssFv

SGGGGSGGGGS

SEQ ID NO:66  Light chain linker between VH and VL of 650 (1539) scFv/dsscFv 645 scFv/dsscFv

GGGGSGGGGSGGGGSGGGGS

SEQ ID NO:67  Heavy chain linker between CH1 constant region and 645 VH of scFv/dssFv

SGGGGTGGGGS

SEQ ID NO:68  Heavy chain linker between VH and VL of 645 scFv/dsscFv

GGGGSGGGGSGGGGSGGGGS

<u>Figure 3.  Purification of IL-13/IL-17AF multi-specific antibody</u>
(A)  BEH200 SEC-UPLC analysis of final purified antibody, detection by FLR.
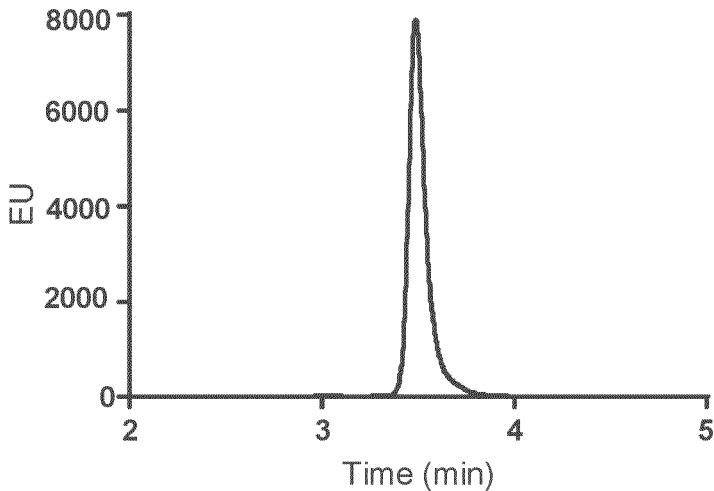
(B)  SDS-PAGE under non-reducing (lane 1) or reducing (lane 2) conditions.
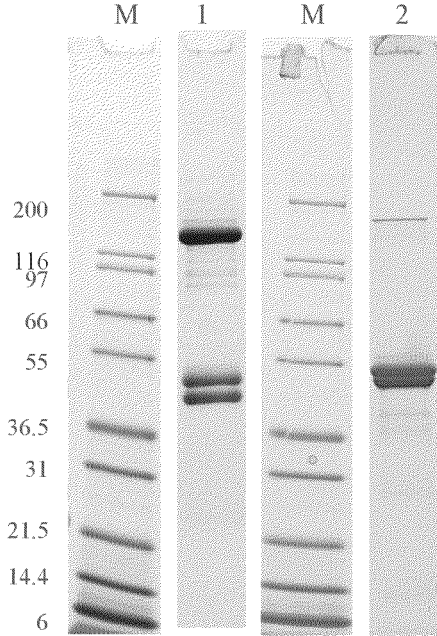

Figure 4.  Inhibition of STAT6 signalling
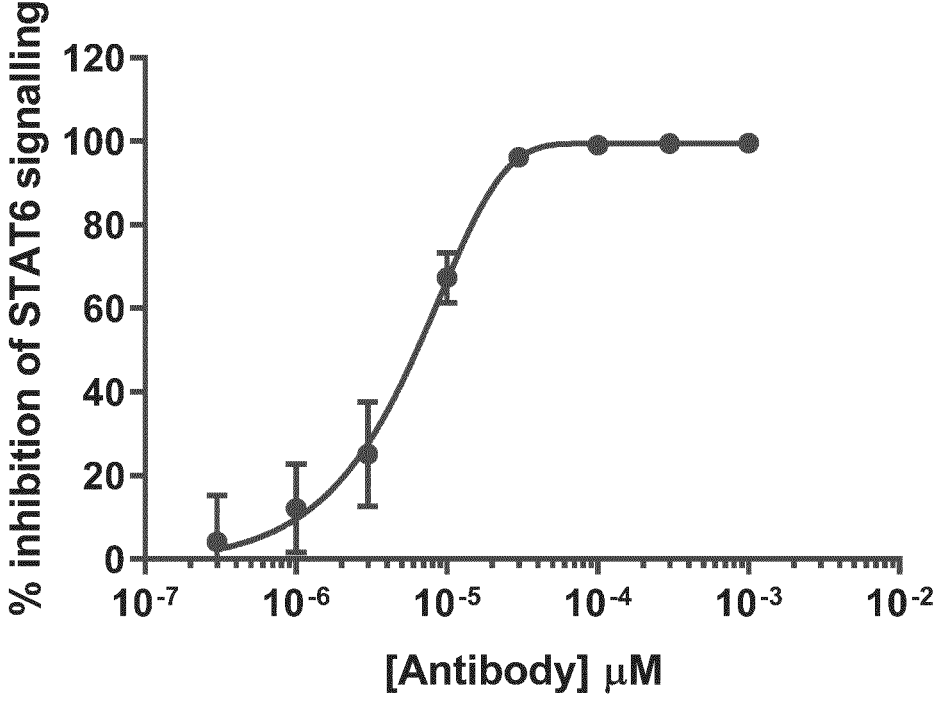

Figure 5(A)  Inhibition of IL-6 production in response to human or cynomolgus IL-17A in combination with TNF-α.
(i) Human IL-17A.
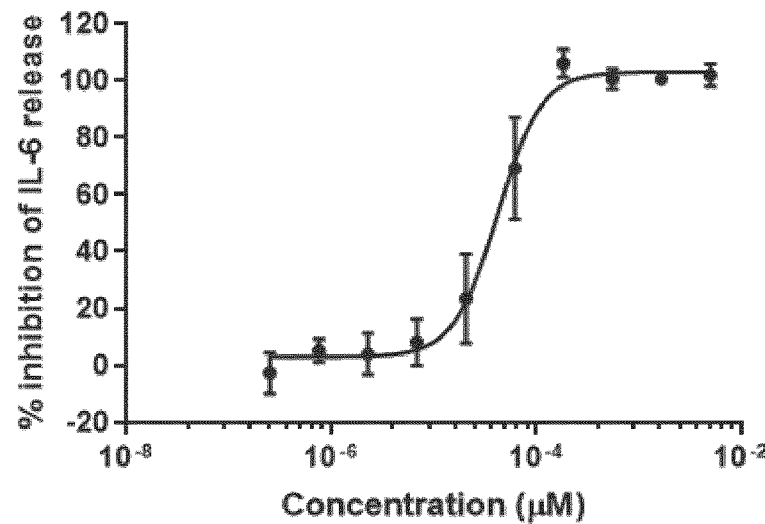
(ii) Cynomolgus IL-17A.
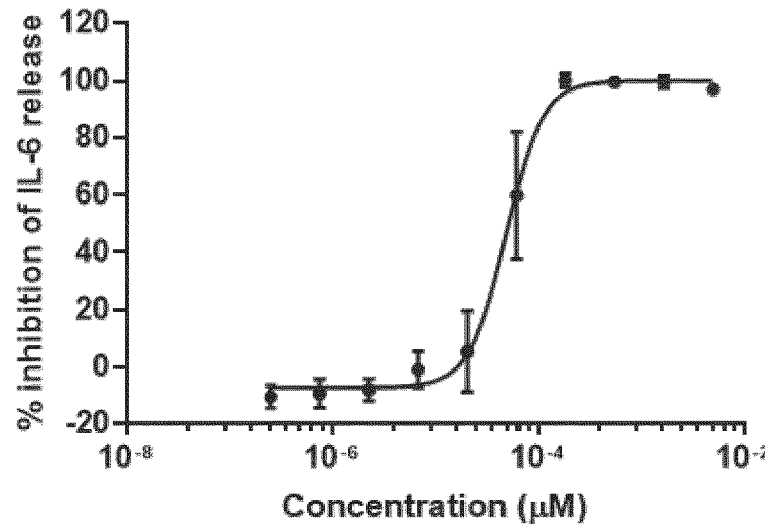

Figure 5(B)  Inhibition of IL-6 production in response to human or cynomolgus IL-17F in combination with TNF-α.
(i) Human IL-17F.
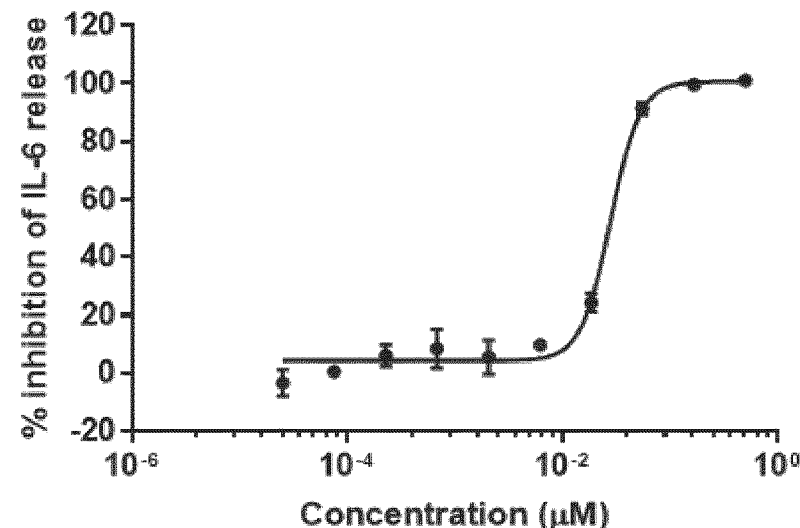
(ii) Cynomolgus IL-17F.
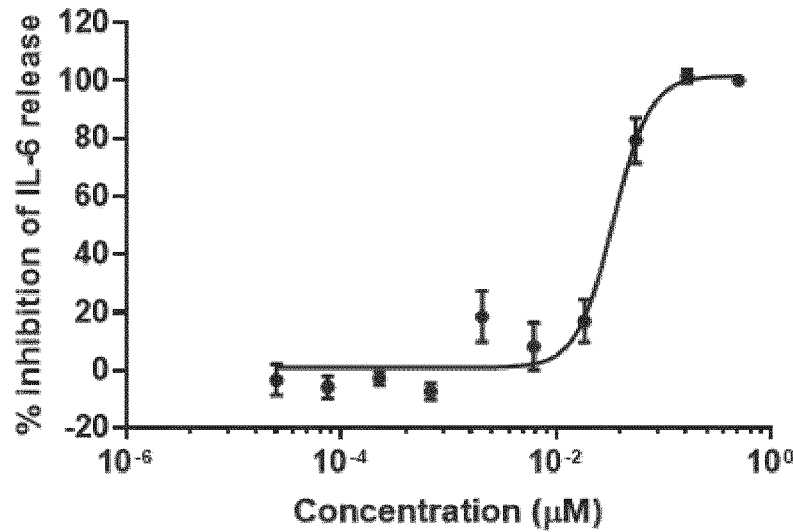

Figure 6.  Simultaneous neutralisation of IL-13, IL-17A and IL-17F by IL-13/IL-17AF
multi-specific antibody
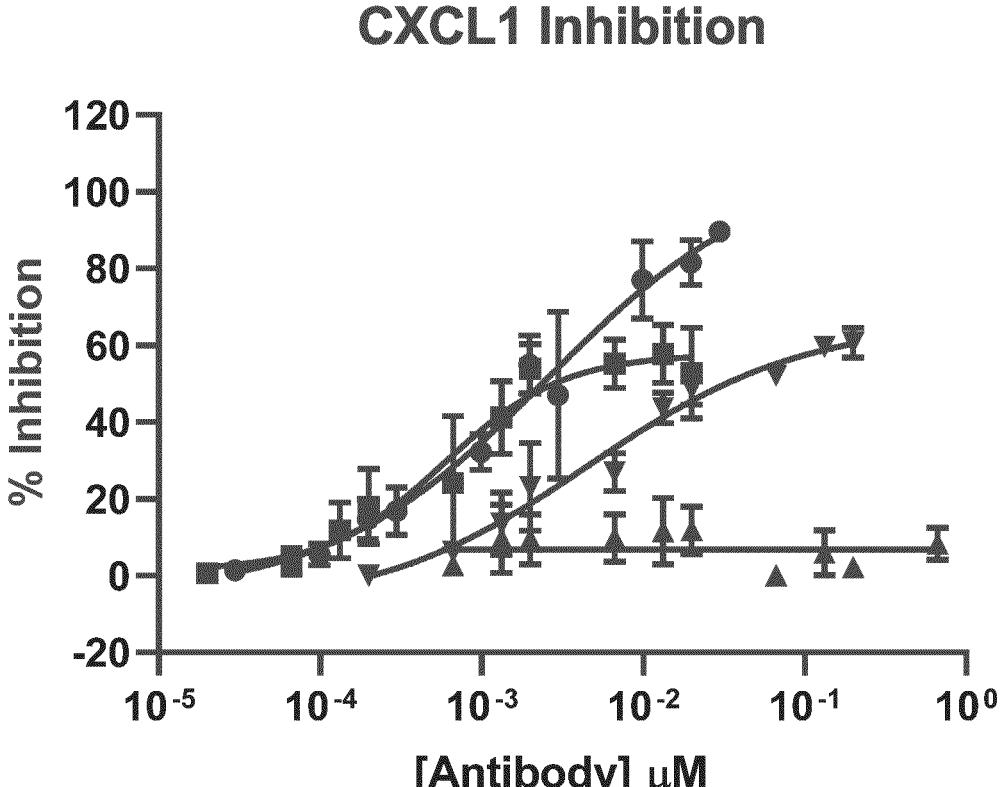

anti IL-17A/F Fab anti albumin scFv          anti IL-13 scFv

Heavy Chain          Light Chain

SEQUENCE LISTING

<160> NUMBER OF SEQ ID NOS: 68

<210> SEQ ID NO 1
<211> LENGTH: 11
<212> TYPE: PRT
<213> ORGANISM: Artificial Sequence
<220> FEATURE:
<223> OTHER INFORMATION: recombinant sequence

<400> SEQUENCE: 1

Arg Ala Asp Glu Ser Val Arg Thr Leu Met His
1               5                   10

<210> SEQ ID NO 2
<211> LENGTH: 7
<212> TYPE: PRT
<213> ORGANISM: Artificial Sequence
<220> FEATURE:
<223> OTHER INFORMATION: recombinant sequence

<400> SEQUENCE: 2

Leu Val Ser Asn Ser Glu Ile
1               5

<210> SEQ ID NO 3
<211> LENGTH: 9
<212> TYPE: PRT
<213> ORGANISM: Artificial Sequence
<220> FEATURE:
<223> OTHER INFORMATION: recombinant sequence

<400> SEQUENCE: 3

Gln Gln Thr Trp Ser Asp Pro Trp Thr
1               5

<210> SEQ ID NO 4
<211> LENGTH: 10
<212> TYPE: PRT
<213> ORGANISM: Artificial Sequence
<220> FEATURE:
<223> OTHER INFORMATION: recombinant sequence

<400> SEQUENCE: 4

Gly Phe Thr Phe Ser Asp Tyr Asn Met Ala
1               5                   10

<210> SEQ ID NO 5
<211> LENGTH: 17
<212> TYPE: PRT
<213> ORGANISM: Artificial Sequence
<220> FEATURE:
<223> OTHER INFORMATION: recombinant sequence

<400> SEQUENCE: 5

Thr Ile Thr Tyr Glu Gly Arg Asn Thr Tyr Tyr Arg Asp Ser Val Lys
1               5                   10                  15

Gly

<210> SEQ ID NO 6
<211> LENGTH: 16
<212> TYPE: PRT
<213> ORGANISM: Artificial Sequence
<220> FEATURE:
<223> OTHER INFORMATION: recombinant sequence

<400> SEQUENCE: 6

-continued

```
Pro Pro Gln Tyr Tyr Glu Gly Ser Ile Tyr Arg Leu Trp Phe Ala His
1               5                   10                  15

<210> SEQ ID NO 7
<211> LENGTH: 107
<212> TYPE: PRT
<213> ORGANISM: Artificial Sequence
<220> FEATURE:
<223> OTHER INFORMATION: recombinant sequence

<400> SEQUENCE: 7

Ala Ile Gln Leu Thr Gln Ser Pro Ser Ser Leu Ser Ala Ser Val Gly
1               5                   10                  15

Asp Arg Val Thr Ile Thr Cys Arg Ala Asp Glu Ser Val Arg Thr Leu
            20                  25                  30

Met His Trp Tyr Gln Gln Lys Pro Gly Lys Ala Pro Lys Leu Leu Ile
        35                  40                  45

Tyr Leu Val Ser Asn Ser Glu Ile Gly Val Pro Asp Arg Phe Ser Gly
    50                  55                  60

Ser Gly Ser Gly Thr Asp Phe Arg Leu Thr Ile Ser Ser Leu Gln Pro
65                  70                  75                  80

Glu Asp Phe Ala Thr Tyr Tyr Cys Gln Gln Thr Trp Ser Asp Pro Trp
                85                  90                  95

Thr Phe Gly Gln Gly Thr Lys Val Glu Ile Lys
            100                 105

<210> SEQ ID NO 8
<211> LENGTH: 321
<212> TYPE: DNA
<213> ORGANISM: Artificial Sequence
<220> FEATURE:
<223> OTHER INFORMATION: recombinant sequence

<400> SEQUENCE: 8
gcaatccagc tcacccagag tccaagcagt ctctccgcca gcgtaggcga ccgtgtgact       60
attacctgta gagcggacga gtcggtcagg actctcatgc actggtatca acagaagcct      120
ggtaaagctc ctaaactgct catctatctg gtgtccaact cggagatagg tgtgccagat      180
cggtttagtg ggtctggttc aggcactgat ttcagactga ccatatcatc tctacagcca      240
gaggacttcg ccacatatta ctgtcagcaa acctggagtg acccgtggac tttcggccag      300
ggcactaaag tagaaattaa a                                                 321

<210> SEQ ID NO 9
<211> LENGTH: 125
<212> TYPE: PRT
<213> ORGANISM: Artificial Sequence
<220> FEATURE:
<223> OTHER INFORMATION: recombinant sequence

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asn Met Ala Trp Val Arg Gln Ala Pro Gly Lys Gly Leu Glu Trp Val
        35                  40                  45

Ala Thr Ile Thr Tyr Glu Gly Arg Asn Thr Tyr Tyr Arg Asp Ser Val
    50                  55                  60

Lys Gly Arg Phe Thr Ile Ser Arg Asp Asn Ala Lys Asn Ser Leu Tyr
```

```
65              70              75              80

Leu Gln Met Asn Ser Leu Arg Ala Glu Asp Thr Ala Val Tyr Tyr Cys
                85              90              95

Ala Ser Pro Pro Gln Tyr Tyr Glu Gly Ser Ile Tyr Arg Leu Trp Phe
            100             105             110

Ala His Trp Gly Gln Gly Thr Leu Val Thr Val Ser Ser
        115             120             125

<210> SEQ ID NO 10
<211> LENGTH: 375
<212> TYPE: DNA
<213> ORGANISM: Artificial Sequence
<220> FEATURE:
<223> OTHER INFORMATION: recombinant sequence

<400> SEQUENCE: 10
gaagttcagc tggtcgagtc tggaggtggc cttgtccaac ctggagggag cctgcgtctc      60
tcttgtgcag caagcggatt cacgttttct gattacaata tggcttgggt tagacaggca     120
ccgggtaagg gccttgaatg ggttgcgacg attacatacg aaggcagaaa tacctattac     180
agggactcag taaaagggcg gtttaccata agccgagata tgctaaaaaa cagtctgtat     240
ttgcaaatga acagcctacg agctgaagac actgccgtgt attactgcgc gagtccacct     300
cagtattatg aaggatcaat ctatcgcctc tggttcgcac attggggaca ggggacccct     360
gtgacagtct cgagt                                                       375

<210> SEQ ID NO 11
<211> LENGTH: 214
<212> TYPE: PRT
<213> ORGANISM: Artificial Sequence
<220> FEATURE:
<223> OTHER INFORMATION: recombinant sequence

<400> SEQUENCE: 11

Ala Ile Gln Leu Thr Gln Ser Pro Ser Ser Leu Ser Ala Ser Val Gly
1               5               10              15

Asp Arg Val Thr Ile Thr Cys Arg Ala Asp Glu Ser Val Arg Thr Leu
            20              25              30

Met His Trp Tyr Gln Gln Lys Pro Gly Lys Ala Pro Lys Leu Leu Ile
        35              40              45

Tyr Leu Val Ser Asn Ser Glu Ile Gly Val Pro Asp Arg Phe Ser Gly
    50              55              60

Ser Gly Ser Gly Thr Asp Phe Arg Leu Thr Ile Ser Ser Leu Gln Pro
65              70              75              80

Glu Asp Phe Ala Thr Tyr Tyr Cys Gln Gln Thr Trp Ser Asp Pro Trp
                85              90              95

Thr Phe Gly Gln Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
        130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
```

```
            180              185              190
Ala Cys Glu Val Thr His Gln Gly Leu Ser Ser Pro Val Thr Lys Ser
        195              200              205

Phe Asn Arg Gly Glu Cys
    210

<210> SEQ ID NO 12
<211> LENGTH: 642
<212> TYPE: DNA
<213> ORGANISM: Artificial Sequence
<220> FEATURE:
<223> OTHER INFORMATION: recombinant sequence

<400> SEQUENCE: 12
gcaatccagc tcacccagag tccaagcagt ctctccgcca gcgtaggcga ccgtgtgact       60
attacctgta gagcggacga gtcggtcagg actctcatgc actggtatca acagaagcct      120
ggtaaagctc ctaaactgct catctatctg gtgtccaact cggagatagg tgtgccagat      180
cggtttagtg ggtctggttc aggcactgat ttcagactga ccatatcatc tctacagcca      240
gaggacttcg ccacatatta ctgtcagcaa acctggagtg acccgtggac tttcggccag      300
ggcactaaag tagaaattaa acgtacggtg gccgctccct ccgtgttcat cttcccaccc      360
tccgacgagc agctgaagtc cggcaccgcc tccgtcgtgt gcctgctgaa caacttctac      420 cccgcgagc ccaaggtgca gtggaaggtg gacaacgccc tgcagtccgg caactcccag      480
gaatccgtca ccgagcagga ctccaaggac agcacctact ccctgtcctc caccctgacc      540
ctgtccaagg ccgactacga gaagcacaag gtgtacgcct gcgaagtgac ccaccagggc      600
ctgtccagcc ccgtgaccaa gtccttcaac cggggcgagt gc                        642

<210> SEQ ID NO 13
<211> LENGTH: 228
<212> TYPE: PRT
<213> ORGANISM: Artificial Sequence
<220> FEATURE:
<223> OTHER INFORMATION: recombinant sequence

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asn Met Ala Trp Val Arg Gln Ala Pro Gly Lys Gly Leu Glu Trp Val
        35                  40                  45

Ala Thr Ile Thr Tyr Glu Gly Arg Asn Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gln Tyr Tyr Glu Gly Ser Ile Tyr Arg Leu Trp Phe
            100                 105                 110

Ala His Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160
```

```
Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
        180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys
225
```

```
<210> SEQ ID NO 14
<211> LENGTH: 684
<212> TYPE: DNA
<213> ORGANISM: Artificial Sequence
<220> FEATURE:
<223> OTHER INFORMATION: recombinant sequence

<400> SEQUENCE: 14
gaagttcagc tggtcgagtc tggaggtggc cttgtccaac ctggagggag cctgcgtctc      60
tcttgtgcag caagcggatt cacgttttct gattacaata tggcttgggt tagacaggca     120
ccgggtaagg gccttgaatg ggttgcgacg attacatacg aaggcagaaa tacctattac     180
agggactcag taaaagggcg gtttaccata agccgagata tgctaaaaa cagtctgtat      240 ttgcaaatga acagcctacg agctgaagac actgccgtgt attactgcgc gagtccacct     300
cagtattatg aaggatcaat ctatcgcctc tggttcgcac attggggaca ggggaccctt     360
gtgacagtct cgagtgcgtc cacaaagggc ccatcggtct tccccctggc accctcctcc     420
aagagcacct ctgggggcac agcggccctg ggctgcctgg tcaaggacta cttccccgaa     480
ccagtgacgg tgtcgtggaa ctcaggtgcc ctgaccagcg gcgttcacac cttcccggct     540
gtcctacagt cttcaggact ctactccctg agcagcgtgg tgaccgtgcc ctccagcagc     600
ttgggcaccc agacctacat ctgcaacgtg aatcacaagc ccagcaacac caaggtcgat     660
aagaaagttg agcccaaatc ttgt                                            684
```

```
<210> SEQ ID NO 15
<211> LENGTH: 11
<212> TYPE: PRT
<213> ORGANISM: Artificial Sequence
<220> FEATURE:
<223> OTHER INFORMATION: recombinant sequence

<400> SEQUENCE: 15

Lys Ala Ser Gln Asn Ile Asn Glu Asn Leu Asp
1               5                   10
```

```
<210> SEQ ID NO 16
<211> LENGTH: 7
<212> TYPE: PRT
<213> ORGANISM: Artificial Sequence
<220> FEATURE:
<223> OTHER INFORMATION: recombinant sequence

<400> SEQUENCE: 16

Tyr Thr Asp Ile Leu Gln Thr
1               5
```

```
<210> SEQ ID NO 17
<211> LENGTH: 8
```

```
<212> TYPE: PRT
<213> ORGANISM: Artificial Sequence
<220> FEATURE:
<223> OTHER INFORMATION: recombinant sequence

<400> SEQUENCE: 17

Tyr Gln Tyr Tyr Ser Gly Tyr Thr
1               5

<210> SEQ ID NO 18
<211> LENGTH: 10
<212> TYPE: PRT
<213> ORGANISM: Artificial Sequence
<220> FEATURE:
<223> OTHER INFORMATION: recombinant sequence

<400> SEQUENCE: 18

Gly Tyr Ser Phe Thr Ser Tyr Tyr Ile His
1               5                   10

<210> SEQ ID NO 19
<211> LENGTH: 17
<212> TYPE: PRT
<213> ORGANISM: Artificial Sequence
<220> FEATURE:
<223> OTHER INFORMATION: recombinant sequence

<400> SEQUENCE: 19

Arg Ile Gly Pro Gly Ser Gly Asp Ile Asn Tyr Asn Glu Lys Phe Lys
1               5                   10                  15

Gly

<210> SEQ ID NO 20
<211> LENGTH: 7
<212> TYPE: PRT
<213> ORGANISM: Artificial Sequence
<220> FEATURE:
<223> OTHER INFORMATION: recombinant sequence

<400> SEQUENCE: 20

Phe His Tyr Asp Gly Ala Asp
1               5

<210> SEQ ID NO 21
<211> LENGTH: 106
<212> TYPE: PRT
<213> ORGANISM: Artificial Sequence
<220> FEATURE:
<223> OTHER INFORMATION: recombinant sequence

<400> SEQUENCE: 21

Asp Ile Gln Met Thr Gln Ser Pro Pro Val Leu Ser Ala Ser Val Gly
1               5                   10                  15

Asp Arg Val Thr Leu Ser Cys Lys Ala Ser Gln Asn Ile Asn Glu Asn
                20                  25                  30

Leu Asp Trp Tyr His Gln Lys His Gly Glu Ala Pro Lys Leu Leu Ile
            35                  40                  45

Tyr Tyr Thr Asp Ile Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Tyr Ser Gly Tyr Thr
                85                  90                  95
```

```
Phe Gly Pro Gly Thr Lys Leu Glu Ile Lys
        100                 105

<210> SEQ ID NO 22
<211> LENGTH: 318
<212> TYPE: DNA
<213> ORGANISM: Artificial Sequence
<220> FEATURE:
<223> OTHER INFORMATION: recombinant sequence

<400> SEQUENCE: 22
gacatccaga tgacccagtc tcctccagtc ctgtctgcat ctgtgggaga cagagtcact      60
ctcagttgca aagcaagtca gaatattaat gagaacttag actggtatca tcaaaagcat     120
ggcgaagctc caaaactcct gatatattat acagacattt tgcaaacggg catcccatca     180
aggttcagtg gcagtggatc tggtacagat tacacactca ccatcagcag cctgcagcct     240
gaagatgttg ccacatatta ctgctatcag tattacagtg ggtacacgtt tggacctggg     300
accaagctgg aaataaaa                                                    318

<210> SEQ ID NO 23
<211> LENGTH: 116
<212> TYPE: PRT
<213> ORGANISM: Artificial Sequence
<220> FEATURE:
<223> OTHER INFORMATION: recombinant sequence

<400> SEQUENCE: 23

Gln Val Gln Leu Gln Gln Ser Gly Ala Glu Leu Val Lys Pro Gly Ser
1               5                   10                  15

Ser Val Lys Met Ser Cys Lys Ala Ser Gly Tyr Ser Phe Thr Ser Tyr
            20                  25                  30

Tyr Ile His Trp Ile Lys Gln Arg Pro Gly Gln Gly Leu Glu Trp Ile
        35                  40                  45

Gly Arg Ile Gly Pro Gly Ser Gly Asp Ile Asn Tyr Asn Glu Lys Phe
    50                  55                  60

Lys Gly Lys Ala Thr Phe Thr Val Asp Lys Tyr Phe Ser Thr Ala Tyr
65                  70                  75                  80

Met Gln Leu Ser Ser Leu Ser Pro Glu Asp Thr Ala Val Phe Tyr Cys
                85                  90                  95

Ala Arg Phe His Tyr Asp Gly Ala Asp Trp Gly Gln Gly Thr Leu Val
            100                 105                 110

Thr Val Ser Ser
        115

<210> SEQ ID NO 24
<211> LENGTH: 348
<212> TYPE: DNA
<213> ORGANISM: Artificial Sequence
<220> FEATURE:
<223> OTHER INFORMATION: recombinant sequence

<400> SEQUENCE: 24
caggtacaac tgcagcagtc tggagctgag ttggtgaagc ctgggtcttc agtgaagatg      60
tcctgcaagg cttctggcta cagtttcacc agctactaca tacactggat aaagcagagg     120
cctggacagg gccttgagtg gattgggcgt attggtcctg gaagtggaga tattaattac     180
aatgagaagt tcaagggcaa ggccacattt actgtggaca atatttttcag cacagcctac     240 atgcaactca gcagcctgtc acctgaggac actgcggtct tttactgtgc aagatttcac     300
```

-continued

```
tatgatgggg ctgactgggg ccaaggcact ctggtcacag tctcgagc                    348
```

<210> SEQ ID NO 25
<211> LENGTH: 107
<212> TYPE: PRT
<213> ORGANISM: Artificial Sequence
<220> FEATURE:
<223> OTHER INFORMATION: recombinant sequence

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105
```

<210> SEQ ID NO 26
<211> LENGTH: 113
<212> TYPE: PRT
<213> ORGANISM: Artificial Sequence
<220> FEATURE:
<223> OTHER INFORMATION: recombinant sequence

<400> SEQUENCE: 26

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser
```

<210> SEQ ID NO 27
<211> LENGTH: 106
<212> TYPE: PRT
<213> ORGANISM: Artificial Sequence
<220> FEATURE:
<223> OTHER INFORMATION: recombinant sequence

<400> SEQUENCE: 27

```
Asp Ile Gln Met Thr Gln Ser Pro Ser Ser Leu Ser Ala Ser Val Gly
1               5                   10                  15
```

```
Asp Arg Val Thr Ile Thr Cys Lys Ala Ser Gln Asn Ile Asn Glu Asn
            20                  25                  30

Leu Asp Trp Tyr Gln Gln Lys Pro Gly Lys Ala Pro Lys Leu Leu Ile
        35                  40                  45

Tyr Tyr Thr Asp Ile Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Tyr Gln Tyr Tyr Ser Gly Tyr Thr
                85                  90                  95

Phe Gly Gln Gly Thr Lys Leu Glu Ile Lys
            100                 105
```

<210> SEQ ID NO 28
<211> LENGTH: 116
<212> TYPE: PRT
<213> ORGANISM: Artificial Sequence
<220> FEATURE:
<223> OTHER INFORMATION: recombinant sequence

<400> SEQUENCE: 28

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Gly Leu Glu Trp Met
        35                  40                  45

Gly Arg Ile Gly Pro Gly Ser Gly Asp Ile Asn Tyr Asn Glu Lys Phe
    50                  55                  60

Lys Gly Arg Ala Thr Phe Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe His Tyr Asp Gly Ala Asp Trp Gly Gln Gly Thr Leu Val
            100                 105                 110

Thr Val Ser Ser
        115
```

<210> SEQ ID NO 29
<211> LENGTH: 318
<212> TYPE: DNA
<213> ORGANISM: Artificial Sequence
<220> FEATURE:
<223> OTHER INFORMATION: recombinant sequence

<400> SEQUENCE: 29

```
gacatccaga tgacccagtc ccctcctcc ctgtccgcct ccgtgggcga cagggtgacc      60
atcacctgca aggcctccca gaacatcaac gagaacctgg actggtacca gcagaagccc     120
ggcaaggccc ccaagctgct gatctactac accgacatcc tgcagaccgg catcccctcc     180
aggttctccg gctccggctc cggcaccgac tacaccctga ccatctcctc cctgcagccc     240
gaggacttcg ccacctacta ctgctaccag tactactccg gctacacctt cggccagggc     300
accaagctgg agatcaag                                                    318
```

<210> SEQ ID NO 30
<211> LENGTH: 348
<212> TYPE: DNA
<213> ORGANISM: Artificial Sequence

```
<220> FEATURE:
<223> OTHER INFORMATION: recombinant sequence

<400> SEQUENCE: 30
gaggtgcagc tggtgcagtc cggcgccgag gtgaagaagc ccggctcctc cgtgaaggtg      60
tcctgcaagg cctccggcta ctccttcacc tcctactaca tccactgggt gaggcaggcc     120
cccggccagg gcctggagtg gatgggcagg atcggccccg gctccggcga catcaactac     180
aacgagaagt tcaagggcag ggccaccttc accgtggaca gtccacctc caccgcctac     240 atggagctgt cctccctgag gtccgaggac accgccgtgt actactgcgc caggttccac     300
tacgacggcg ccgactgggg ccagggcacc ctggtgaccg tctcgagc                 348
```

```
<210> SEQ ID NO 31
<211> LENGTH: 106
<212> TYPE: PRT
<213> ORGANISM: Artificial Sequence
<220> FEATURE:
<223> OTHER INFORMATION: recombinant sequence

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Glu Asn
                20                  25                  30

Leu Asp Trp Tyr Gln Gln Lys Pro Gly Lys Ala Pro Lys Leu Leu Ile
            35                  40                  45

Tyr Tyr Thr Asp Ile Leu Gln Thr Gly Ile Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Tyr Gln Tyr Tyr Ser Gly Tyr Thr
                85                  90                  95

Phe Gly Cys Gly Thr Lys Leu Glu Ile Lys
            100                 105
```

```
<210> SEQ ID NO 32
<211> LENGTH: 116
<212> TYPE: PRT
<213> ORGANISM: Artificial Sequence
<220> FEATURE:
<223> OTHER INFORMATION: recombinant sequence

<400> SEQUENCE: 32

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Ser Tyr
                20                  25                  30

Tyr Ile His Trp Val Arg Gln Ala Pro Gly Gln Cys Leu Glu Trp Met
            35                  40                  45

Gly Arg Ile Gly Pro Gly Ser Gly Asp Ile Asn Tyr Asn Glu Lys Phe
        50                  55                  60

Lys Gly Arg Ala Thr Phe Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe His Tyr Asp Gly Ala Asp Trp Gly Gln Gly Thr Leu Val
            100                 105                 110
```

-continued

```
Thr Val Ser Ser
        115

<210> SEQ ID NO 33
<211> LENGTH: 318
<212> TYPE: DNA
<213> ORGANISM: Artificial Sequence
<220> FEATURE:
<223> OTHER INFORMATION: recombinant sequence

<400> SEQUENCE: 33
gacatccaga tgacccagtc cccctcctcc ctgtccgcct ccgtgggcga cagggtgacc      60
atcacctgca aggcctccca gaacatcaac gagaacctgg actggtacca gcagaagccc     120
ggcaaggccc ccaagctgct gatctactac accgacatcc tgcagaccgg catcccctcc     180
aggttctccg gctccggctc cggcaccgac tacaccctga ccatctcctc cctgcagccc     240
gaggacttcg ccacctacta ctgctaccag tactactccg ctacacctt cggctgcggc      300 accaagctgg agatcaag                                                    318

<210> SEQ ID NO 34
<211> LENGTH: 348
<212> TYPE: DNA
<213> ORGANISM: Artificial Sequence
<220> FEATURE:
<223> OTHER INFORMATION: recombinant sequence

<400> SEQUENCE: 34
gaggtgcagc tggtgcagtc cggcgccgag gtgaagaagc ccggctcctc cgtgaaggtg      60
tcctgcaagg cctccggcta ctccttcacc tcctactaca tccactgggt gaggcaggcc     120
cccggccagt gcctggagtg gatgggcagg atcggccccg gctccggcga catcaactac     180
aacgagaagt tcaagggcag ggccaccttc accgtggaca gtccacctc caccgcctac      240 atggagctgt cctccctgag gtccgaggac accgccgtgt actactgcgc caggttccac     300
tacgacggcg ccgactgggg ccagggcacc ctggtgaccg tgtcctcc                  348

<210> SEQ ID NO 35
<211> LENGTH: 242
<212> TYPE: PRT
<213> ORGANISM: Artificial Sequence
<220> FEATURE:
<223> OTHER INFORMATION: recombinant sequence

<400> SEQUENCE: 35

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Gly Leu Glu Trp Met
        35                  40                  45

Gly Arg Ile Gly Pro Gly Ser Gly Asp Ile Asn Tyr Asn Glu Lys Phe
    50                  55                  60

Lys Gly Arg Ala Thr Phe Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe His Tyr Asp Gly Ala Asp Trp Gly Gln Gly Thr Leu Val
            100                 105                 110

Thr Val Ser Ser Gly Gly Gly Gly Ser Gly Gly Gly Gly Ser Gly Gly
```

-continued

```
              115                 120                 125
Gly Gly Ser Gly Gly Gly Ser Asp Ile Gln Met Thr Gln Ser Pro
    130                 135                 140
Ser Ser Leu Ser Ala Ser Val Gly Asp Arg Val Thr Ile Thr Cys Lys
145                 150                 155                 160
Ala Ser Gln Asn Ile Asn Glu Asn Leu Asp Trp Tyr Gln Gln Lys Pro
                165                 170                 175
Gly Lys Ala Pro Lys Leu Leu Ile Tyr Tyr Thr Asp Ile Leu Gln Thr
                180                 185                 190
Gly Ile Pro Ser Arg Phe Ser Gly Ser Gly Ser Gly Thr Asp Tyr Thr
                195                 200                 205
Leu Thr Ile Ser Ser Leu Gln Pro Glu Asp Phe Ala Thr Tyr Tyr Cys
    210                 215                 220
Tyr Gln Tyr Tyr Ser Gly Tyr Thr Phe Gly Gln Gly Thr Lys Leu Glu
225                 230                 235                 240
Ile Lys
```

```
<210> SEQ ID NO 36
<211> LENGTH: 726
<212> TYPE: DNA
<213> ORGANISM: Artificial Sequence
<220> FEATURE:
<223> OTHER INFORMATION: recombinant sequence

<400> SEQUENCE: 36
gaggtgcagc tggtgcagtc cggcgccgag gtgaagaagc ccggctcctc cgtgaaggtg      60
tcctgcaagg cctccggcta ctccttcacc tcctactaca tccactgggt gaggcaggcc     120
cccggccagg gctggagtg atgggcagg atcggcccg gctccggcga catcaactac         180
aacgagaagt tcaagggcag ggccaccttc accgtggaca agtccacctc caccgcctac     240
atggagctgt cctccctgag gtccgaggac accgccgtgt actactgcgc caggttccac     300
tacgacggcg ccgactgggg ccagggcacc ctggtgaccg tgtcctccgg aggtggcggt     360
tctggcggtg gcggttccgg tggcggtgga tcgggaggtg gcggttctga catccagatg     420
acccagtccc cctcctccct gtccgcctcc gtgggcgaca gggtgaccat cacctgcaag     480
gcctcccaga acatcaacga gaacctggac tggtaccagc agaagcccgg caaggccccc     540
aagctgctga tctactacac cgacatcctg cagaccggca tccctccag gttctccggc      600 tccggctccg gcaccgacta caccctgacc atctcctccc tgcagcccga ggacttcgcc     660
acctactact gctaccagta ctactccggc tacaccttcg gccagggcac caagctggag     720
atcaag                                                                726
```

```
<210> SEQ ID NO 37
<211> LENGTH: 242
<212> TYPE: PRT
<213> ORGANISM: Artificial Sequence
<220> FEATURE:
<223> OTHER INFORMATION: recombinant sequence

<400> SEQUENCE: 37

Glu Val Gln Leu Val Gln Ser Gly Ala Glu Val Lys Lys Pro Gly Ser
1               5                   10                  15
Ser Val Lys Val Ser Cys Lys Ala Ser Gly Tyr Ser Phe Thr Ser Tyr
                20                  25                  30
Tyr Ile His Trp Val Arg Gln Ala Pro Gly Gln Cys Leu Glu Trp Met
        35                  40                  45
```

```
Gly Arg Ile Gly Pro Gly Ser Gly Asp Ile Asn Tyr Asn Glu Lys Phe
    50                  55                  60

Lys Gly Arg Ala Thr Phe Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe His Tyr Asp Gly Ala Asp Trp Gly Gln Gly Thr Leu Val
            100                 105                 110

Thr Val Ser Ser Gly Gly Gly Ser Gly Gly Gly Ser Gly Gly
            115                 120                 125

Gly Gly Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Ile Asn Glu Asn Leu Asp Trp Tyr Gln Gln Lys Pro
                165                 170                 175

Gly Lys Ala Pro Lys Leu Leu Ile Tyr Tyr Thr Asp Ile Leu Gln Thr
            180                 185                 190

Gly Ile Pro Ser Arg Phe Ser Gly Ser Gly Ser Gly Thr Asp Tyr Thr
            195                 200                 205

Leu Thr Ile Ser Ser Leu Gln Pro Glu Asp Phe Ala Thr Tyr Tyr Cys
    210                 215                 220

Tyr Gln Tyr Tyr Ser Gly Tyr Thr Phe Gly Cys Gly Thr Lys Leu Glu
225                 230                 235                 240

Ile Lys
```

```
<210> SEQ ID NO 38
<211> LENGTH: 726
<212> TYPE: DNA
<213> ORGANISM: Artificial Sequence
<220> FEATURE:
<223> OTHER INFORMATION: recombinant sequence

<400> SEQUENCE: 38
gaggtgcagc tggtgcagtc cggcgccgag gtgaagaagc ccggctcctc cgtgaaggtg      60
tcctgcaagg cctccggcta ctccttcacc tcctactaca tccactgggt gaggcaggcc     120
cccggccagt gcctggagtg gatgggcagg atcggccccg gctccggcga catcaactac     180
aacgagaagt tcaagggcag ggccaccttc accgtggaca gtccacctc caccgcctac      240 atggagctgt cctccctgag gtccgaggac accgccgtgt actactgcgc caggttccac     300
tacgacggcg ccgactgggg ccagggcacc ctggtgaccg tgtcctccgg aggtggcggt     360
tctggcggtg gcggttccgg tggcggtgga tcgggaggtg gcggttctga catccagatg     420
acccagtccc cctcctccct gtccgcctcc gtgggcgaca gggtgaccat cacctgcaag     480
gcctcccaga acatcaacga gaacctggac tggtaccagc agaagcccgg caaggccccc     540
aagctgctga tctactacac cgacatcctg cagaccggca tcccctccag gttctccggc     600
tccggctccg gcaccgacta caccctgacc atctcctccc tgcagcccga ggacttcgcc     660
acctactact gctaccagta ctactccggc tacaccttcg gctgcggcac caagctggag     720
atcaag                                                                726
```

```
<210> SEQ ID NO 39
<211> LENGTH: 12
<212> TYPE: PRT
```

<213> ORGANISM: Artificial Sequence
<220> FEATURE:
<223> OTHER INFORMATION: recombinant sequence

<400> SEQUENCE: 39

Gln Ser Ser Pro Ser Val Trp Ser Asn Phe Leu Ser
1               5                   10

<210> SEQ ID NO 40
<211> LENGTH: 7
<212> TYPE: PRT
<213> ORGANISM: Artificial Sequence
<220> FEATURE:
<223> OTHER INFORMATION: recombinant sequence

<400> SEQUENCE: 40

Glu Ala Ser Lys Leu Thr Ser
1               5

<210> SEQ ID NO 41
<211> LENGTH: 11
<212> TYPE: PRT
<213> ORGANISM: Artificial Sequence
<220> FEATURE:
<223> OTHER INFORMATION: recombinant sequence

<400> SEQUENCE: 41

Gly Gly Gly Tyr Ser Ser Ile Ser Asp Thr Thr
1               5                   10

<210> SEQ ID NO 42
<211> LENGTH: 10
<212> TYPE: PRT
<213> ORGANISM: Artificial Sequence
<220> FEATURE:
<223> OTHER INFORMATION: recombinant sequence

<400> SEQUENCE: 42

Gly Ile Asp Leu Ser Asn Tyr Ala Ile Asn
1               5                   10

<210> SEQ ID NO 43
<211> LENGTH: 16
<212> TYPE: PRT
<213> ORGANISM: Artificial Sequence
<220> FEATURE:
<223> OTHER INFORMATION: recombinant sequence

<400> SEQUENCE: 43

Ile Ile Trp Ala Ser Gly Thr Thr Phe Tyr Ala Thr Trp Ala Lys Gly
1               5                   10                  15

<210> SEQ ID NO 44
<211> LENGTH: 13
<212> TYPE: PRT
<213> ORGANISM: Artificial Sequence
<220> FEATURE:
<223> OTHER INFORMATION: recombinant sequence

<400> SEQUENCE: 44

Thr Val Pro Gly Tyr Ser Thr Ala Pro Tyr Phe Asp Leu
1               5                   10

<210> SEQ ID NO 45
<211> LENGTH: 110
<212> TYPE: PRT
<213> ORGANISM: Artificial Sequence
<220> FEATURE:
<223> OTHER INFORMATION: recombinant sequence

<400> SEQUENCE: 45

```
Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Gly Gly Thr Lys Val Glu Ile Lys
            100                 105                 110
```

<210> SEQ ID NO 46
<211> LENGTH: 121
<212> TYPE: PRT
<213> ORGANISM: Artificial Sequence
<220> FEATURE:
<223> OTHER INFORMATION: recombinant sequence

<400> SEQUENCE: 46

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
                100                 105                 110

Gln Gly Thr Leu Val Thr Val Ser Ser
        115                 120
```

<210> SEQ ID NO 47
<211> LENGTH: 330
<212> TYPE: DNA
<213> ORGANISM: Artificial Sequence
<220> FEATURE:
<223> OTHER INFORMATION: recombinant sequence

<400> SEQUENCE: 47

```
gatattcaga tgacgcaatc accttcgagc gtatccgcct cggtgggaga cagggtgaca      60
atcacttgtc agtcatcccc ctcagtctgg agcaactttt tgtcatggta tcagcagaag     120
cccggaaagg ctccgaaatt gctgatctac gaggcatcga agttgacgag cggtgtacca     180
agcagattct ccggttcggg gtcgggaact gacttcaccc ttacgatctc atcgctgcag     240
ccggaggatt ttgcgaccta ctactgtggg ggtgggtatt cgtcgatttc cgacacaaca     300
```

```
ttcgggggcg gcacgaaagt ggaaatcaag                                    330

<210> SEQ ID NO 48
<211> LENGTH: 363
<212> TYPE: DNA
<213> ORGANISM: Artificial Sequence
<220> FEATURE:
<223> OTHER INFORMATION: recombinant sequence

<400> SEQUENCE: 48
gaagtgcagt tgctggagtc aggtggaggg ctggtgcagc ccggaggatc gctgcggttg     60
tcatgcgcgg tgtccggtat tgatttgtcc aattacgcca tcaattgggt acgccaagcg    120
ccagggaagg gccttgagtg gattggcatc atctgggcgt cggggacgac cttttatgct    180
acttgggcca aaggaagatt cacaatctcc cgagacaact cgaagaacac cgtgtatctt    240
caaatgaact cgctcagggc cgaggacacg gcggtctact actgtgcacg gacagtgccg    300
ggttattcaa cggcacctta ctttgatctt tggggccagg ggaccctcgt gactgtctca    360
agt                                                                 363

<210> SEQ ID NO 49
<211> LENGTH: 110
<212> TYPE: PRT
<213> ORGANISM: Artificial Sequence
<220> FEATURE:
<223> OTHER INFORMATION: recombinant sequence

<400> SEQUENCE: 49

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Cys Gly Thr Lys Val Glu Ile Lys
            100                 105                 110

<210> SEQ ID NO 50
<211> LENGTH: 121
<212> TYPE: PRT
<213> ORGANISM: Artificial Sequence
<220> FEATURE:
<223> OTHER INFORMATION: recombinant sequence

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60
```

Gly Arg Phe Thr Ile Ser Arg Asp Asn Ser Lys Asn Thr Val Tyr Leu
65                    70                    75                    80

Gln Met Asn Ser Leu Arg Ala Glu Asp Thr Ala Val Tyr Tyr Cys Ala
                85                    90                    95

Arg Thr Val Pro Gly Tyr Ser Thr Ala Pro Tyr Phe Asp Leu Trp Gly
            100                    105                    110

Gln Gly Thr Leu Val Thr Val Ser Ser
        115                    120

<210> SEQ ID NO 51
<211> LENGTH: 330
<212> TYPE: DNA
<213> ORGANISM: Artificial Sequence
<220> FEATURE:
<223> OTHER INFORMATION: recombinant sequence

<400> SEQUENCE: 51
gatattcaga tgacgcaatc accttcgagc gtatccgcct cggtgggaga cagggtgaca      60
atcacttgtc agtcatcccc ctcagtctgg agcaactttt tgtcatggta tcagcagaag     120
cccggaaagg ctccgaaatt gctgatctac gaggcatcga agttgacgag cggtgtacca     180
agcagattct ccggttcggg gtcgggaact gacttcaccc ttacgatctc atcgctgcag     240
ccggaggatt ttgcgaccta ctactgtggg ggtgggtatt cgtcgatttc cgacacaaca     300
ttcgggtgcg gcacgaaagt ggaaatcaag                                      330

<210> SEQ ID NO 52
<211> LENGTH: 363
<212> TYPE: DNA
<213> ORGANISM: Artificial Sequence
<220> FEATURE:
<223> OTHER INFORMATION: recombinant sequence

<400> SEQUENCE: 52
gaagtgcagt tgctggagtc aggtggaggg ctggtgcagc ccggaggatc gctgcggttg      60
tcatgcgcgg tgtccggtat tgatttgtcc aattacgcca tcaattgggt acgccaagcg     120
ccagggaagt gccttgagtg gattggcatc atctgggcgt cggggacgac cttttatgct     180
acttgggcca aaggaagatt cacaatctcc cgagacaact cgaagaacac cgtgtatctt     240
caaatgaact cgctcagggc cgaggacacg gcggtctact actgtgcacg gacagtgccg     300
ggttattcaa cggcacctta ctttgatctt tggggccagg gaccctcgt gactgtctca      360 agt                                                                    363

<210> SEQ ID NO 53
<211> LENGTH: 251
<212> TYPE: PRT
<213> ORGANISM: Artificial Sequence
<220> FEATURE:
<223> OTHER INFORMATION: recombinant sequence

<400> SEQUENCE: 53

Glu Val Gln Leu Leu Glu Ser Gly Gly Gly Leu Val Gln Pro Gly Gly
1                    5                    10                    15

Ser Leu Arg Leu Ser Cys Ala Val Ser Gly Ile Asp Leu Ser Asn Tyr
                20                    25                    30

Ala Ile Asn Trp Val Arg Gln Ala Pro Gly Lys Gly Leu Glu Trp Ile
        35                    40                    45

Gly Ile Ile Trp Ala Ser Gly Thr Thr Phe Tyr Ala Thr Trp Ala Lys

-continued

```
      50              55              60

Gly Arg Phe Thr Ile Ser Arg Asp Asn Ser Lys Asn Thr Val Tyr Leu
65              70              75              80

Gln Met Asn Ser Leu Arg Ala Glu Asp Thr Ala Val Tyr Tyr Cys Ala
                85              90              95

Arg Thr Val Pro Gly Tyr Ser Thr Ala Pro Tyr Phe Asp Leu Trp Gly
            100             105             110

Gln Gly Thr Leu Val Thr Val Ser Ser Gly Gly Gly Ser Gly Gly
        115             120             125

Gly Gly Ser Gly Gly Gly Gly Ser Gly Gly Gly Gly Ser Asp Ile Gln
        130             135             140

Met Thr Gln Ser Pro Ser Ser Val Ser Ala Ser Val Gly Asp Arg Val
145             150             155             160

Thr Ile Thr Cys Gln Ser Ser Pro Ser Val Trp Ser Asn Phe Leu Ser
                165             170             175

Trp Tyr Gln Gln Lys Pro Gly Lys Ala Pro Lys Leu Leu Ile Tyr Glu
                180             185             190

Ala Ser Lys Leu Thr Ser Gly Val Pro Ser Arg Phe Ser Gly Ser Gly
                195             200             205

Ser Gly Thr Asp Phe Thr Leu Thr Ile Ser Ser Leu Gln Pro Glu Asp
        210             215             220

Phe Ala Thr Tyr Tyr Cys Gly Gly Gly Tyr Ser Ser Ile Ser Asp Thr
225             230             235             240

Thr Phe Gly Gly Gly Thr Lys Val Glu Ile Lys
                245             250
```

```
<210> SEQ ID NO 54
<211> LENGTH: 753
<212> TYPE: DNA
<213> ORGANISM: Artificial Sequence
<220> FEATURE:
<223> OTHER INFORMATION: recombinant sequence

<400> SEQUENCE: 54
gaagtgcagt tgctggagtc aggtggaggg ctggtgcagc ccggaggatc gctgcggttg      60
tcatgcgcgg tgtccggtat tgatttgtcc aattacgcca tcaattgggt acgccaagcg     120
ccagggaagg gccttgagtg gattggcatc atctgggcgt cggggacgac cttttatgct     180
acttgggcca aaggaagatt cacaatctcc cgagacaact cgaagaacac cgtgtatctt     240
caaatgaact cgctcagggc cgaggacacg gcggtctact actgtgcacg gacagtgccg     300
ggttattcaa cggcacctta ctttgatctt tggggccagg gaccctcgt gactgtctca      360 agtggaggtg gcggttctgg cggtggcggt tccggtggcg gtggatcggg aggtggcggt     420
tctgatattc agatgacgca atcaccttcg agcgtatccg cctcggtggg agacagggtg     480
acaatcactt gtcagtcatc cccctcagtc tggagcaact tttgtcatg gtatcagcag      540 aagcccggaa aggctccgaa attgctgatc tacgaggcat cgaagttgac gagcggtgta     600
ccaagcagat tctccggttc ggggtcggga actgacttca cccttacgat ctcatcgctg     660 cagccgagg attttgcgac ctactactgt ggggtgggt attcgtcgat ttccgacaca      720
acattcgggg gcggcacgaa agtggaaatc aag                                  753

<210> SEQ ID NO 55
<211> LENGTH: 251
<212> TYPE: PRT
<213> ORGANISM: Artificial Sequence
```

```
<220> FEATURE:
<223> OTHER INFORMATION: recombinant sequence

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Val Ser Ala Ser Val Gly Asp Arg Val
145                 150                 155                 160

Thr Ile Thr Cys Gln Ser Ser Pro Ser Val Trp Ser Asn Phe Leu Ser
                165                 170                 175

Trp Tyr Gln Gln Lys Pro Gly Lys Ala Pro Lys Leu Leu Ile Tyr Glu
                180                 185                 190

Ala Ser Lys Leu Thr Ser Gly Val Pro Ser Arg Phe Ser Gly Ser Gly
                195                 200                 205

Ser Gly Thr Asp Phe Thr Leu Thr Ile Ser Ser Leu Gln Pro Glu Asp
    210                 215                 220

Phe Ala Thr Tyr Tyr Cys Gly Gly Gly Tyr Ser Ser Ile Ser Asp Thr
225                 230                 235                 240

Thr Phe Gly Cys Gly Thr Lys Val Glu Ile Lys
                245                 250

<210> SEQ ID NO 56
<211> LENGTH: 753
<212> TYPE: DNA
<213> ORGANISM: Artificial Sequence
<220> FEATURE:
<223> OTHER INFORMATION: recombinant sequence

<400> SEQUENCE: 56
gaagtgcagt tgctggagtc aggtggaggg ctggtgcagc ccggaggatc gctgcggttg      60
tcatgcgcgg tgtccggtat tgatttgtcc aattacgcca tcaattgggt acgccaagcg     120
ccagggaagt gccttgagtg gattggcatc atctgggcgt cggggacgac cttttatgct     180
acttgggcca aaggaagatt cacaatctcc cgagacaact cgaagaacac cgtgtatctt     240
caaatgaact cgctcagggc cgaggacacg gcggtctact actgtgcacg gacagtgccg     300
ggttattcaa cggcacctta ctttgatctt tggggccagg gaccctcgt gactgtctca      360 agtggaggtg gcggttctgg cggtggcggt ccggtggcg gtggatcggg aggtggcggt      420
tctgatattc agatgacgca atcaccttcg agcgtatccg cctcggtggg agacagggtg     480
```

-continued

```
acaatcactt gtcagtcatc cccctcagtc tggagcaact ttttgtcatg gtatcagcag        540
aagcccggaa aggctccgaa attgctgatc tacgaggcat cgaagttgac gagcggtgta        600
ccaagcagat tctccggttc ggggtcggga actgacttca cccttacgat ctcatcgctg        660
cagccggagg attttgcgac ctactactgt gggggtgggt attcgtcgat ttccgacaca        720
acattcgggt gcggcacgaa agtggaaatc aag                                     753
```

```
<210> SEQ ID NO 57
<211> LENGTH: 492
<212> TYPE: PRT
<213> ORGANISM: Artificial Sequence
<220> FEATURE:
<223> OTHER INFORMATION: recombinant sequence

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asn Met Ala Trp Val Arg Gln Ala Pro Gly Lys Gly Leu Glu Trp Val
        35                  40                  45

Ala Thr Ile Thr Tyr Glu Gly Arg Asn Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gln Tyr Tyr Glu Gly Ser Ile Tyr Arg Leu Trp Phe
            100                 105                 110

Ala His Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
        210                 215                 220

Pro Lys Ser Cys Ser Gly Gly Gly Thr Gly Gly Gly Gly Ser Glu
225                 230                 235                 240

Val Gln Leu Leu Glu Ser Gly Gly Gly Leu Val Gln Pro Gly Gly Ser
            245                 250                 255

Leu Arg Leu Ser Cys Ala Val Ser Gly Ile Asp Leu Ser Asn Tyr Ala
            260                 265                 270

Ile Asn Trp Val Arg Gln Ala Pro Gly Lys Gly Leu Glu Trp Ile Gly
        275                 280                 285

Ile Ile Trp Ala Ser Gly Thr Thr Phe Tyr Ala Thr Trp Ala Lys Gly
    290                 295                 300

Arg Phe Thr Ile Ser Arg Asp Asn Ser Lys Asn Thr Val Tyr Leu Gln
305                 310                 315                 320
```

```
Met Asn Ser Leu Arg Ala Glu Asp Thr Ala Val Tyr Tyr Cys Ala Arg
             325                 330                 335

Thr Val Pro Gly Tyr Ser Thr Ala Pro Tyr Phe Asp Leu Trp Gly Gln
             340                 345                 350

Gly Thr Leu Val Thr Val Ser Ser Gly Gly Gly Gly Ser Gly Gly Gly
             355                 360                 365

Gly Ser Gly Gly Gly Gly Ser Gly Gly Gly Ser Asp Ile Gln Met
     370                 375                 380

Thr Gln Ser Pro Ser Ser Val Ser Ala Ser Val Gly Asp Arg Val Thr
385                 390                 395                 400

Ile Thr Cys Gln Ser Ser Pro Ser Val Trp Ser Asn Phe Leu Ser Trp
                 405                 410                 415

Tyr Gln Gln Lys Pro Gly Lys Ala Pro Lys Leu Leu Ile Tyr Glu Ala
             420                 425                 430

Ser Lys Leu Thr Ser Gly Val Pro Ser Arg Phe Ser Gly Ser Gly Ser
             435                 440                 445

Gly Thr Asp Phe Thr Leu Thr Ile Ser Ser Leu Gln Pro Glu Asp Phe
     450                 455                 460

Ala Thr Tyr Tyr Cys Gly Gly Gly Tyr Ser Ser Ile Ser Asp Thr Thr
465                 470                 475                 480

Phe Gly Gly Gly Thr Lys Val Glu Ile Lys Arg Thr
                 485                 490
```

<210> SEQ ID NO 58
<211> LENGTH: 1476
<212> TYPE: DNA
<213> ORGANISM: Artificial Sequence
<220> FEATURE:
<223> OTHER INFORMATION: recombinant sequence

<400> SEQUENCE: 58

```
gaagttcagc tggtcgagtc tggaggtggc cttgtccaac ctggagggag cctgcgtctc     60
tcttgtgcag caagcggatt cacgttttct gattacaata tggcttgggt tagacaggca    120
ccgggtaagg gccttgaatg ggttgcgacg attacatacg aaggcagaaa tacctattac    180
agggactcag taaaagggcg gtttaccata agccgagata atgctaaaaa cagtctgtat    240
ttgcaaatga acagcctacg agctgaagac actgccgtgt attactgcgc gagtccacct    300
cagtattatg aaggatcaat ctatcgcctc tggttcgcac attggggaca ggggacccct    360
gtgacagtct cgagtgcgtc cacaaagggc ccatcggtct tccccctggc accctcctcc    420
aagagcacct ctgggggcac agcggccctg ggctgcctgg tcaaggacta cttccccgaa    480
ccagtgacgg tgtcgtggaa ctcaggtgcc ctgaccagcg gcgttcacac cttcccggct    540
gtcctacagt cttcaggact ctactccctg agcagcgtgg tgaccgtgcc ctccagcagc    600
ttgggcaccc agacctacat ctgcaacgtg aatcacaagc ccagcaacac caaggtcgat    660
aagaaagttg agcccaaatc ttgtagcggt ggcggtggca ccggaggtgg cggttcagaa    720
gtgcagttgc tggagtcagg tggagggctg gtgcagcccg gaggatcgct gcggttgtca    780
tgcgcggtgt ccggtattga tttgtccaat tacgccatca attgggtacg ccaagcgcca    840
gggaagggcc ttgagtggat tggcatcatc tgggcgtcgg gacgaccttt ttatgctact    900
tgggccaaag gaagattcac aatctcccga caactcgatg agaacaccgt gtatcttcaa    960
atgaactcgc tcaggcccga ggacacggcg gtctactact gtgcacggac agtgccgggt   1020
tattcaacgg caccttactt tgatctttgg ggccagggga ccctcgtgac tgtctcaagt   1080
```

-continued

```
ggaggtggcg gttctggcgg tggcggttcc ggtggcggtg gatcgggagg tggcggttct    1140
gatattcaga tgacgcaatc accttcgagc gtatccgcct cggtgggaga cagggtgaca    1200
atcacttgtc agtcatcccc ctcagtctgg agcaacttt tgtcatggta tcagcagaag     1260
cccggaaagg ctccgaaatt gctgatctac gaggcatcga agttgacgag cggtgtacca    1320
agcagattct ccggttcggg gtcgggaact gacttcaccc ttacgatctc atcgctgcag    1380
ccggaggatt ttgcgaccta ctactgtggg ggtgggtatt cgtcgatttc cgacacaaca    1440 ttcggggggcg gcacgaaagt ggaaatcaag cgtacc                             1476
```

<210> SEQ ID NO 59
<211> LENGTH: 492
<212> TYPE: PRT
<213> ORGANISM: Artificial Sequence
<220> FEATURE:
<223> OTHER INFORMATION: recombinant sequence

<400> SEQUENCE: 59

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asn Met Ala Trp Val Arg Gln Ala Pro Gly Lys Gly Leu Glu Trp Val
        35                  40                  45

Ala Thr Ile Thr Tyr Glu Gly Arg Asn Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gln Tyr Tyr Glu Gly Ser Ile Tyr Arg Leu Trp Phe
            100                 105                 110

Ala His Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
        210                 215                 220

Pro Lys Ser Cys Ser Gly Gly Gly Gly Thr Gly Gly Gly Gly Ser Glu
225                 230                 235                 240

Val Gln Leu Leu Glu Ser Gly Gly Gly Leu Val Gln Pro Gly Gly Ser
                245                 250                 255

Leu Arg Leu Ser Cys Ala Val Ser Gly Ile Asp Leu Ser Asn Tyr Ala
            260                 265                 270

Ile Asn Trp Val Arg Gln Ala Pro Gly Lys Cys Leu Glu Trp Ile Gly
        275                 280                 285
```

```
Ile Ile Trp Ala Ser Gly Thr Thr Phe Tyr Ala Thr Trp Ala Lys Gly
    290                 295                 300

Arg Phe Thr Ile Ser Arg Asp Asn Ser Lys Asn Thr Val Tyr Leu Gln
305                 310                 315                 320

Met Asn Ser Leu Arg Ala Glu Asp Thr Ala Val Tyr Tyr Cys Ala Arg
                325                 330                 335

Thr Val Pro Gly Tyr Ser Thr Ala Pro Tyr Phe Asp Leu Trp Gly Gln
            340                 345                 350

Gly Thr Leu Val Thr Val Ser Ser Gly Gly Gly Ser Gly Gly Gly
            355                 360                 365

Gly Ser Gly Gly Gly Gly Ser Gly Gly Gly Gly Ser Asp Ile Gln Met
    370                 375                 380

Thr Gln Ser Pro Ser Ser Val Ser Ala Ser Val Gly Asp Arg Val Thr
385                 390                 395                 400

Ile Thr Cys Gln Ser Ser Pro Ser Val Trp Ser Asn Phe Leu Ser Trp
                405                 410                 415

Tyr Gln Gln Lys Pro Gly Lys Ala Pro Lys Leu Leu Ile Tyr Glu Ala
                420                 425                 430

Ser Lys Leu Thr Ser Gly Val Pro Ser Arg Phe Ser Gly Ser Gly Ser
            435                 440                 445

Gly Thr Asp Phe Thr Leu Thr Ile Ser Ser Leu Gln Pro Glu Asp Phe
    450                 455                 460

Ala Thr Tyr Tyr Cys Gly Gly Gly Tyr Ser Ser Ile Ser Asp Thr Thr
465                 470                 475                 480

Phe Gly Cys Gly Thr Lys Val Glu Ile Lys Arg Thr
                485                 490
```

```
<210> SEQ ID NO 60
<211> LENGTH: 1476
<212> TYPE: DNA
<213> ORGANISM: Artificial Sequence
<220> FEATURE:
<223> OTHER INFORMATION: recombinant sequence

<400> SEQUENCE: 60
gaagttcagc tggtcgagtc tggaggtggc cttgtccaac ctggagggag cctgcgtctc      60
tcttgtgcag caagcggatt cacgtttttct gattacaata tggcttgggt tagacaggca     120
ccgggtaagg gccttgaatg ggttgcgacg attacatacg aaggcagaaa tacctattac     180
agggactcag taaaagggcg gtttaccata agccgagata atgctaaaaa cagtctgtat     240
ttgcaaatga acagcctacg agctgaagac actgccgtgt attactgcgc gagtccacct     300
cagtattatg aaggatcaat ctatcgcctc tggttcgcac attggggaca ggggacccttt     360 gtgacagtct cgagtgcgtc cacaaagggc ccatcggtct tccccctggc accctcctcc     420
aagagcacct ctgggggcac agcggccctg ggctgcctgg tcaaggacta cttccccgaa     480
ccagtgacgg tgtcgtggaa ctcaggtgcc ctgaccagcg gcgttcacac cttcccggct     540
gtcctacagt cttcaggact ctactccctg agcagcgtgg tgaccgtgcc ctccagcagc     600
ttgggcaccc agacctacat ctgcaacgtg aatcacaagc ccagcaacac caaggtcgat     660
aagaaagttg agcccaaatc ttgtagcggt ggcggtggca ccgagggtgg cggttcagaa     720
gtgcagttgc tggagtcagg tggagggctg gtgcagcccg gaggatcgct gcggttgtca     780
tgcgcggtgt ccggtattga tttgtccaat tacgccatca attgggtacg ccaagcgcca     840
gggaagtgcc ttgagtggat tggcatcatc tgggcgtcgg gacgacctt ttatgctact     900
```

-continued

```
tgggccaaag gaagattcac aatctcccga gacaactcga agaacaccgt gtatcttcaa      960
atgaactcgc tcagggccga ggacacggcg gtctactact gtgcacggac agtgccgggt     1020
tattcaacgg cacct tactt tgatctttgg ggccagggga ccctcgtgac tgtctcaagt    1080
ggaggtggcg gttctggcgg tggcggttcc ggtggcggtg gatcgggagg tggcggttct     1140
gatattcaga tgacgcaatc accttcgagc gtatccgcct cggtgggaga cagggtgaca     1200
atcacttgtc agtcatcccc ctcagtctgg agcaactttt tgtcatggta tcagcagaag     1260
cccggaaagg ctccgaaatt gctgatctac gaggcatcga agttgacgag cggtgtacca     1320
agcagattct ccggttcggg gtcgggaact gacttcaccc ttacgatctc atcgctgcag     1380
ccggaggatt ttgcgaccta ctactgtggg ggtgggtatt cgtcgatttc cgacacaaca     1440
ttcgggtgcg gcacgaaagt ggaaatcaag cgtacc                              1476
```

```
<210> SEQ ID NO 61
<211> LENGTH: 469
<212> TYPE: PRT
<213> ORGANISM: Artificial Sequence
<220> FEATURE:
<223> OTHER INFORMATION: recombinant sequence

<400> SEQUENCE: 61

Ala Ile Gln Leu Thr Gln Ser Pro Ser Ser Leu Ser Ala Ser Val Gly
1               5                   10                  15

Asp Arg Val Thr Ile Thr Cys Arg Ala Asp Glu Ser Val Arg Thr Leu
                20                  25                  30

Met His Trp Tyr Gln Gln Lys Pro Gly Lys Ala Pro Lys Leu Leu Ile
            35                  40                  45

Tyr Leu Val Ser Asn Ser Glu Ile Gly Val Pro Asp Arg Phe Ser Gly
        50                  55                  60

Ser Gly Ser Gly Thr Asp Phe Arg Leu Thr Ile Ser Ser Leu Gln Pro
65                  70                  75                  80

Glu Asp Phe Ala Thr Tyr Tyr Cys Gln Gln Thr Trp Ser Asp Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Ser Gly Gly Gly Ser Gly Gly Gly Gly
        210                 215                 220

Ser Glu Val Gln Leu Val Gln Ser Gly Ala Glu Val Lys Lys Pro Gly
225                 230                 235                 240

Ser Ser Val Lys Val Ser Cys Lys Ala Ser Gly Tyr Ser Phe Thr Ser
                245                 250                 255

Tyr Tyr Ile His Trp Val Arg Gln Ala Pro Gly Gln Gly Leu Glu Trp
```

-continued

```
                    260              265                270

Met Gly Arg Ile Gly Pro Gly Ser Gly Asp Ile Asn Tyr Asn Glu Lys
                275              280                285

Phe Lys Gly Arg Ala Thr Phe Thr Val Asp Lys Ser Thr Ser Thr Ala
        290              295              300

Tyr Met Glu Leu Ser Ser Leu Arg Ser Glu Asp Thr Ala Val Tyr Tyr
305              310              315                320

Cys Ala Arg Phe His Tyr Asp Gly Ala Asp Trp Gly Gln Gly Thr Leu
            325              330              335

Val Thr Val Ser Ser Gly Gly Gly Ser Gly Gly Gly Gly Ser Gly
            340              345              350

Gly Gly Gly Ser Gly Gly Gly Gly Ser Asp Ile Gln Met Thr Gln Ser
            355              360              365

Pro Ser Ser Leu Ser Ala Ser Val Gly Asp Arg Val Thr Ile Thr Cys
        370              375              380

Lys Ala Ser Gln Asn Ile Asn Glu Asn Leu Asp Trp Tyr Gln Gln Lys
385              390              395                400

Pro Gly Lys Ala Pro Lys Leu Leu Ile Tyr Tyr Thr Asp Ile Leu Gln
            405              410              415

Thr Gly Ile Pro Ser Arg Phe Ser Gly Ser Gly Ser Gly Thr Asp Tyr
            420              425              430

Thr Leu Thr Ile Ser Ser Leu Gln Pro Glu Asp Phe Ala Thr Tyr Tyr
            435              440              445

Cys Tyr Gln Tyr Tyr Ser Gly Tyr Thr Phe Gly Gln Gly Thr Lys Leu
    450              455              460

Glu Ile Lys Arg Thr
465
```

```
<210> SEQ ID NO 62
<211> LENGTH: 1407
<212> TYPE: DNA
<213> ORGANISM: Artificial Sequence
<220> FEATURE:
<223> OTHER INFORMATION: recombinant sequence

<400> SEQUENCE: 62
gcaatccagc tcacccagag tccaagcagt ctctccgcca gcgtaggcga ccgtgtgact      60
attacctgta gagcggacga gtcggtcagg actctcatgc actggtatca acagaagcct     120
ggtaaagctc ctaaactgct catctatctg gtgtccaact cggagatagg tgtgccagat     180
cggtttagtg ggtctggttc aggcactgat ttcagactga ccatatcatc tctacagcca     240
gaggacttcg ccacatatta ctgtcagcaa acctggagtg acccgtggac tttcggccag     300
ggcactaaag tagaaattaa acgtacggtg gccgctccct ccgtgttcat cttcccaccc     360
tccgacgagc agctgaagtc cggcaccgcc tccgtcgtgt gcctgctgaa caacttctac     420
ccccgcgagg ccaaggtgca gtggaaggtg gacaacgccc tgcagtccgg caactcccag     480
gaatccgtca ccgagcagga ctccaaggac agcacctact ccctgtcctc caccctgacc     540
ctgtccaagg ccgactacga gaagcacaag gtgtacgcct gcgaagtgac ccaccagggc     600
ctgtccagcc ccgtgaccaa gtccttcaac cggggcgagt gcagcggtgg cggtggctcc     660
ggaggtggcg gttcagaggt gcagctggtg cagtccggcg ccgaggtgaa gaagcccggc     720
tcctccgtga aggtgtcctg caaggcctcc ggctactcct tcacctccta ctacatccac     780
tgggtgaggc aggcccccgg ccagggcctg gagtggatgg gcaggatcgg ccccggctcc     840
```

-continued

```
ggcgacatca actacaacga gaagttcaag ggcagggcca ccttcaccgt ggacaagtcc      900
acctccaccg cctacatgga gctgtcctcc ctgaggtccg aggacaccgc cgtgtactac      960
tgcgccaggt tccactacga cggcgccgac tggggccagg gcaccctggt gaccgtgtcc     1020 tccgaggtg gcggttctgg cggtggcggt tccggtggcg gtggatcggg aggtggcggt     1080
tctgacatcc agatgaccca gtcccctcc tccctgtccg cctccgtggg cgacagggtg     1140
accatcacct gcaaggcctc ccagaacatc aacgagaacc tggactggta ccagcagaag     1200
cccggcaagg cccccaagct gctgatctac tacaccgaca tcctgcagac cggcatcccc     1260
tccaggttct ccggctccgg ctccggcacc gactacaccc tgaccatctc ctccctgcag     1320
cccgaggact tcgccaccta ctactgctac cagtactact ccggctacac cttcggccag     1380
ggcaccaagc tggagatcaa gcgtacc                                        1407
```

<210> SEQ ID NO 63
<211> LENGTH: 469
<212> TYPE: PRT
<213> ORGANISM: Artificial Sequence
<220> FEATURE:
<223> OTHER INFORMATION: recombinant sequence

<400> SEQUENCE: 63

```
Ala Ile Gln Leu Thr Gln Ser Pro Ser Ser Leu Ser Ala Ser Val Gly
1               5                   10                  15

Asp Arg Val Thr Ile Thr Cys Arg Ala Asp Glu Ser Val Arg Thr Leu
            20                  25                  30

Met His Trp Tyr Gln Gln Lys Pro Gly Lys Ala Pro Lys Leu Leu Ile
        35                  40                  45

Tyr Leu Val Ser Asn Ser Glu Ile Gly Val Pro Asp Arg Phe Ser Gly
    50                  55                  60

Ser Gly Ser Gly Thr Asp Phe Arg Leu Thr Ile Ser Ser Leu Gln Pro
65                  70                  75                  80

Glu Asp Phe Ala Thr Tyr Tyr Cys Gln Gln Thr Trp Ser Asp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ser Gly Gly Gly Ser Gly Gly Gly Gly
    210                 215                 220

Ser Glu Val Gln Leu Val Gln Ser Gly Ala Glu Val Lys Lys Pro Gly
225                 230                 235                 240

Ser Ser Val Lys Val Ser Cys Lys Ala Ser Gly Tyr Ser Phe Thr Ser
                245                 250                 255

Tyr Tyr Ile His Trp Val Arg Gln Ala Pro Gly Gln Cys Leu Glu Trp
```

```
                 260                 265                 270
Met Gly Arg Ile Gly Pro Gly Ser Gly Asp Ile Asn Tyr Asn Glu Lys
             275                 280                 285

Phe Lys Gly Arg Ala Thr Phe Thr Val Asp Lys Ser Thr Ser Thr Ala
         290                 295                 300

Tyr Met Glu Leu Ser Ser Leu Arg Ser Glu Asp Thr Ala Val Tyr Tyr
305                 310                 315                 320

Cys Ala Arg Phe His Tyr Asp Gly Ala Asp Trp Gly Gln Gly Thr Leu
             325                 330                 335

Val Thr Val Ser Ser Gly Gly Gly Ser Gly Gly Gly Gly Ser Gly
             340                 345                 350

Gly Gly Gly Ser Gly Gly Gly Gly Ser Asp Ile Gln Met Thr Gln Ser
         355                 360                 365

Pro Ser Ser Leu Ser Ala Ser Val Gly Asp Arg Val Thr Ile Thr Cys
     370                 375                 380

Lys Ala Ser Gln Asn Ile Asn Glu Asn Leu Asp Trp Tyr Gln Gln Lys
385                 390                 395                 400

Pro Gly Lys Ala Pro Lys Leu Leu Ile Tyr Tyr Thr Asp Ile Leu Gln
             405                 410                 415

Thr Gly Ile Pro Ser Arg Phe Ser Gly Ser Gly Ser Gly Thr Asp Tyr
             420                 425                 430

Thr Leu Thr Ile Ser Ser Leu Gln Pro Glu Asp Phe Ala Thr Tyr Tyr
             435                 440                 445

Cys Tyr Gln Tyr Tyr Ser Gly Tyr Thr Phe Gly Cys Gly Thr Lys Leu
     450                 455                 460

Glu Ile Lys Arg Thr
465
```

```
<210> SEQ ID NO 64
<211> LENGTH: 1407
<212> TYPE: DNA
<213> ORGANISM: Artificial Sequence
<220> FEATURE:
<223> OTHER INFORMATION: recombinant sequence

<400> SEQUENCE: 64
gcaatccagc tcacccagag tccaagcagt ctctccgcca gcgtaggcga ccgtgtgact      60
attacctgta gagcggacga gtcggtcagg actctcatgc actggtatca acagaagcct     120
ggtaaagctc ctaaactgct catctatctg gtgtccaact cggagatagg tgtgccagat     180
cggtttagtg ggtctggttc aggcactgat ttcagactga ccatatcatc tctacagcca     240
gaggacttcg ccacatatta ctgtcagcaa acctggagtg acccgtggac tttcggccag     300
ggcactaaag tagaaattaa acgtacggtg gccgctccct ccgtgttcat cttcccaccc     360
tccgacgagc agctgaagtc cggcaccgcc tccgtcgtgt gcctgctgaa caacttctac     420
ccccgcgagg ccaaggtgca gtggaaggtg gacaacgccc tgcagtccgg caactcccag     480
gaatccgtca ccgagcagga ctccaaggac agcacctact ccctgtcctc caccctgacc     540
ctgtccaagg ccgactacga gaagcacaag gtgtacgcct gcgaagtgac ccaccagggc     600
ctgtccagcc ccgtgaccaa gtccttcaac cggggcgagt gcagcggtgg cggtggctcc     660
ggaggtggcg gttcagaggt gcagctggtg cagtccggcg ccgaggtgaa gaagcccggc     720
tcctccgtga aggtgtcctg caaggcctcc ggctactcct tcacctccta ctacatccac     780
tgggtgaggc aggcccccgg ccagtgcctg gagtggatgg gcaggatcgg ccccggctcc     840
```

```
ggcgacatca actacaacga gaagttcaag ggcagggcca ccttcaccgt ggacaagtcc      900
acctccaccg cctacatgga gctgtcctcc ctgaggtccg aggacaccgc cgtgtactac      960
tgcgccaggt tccactacga cggcgccgac tggggccagg gcaccctggt gaccgtgtcc     1020
tccggaggtg gcggttctgg cggtggcggt tccggtggcg gtggatcggg aggtggcggt     1080
tctgacatcc agatgaccca gtccccctcc tccctgtccg cctccgtggg cgacagggtg     1140
accatcacct gcaaggcctc ccagaacatc aacgagaacc tggactggta ccagcagaag     1200
cccggcaagg cccccaagct gctgatctac tacaccgaca tcctgcagac cggcatcccc     1260
tccaggttct ccggctccgg ctccggcacc gactacaccc tgaccatctc ctccctgcag     1320
cccgaggact cgccaccta ctactgctac cagtactact ccggctacac cttcggctgc      1380
ggcaccaagc tggagatcaa gcgtacc                                        1407
```

```
<210> SEQ ID NO 65
<211> LENGTH: 11
<212> TYPE: PRT
<213> ORGANISM: Artificial Sequence
<220> FEATURE:
<223> OTHER INFORMATION: recombinant sequence

<400> SEQUENCE: 65

Ser Gly Gly Gly Gly Ser Gly Gly Gly Gly Ser
1               5                   10

<210> SEQ ID NO 66
<211> LENGTH: 20
<212> TYPE: PRT
<213> ORGANISM: Artificial Sequence
<220> FEATURE:
<223> OTHER INFORMATION: recombinant sequence

<400> SEQUENCE: 66

Gly Gly Gly Gly Ser Gly Gly Gly Gly Ser Gly Gly Gly Gly Ser Gly
1               5                   10                  15

Gly Gly Gly Ser
            20

<210> SEQ ID NO 67
<211> LENGTH: 11
<212> TYPE: PRT
<213> ORGANISM: Artificial Sequence
<220> FEATURE:
<223> OTHER INFORMATION: recombinant sequence

<400> SEQUENCE: 67

Ser Gly Gly Gly Gly Thr Gly Gly Gly Gly Ser
1               5                   10

<210> SEQ ID NO 68
<211> LENGTH: 20
<212> TYPE: PRT
<213> ORGANISM: Artificial Sequence
<220> FEATURE:
<223> OTHER INFORMATION: recombinant sequence

<400> SEQUENCE: 68

Gly Gly Gly Gly Ser Gly Gly Gly Gly Ser Gly Gly Gly Gly Ser Gly
1               5                   10                  15

Gly Gly Gly Ser
            20
```

MULTI-SPECIFIC ANTIBODY WITH BINDING SPECIFICITY FOR HUMAN IL-13 AND IL-17

CROSS REFERENCE TO RELATED APPLICATIONS

This application is a U.S. National Stage of International Application No. PCT/EP2020/087046, filed Dec. 18, 2020, which claims priority to Great Britain Application No. 1919061.0, filed Dec. 20, 2019, the entire contents of each of which are fully incorporated herein by reference.

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "57986_Seqlisting.txt." The Sequence Listing was created on Jun. 8, 2022, and is 71,813 bytes in size. The subject matter of the Sequence Listing is incorporated by reference herein in its entirety.

FIELD OF THE INVENTION

The present invention relates to a multi-specific antibody having specificity for human IL-13, human IL-17A and/or IL-17F. The invention further relates to methods for producing the multi-specific antibody and to its therapeutic use for the treatment of atopic dermatitis and other diseases.

BACKGROUND OF THE INVENTION

Atopic dermatitis (AD), also known as atopic eczema, is an inflammatory disease which results in intensely itchy, red, swollen, weeping and cracked skin which often thickens over time.

Since the beginning of the twentieth century, many mucosal inflammatory disorders have become more common; atopic dermatitis is a classic example of such a disease. It now affects 15-30% of children and 2-10% of adults in developed countries and in the United States has nearly tripled in the past thirty to forty years. Over 15 million American adults and children have atopic dermatitis.

Treatments used for AD include systemic immunosuppressants such as cyclosporin, methotrexate, interferon gamma, mycophenolate, mofetil and azathioprine. Antidepressants and naltrexone may be used to control pruritus (itchiness). In 2016, crisaborole, a phosphodiesterase-4 inhibitor, was approved for mild-to-moderate eczema, and in 2017, dupilumab, a monoclonal antibody antagonist of IL-4Ra was approved to treat moderate-to-severe eczema. Because of the limitations of the existing medications, there is a great need for improved treatment of atopic dermatitis.

WO2013/102042A2 (Abbvie) describes dual specific binding proteins directed against IL-13 and IL-17 and their potential use in treatment of an extensive list of diseases. The binding proteins did not progress into clinical development.

WO2015/127405A2 (Genentech) describes anti-IL-13/IL-17 bispecific antibodies, and methods of using them for treating moderate to severe asthma and/or eosinophilic asthma. In a phase I clinical trial, BITS7201A was associated with a high incidence of anti-drug antibodies (ADAs) and was withdrawn from clinical development.

SUMMARY OF THE INVENTION

The present invention provides an improved multi-specific antibody capable of binding human IL-13, human IL-17A and/or human IL-17F.

The antibodies of the present invention have improved properties in comparison with currently available antibodies, for example lower immunogenicity and/or better pharmacokinetic profiles. In addition, the antibodies of the present invention may be engineered so that they can be more efficiently purified using an improved purification method which comprises fewer steps than currently available methods, which is cost and time effective at the industrial scale. The antibodies of the present invention may therefore have improved manufacturability.

The invention further provides:

An isolated polynucleotide encoding the multi-specific antibody.

An expression vector carrying the polynucleotide.

A host cell comprising the vector.

A method of producing the multi-specific antibody comprising culturing the host cell and recovering the antibody produced.

A pharmaceutical composition comprising the multi-specific antibody.

A multi-specific antibody or pharmaceutical composition for use in a method of treatment of the human or animal body by therapy.

A method of treating or preventing atopic dermatitis, chronic hand eczema, nasal micropolyposis or polyposis, food allergy, or eosinophilic esophagitis, comprising administering a therapeutically effective amount of the multi-specific antibody or the pharmaceutical composition to a patient in need thereof.

BRIEF DESCRIPTION OF THE FIGURES

FIG. 1.

Figure 7:
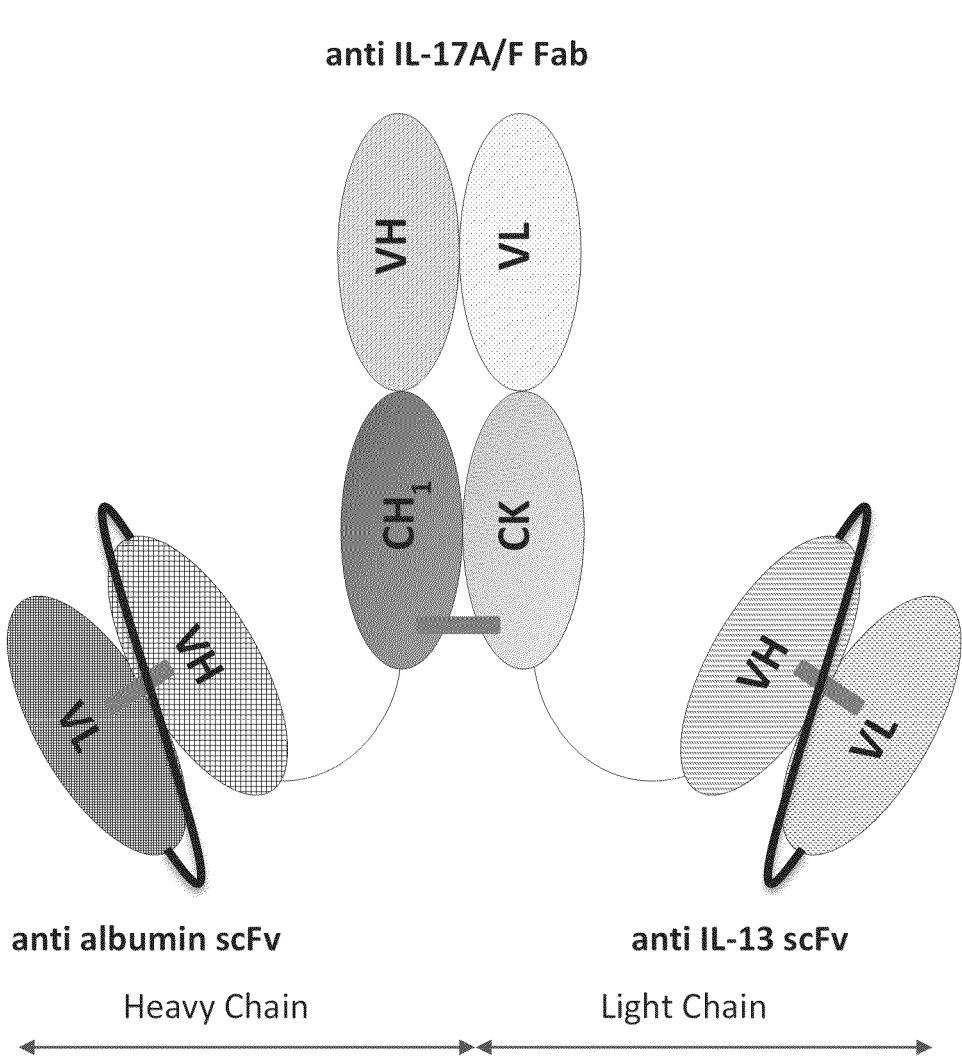

Ab650 humanisation alignments.

Alignments of the rat antibody (donor) V-region sequences with the human germline (acceptor) V-region sequences, together with the designed humanised sequences.

(A) Light chain graft 650:

650=rat variable light chain sequence.

650 gL8=humanised graft of 650 variable light chain using IGKV1-39 human germline as the acceptor framework.

CDRs are shown in bold/underlined.

Donor residues are shown in bold/italic and are highlighted: I58 and Y71.

"Light 650" corresponds to SEQ ID NO: 21; "IGKV1-39" corresponds to SEQ ID NO: 25; and "650 gL8" corresponds to SEQ ID NO: 27.

(B) Heavy Chain Graft 650:

650=rat variable heavy chain sequence.

650gH9=humanised graft of 650 variable heavy chain using IGHV1-69 human germline as the acceptor framework.

CDRs are shown in bold/underlined.

Donor residues are shown in bold/italic and are highlighted: A67, F69 and V71. "Heavy 650" corresponds to SEQ ID NO: 23; "IGHV1-69" corresponds to SEQ ID NO: 26; and "650gH9" corresponds to SEQ ID NO: 28.

FIG. 2.

Amino acid and DNA sequences.

FIG. 3.

Purification of an IL-13/IL-17AF multi-specific antibody.

(A) BEH200 SEC-UPLC analysis of purified multi-specific antibody, detection by FLR.

(B) Protein samples separated by Tris-glycine SDS-PAGE under non-reducing (lane 1) or reducing (lane 2) conditions. The gel was stained with Coomassie quick stain and destained in dH2O. Mark 12 protein markers (Life Technologies) were used as standards (M). Molecular weights (MW) were measured in kilo daltons (kDa).

FIG. 4.

Inhibition of STAT6 signalling by IL-13/IL-17AF multi-specific antibody.

FIG. 5.

(A) Inhibition of IL-6 production by IL-13/IL-17AF multi-specific antibody, in response to human or cynomolgus IL-17A in combination with TNF-α. (i) Human IL-17A. (ii) Cynomolgus IL-17A.

(B) Inhibition of IL-6 production by IL-13/IL-17AF multi-specific antibody, in response to human or cynomolgus IL-17F in combination with TNF-α. (i) Human IL-17F. (ii) Cynomolgus IL-17F.

FIG. 6.

Simultaneous neutralisation of IL-13, IL-17A and IL-17F by IL-13/IL-17AF multi-specific antibody in an NHEK CXCL1 release bioassay.

Key:

circle=anti-IL-13/IL-17AF square=anti-IL-17A up-pointing triangle=anti-IL-17F down-pointing triangle=anti-IL-13

FIG. 7.

Diagrammatic illustration of a multi-specific IL-13/IL-17AF antibody according to the present invention.

DETAILED DESCRIPTION OF THE INVENTION

IL-13

IL-13 is a short-chain cytokine sharing 25% sequence identity with IL-4. It comprises approximately 132 amino acids, forming a secondary structure of four helices spanning residues 10-21 (helix A), 43-52 (helix B), 61-69 (helix C), and 92-110 (helix D), along with two p strands spanning residues 33-36 and 87-90. The solution structure of IL-13 has been solved, revealing the predicted up-up-down-down four-helix-bundle conformation that is also observed with IL-4. (Eisenmesser 2001).

Human IL-13 is a 17 kDa glycoprotein and is produced by activated T-cells of the Th2 lineage, although Th0 and Th1 CD4+ T cells, CD8+ T cells, and several non-T cell populations such as mast cells also produce IL-13. The functions of IL-13 include immunoglobulin isotype switching to IgE in human B cells and suppressing inflammatory cytokine production in both humans and mice.

IL-13 binds to its cell surface receptors, IL-13R-alpha1 and IL-13R-alpha2. IL-13R-alpha1 interacts with IL-13 with a low affinity ($K_D$~10 nM), followed by recruitment of IL-4R-alpha to form a high affinity ($K_D$~0.4 nM) signalling heterodimeric receptor complex.

The IL-4R/IL-13R-alpha1 complex is expressed on many cell types, such as B cells, monocytes/macrophages, dendritic cells, eosinophils, basophils, fibroblasts, endothelial cells, airway epithelial cells, and airway smooth muscle cells. Ligation of the IL-13R-alpha/IL-4R receptor complex results in activation of a variety of signal-transduction pathways, including signal transducer and activator of transcription 6 (STAT6) and insulin receptor substrate 2 (IRS2) pathways.

The IL-13R-alpha2 chain alone has a high affinity for IL-13 ($K_D$~0.25-0.4 nM). It functions both as a decoy receptor that negatively regulates IL-13 binding, and as a signalling receptor that induces TGF-β synthesis and fibrosis via AP-1 pathway in macrophages and possibly other cell types.

IL-13 is implicated in the pathogenesis of many human disorders and therapeutic strategies have been designed to inhibit or counteract IL-13 activity. In particular, antibodies that bind to and neutralise IL-13 have been sought as a means to inhibit IL-13 activity. However, there exists a need in the art for suitable and/or improved antibodies capable of binding IL-13, especially human IL-13 and in particular, antibodies which are capable of neutralising human IL-13.

The present invention provides a novel family of binding proteins, CDR grafted antibodies, humanised antibodies and fragments thereof, capable of binding human IL-13, binding with high affinity, and binding and neutralising human IL-13.

Antibodies that inhibit IL-13 activity may operate via several possible mechanisms of action. Bin 1 represents an antibody that binds to human IL-13 and prevents binding of IL-13Rα1 and as a result also blocks IL-4R from binding. Bin 1 antibodies may also prevent binding of IL-13 to IL-13Rα2. Bin 2 represents an antibody that binds hIL-13 in such a way that it allows binding to IL-13Rα1 but prevents recruitment of IL-4R into the complex. We were selecting antibodies that operated via bin 1.

In one embodiment, the multi-specific antibody binds to human IL-13 and prevents binding of IL-13Rα1.

In one embodiment, the multi-specific antibody binds to human IL-13 and prevents binding of IL-13Rα2.

In one embodiment, the multi-specific antibody binds to human IL-13 and prevents binding of IL-13Rα1 and IL-13Rα2.

In one embodiment, the multi-specific antibody binds to human IL-13 with a $K_D$ of <100 pM.

IL-17

The IL-17 family of cytokines consists of 6 members based on structural similarities, with a molecular mass of 23-36 kDa and a dimer structure. The founding member IL-17A (often still referred to in the literature as simply IL-17) shares 16%-50% amino acid sequence identity with other members: IL-17B, IL-17C, IL-17D, IL-17E (also known as IL-25) and IL-17F. IL-17A and IL-17F share the greatest homology (50%) and bind to the same receptor complex, thus shared biological activities have been noted between these 2 cytokines. In addition, IL-17A and IL-17F exist not only as homodimers, but also as an IL-17A/F heterodimer. IL-17E (IL-25) has the least similarity with IL-17A. Of significance and relevance to the biological activity of IL-17A and IL-17F is the finding that they share the same IL-17RA/IL-17RC receptor complex, with IL-17A having greatest affinity for IL-17RA, whereas IL-17F binds more strongly to IL-17RC. The other family member to utilise IL-17RA is IL-17E, which signals via the IL-17RA/IL-17RB receptor complex.

IL-17A and IL-17F are produced by the Th17 subset of CD4+ T cells. In addition, other T cell subsets produce IL-17A and IL-17F including cytotoxic CD8+ T cells (Tc17), gdT cells and NK T cells. Other cell populations reported to secrete IL-17A include neutrophils, monocytes, NK cells, lymphoid tissue inducer-like (LTi-like) cells, intestinal paneth cells and even B cells and mast cells. In addition, epithelial cells have been reported to secrete IL-17F.

The cell types which respond to IL-17 cytokines are reflected by the expression of the different receptors. IL-17RA is ubiquitously expressed, with particularly high levels in haematopoietic tissues whereas IL-17RC is more highly expressed in non-immune cells of joints, liver, kidney, thyroid and prostate. This differential expression could explain differences in IL-17A and IL-17F biological activity as cells expressing high levels of IL-17RC could be more responsive to IL-17F whereas cells with higher expression of IL-17RA than IL-17RC may respond more readily to IL-17A. Specific cell types that are responsive to IL-17A and F include fibroblasts, epithelial cells, keratinocytes, synoviocytes and endothelial cells with IL-17A also reported to act on T and B cells and macrophages.

The multi-specific antibody of the present invention is capable of binding to human IL-17A and/or IL-17F. Thus, the antibody can bind to IL-17A homodimer, IL-17F homodimer and/or IL-17AF heterodimer.

In one embodiment, the multi-specific antibody binds to human IL-17A. In one embodiment, the multi-specific antibody binds to human IL-17F. In one embodiment, the multi-specific antibody binds to human IL-17A and IL-17F.

In one embodiment the multi-specific antibody binds to human IL-17A with a $K_D$ of <50 µM.

In one embodiment the multi-specific antibody binds to human IL-17A with a $K_D$ of <25 µM.

In one embodiment the multi-specific antibody binds to human IL-17A with a $K_D$ of <10 µM.

In one embodiment the multi-specific antibody binds to human IL-17F with a $K_D$ of <200 µM.

In one embodiment the multi-specific antibody binds to human IL-17F with a $K_D$ of <100 µM.

Albumin

The high specificity and affinity of antibodies make them ideal diagnostic and therapeutic agents, particularly for modulating protein:protein interactions. However, antibodies may suffer from an increased rate of clearance from serum, especially when they lack the Fc domain that imparts a long lifetime in vivo (Medasan et al., 1997, J. Immunol. 158:2211-2217).

Means to improve the half-life of antibodies are known. One approach has been to conjugate the fragment to polymer molecules. Thus, the short circulating half-life of Fab', F(ab')$_2$ fragments in animals has been improved by conjugation to polyethylene glycol (PEG; see, for example, WO98/25791, WO99/64460 and WO98/37200). Another approach has been to modify the antibody fragment by conjugation to an agent that interacts with the FcRn receptor (see, for example, WO97/34631). Yet another approach to extend half-life has been to use polypeptides that bind serum albumin (see, for example, Smith et al., 2001, Bioconjugate Chem. 12:750-756; EP0486525; U.S. Pat. No. 6,267,964; WO04/001064; WO02/076489; and WO01/45746).

Serum albumin is an abundant protein in both vascular and extravascular compartments with a half-life in man of about 19 days (Peters, 1985, Adv Protein Chem. 37:161-245). This is similar to the half-life of IgG1, which is about 21 days (Waldeman & Strober, 1969, Progr. Allergy, 13:1-110).

Anti-serum albumin binding single variable domains have been described along with their use as conjugates to increase the half-life of drugs, including NCE (chemical entity) drugs, proteins and peptides, see for example, Holt et al., Protein Engineering, Design & Selection, vol 21, 5, pp283-288, WO04003019, WO2008/096158, WO05118642, WO2006/0591056 and WO2011/006915. Other anti-serum albumin antibodies and their use in multispecific antibody formats have been described in WO2009/040562, WO2010/035012 and WO2011/086091. In particular, we have previously described an anti-albumin antibody with improved humanisation in WO2013/068571.

The multi-specific antibodies of the present invention may be engineered to bind to human serum albumin, in order to extend their in vivo serum half-life, resulting in improved pharmacokinetic profiles.

Antibodies

Antibodies for use in the context of the present disclosure include whole antibodies and functionally active fragments thereof, i.e. molecules that specifically bind to IL-13, IL-17A and/or IL-17F, also termed antigen-binding fragments. Features described herein with respect to antibodies also apply to antibody fragments unless context dictates otherwise.

Whole antibodies, also known as "immunoglobulins (Ig)" generally relate to intact or full-length antibodies i.e. comprising the elements of two heavy chains and two light chains, inter-connected by disulphide bonds, which assemble to define a characteristic Y-shaped three-dimensional structure. Classical natural whole antibodies are monospecific in that they bind one antigen type, and bivalent in that they have two independent antigen binding domains. The terms "intact antibody", "full-length antibody" and "whole antibody" are used interchangeably to refer to a monospecific bivalent antibody having a structure similar to a native antibody structure, including an Fc region as defined herein.

Each light chain is comprised of a light chain variable region (abbreviated herein as $V_L$) and a light chain constant region ($C_L$). Each heavy chain is comprised of a heavy chain variable region (abbreviated herein as $V_H$) and a heavy chain constant region (CH) constituted of three constant domains $CH_1$, $CH_2$ and $CH_3$, or four constant domains $CH_1$, $CH_2$, $CH_3$ and $CH_4$, depending on the Ig class. The "class" of an Ig or antibody refers to the type of constant region and includes IgA, IgD, IgE, IgG and IgM and several of them can be further divided into subclasses, e.g. IgG1, IgG2, IgG3, IgG4. The constant regions of the antibodies may mediate the binding of the immunoglobulin to host tissues or factors, including various cells of the immune system (e.g., effector cells) and the first component (Clq) of the classical complement system.

The $V_H$ and $V_L$ regions of the antibody according to the present invention can be further subdivided into regions of hypervariability (or "hypervariable regions") determining the recognition of the antigen, termed complementarity determining regions (CDR), interspersed with regions that are more structurally conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The CDRs and the FR together form a variable region. By convention, the CDRs in the heavy chain variable region of an antibody or antigen-binding fragment thereof are referred as CDR-H1, CDR-H2 and CDR-H3 and in the light chain variable regions as CDR-L1, CDR-L2 and CDR-L3. They are numbered sequentially in the direction from the N-terminus to the C-terminus of each chain.

CDRs are conventionally numbered according to a system devised by Kabat et al. This system is set forth in Kabat et al., 1991, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering, corresponding to a shortening of, or insertion into, a structural component, whether framework or complementarity determining region, of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus, unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

In addition to the CDR loops, a fourth loop exists between CDR-2 (CDR-L2 or CDR-H2) and CDR-3 (CDR-L3 or CDR-H3) which is formed by framework 3 (FR3). The Kabat numbering system defines framework 3 as positions 66-94 in a heavy chain and positions 57-88 in a light chain.

Based on the alignment of sequences of different members of the immunoglobulin family, numbering schemes have been proposed and are for example described in Kabat et al., 1991, and Dondelinger et al., 2018, Frontiers in Immunology, Vol 9, article 2278.

The term "constant domain(s)", "constant region", as used herein are used interchangeably to refer to the domain(s) of an antibody which is outside the variable regions. The constant domains are identical in all antibodies of the same isotype but are different from one isotype to another. Typically, the constant region of a heavy chain is formed, from N to C terminal, by $CH_1$-hinge -$CH_2$-$CH_3$-optionally $CH_4$, comprising three or four constant domains.

The constant domains of the antibody molecule of the present invention, if present, may be selected having regard to the proposed function of the antibody molecule, and in particular the effector functions which may be required. For example, the constant domains may be human IgA, IgD, IgE, IgG or IgM domains. In particular, human IgG constant domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant domains may also be used. For example, IgG4 molecules in which the serine at position 241 (numbered according to the Kabat numbering system) has been changed to proline as described in Angal et al. (Angal et al., 1993. A single amino acid substitution abolishes the heterogeneity of chimeric mouse/human (IgG4) antibody as observed during SDS-PAGE analysis Mol Immunol 30, 105-108) and termed IgG4P herein, may be used.

"Fc", "Fc fragment", "Fc-domain" and "Fc region" are used interchangeably to refer to the C-terminal region of an antibody comprising the constant region of an antibody excluding the first constant immunoglobulin domain. Thus, Fc refers to the last two constant domains, $CH_2$ and $CH_3$, of IgA, IgD, and IgG, or the last three constant domains of IgE and IgM, and the flexible hinge N-terminal to these domains. The human IgG1 heavy chain Fc region is defined herein to comprise residues C226 to its carboxyl-terminus, wherein the numbering is according to the EU index as in Kabat. In the context of human IgG1, the lower hinge refers to positions 226-236, the $CH_2$ domain refers to positions 237-340 and the $CH_3$ domain refers to positions 341-447 according to the EU index as in Kabat. The corresponding Fc region of other immunoglobulins can be identified by sequence alignments.

In the context of the present disclosure, when present, the constant region or Fc region may be natural, as defined above, or else may be modified in various ways, provided that it comprises a functional FcR binding domain, and preferably a functional FcRn binding domain. Preferably, the modified constant region or Fc region lead to improve functionalities and/or pharmacokinetics. The modifications may include deletion of certain portions of the Fc fragment. The modifications may further include various amino acid substitutions able to affect the biological properties of the antibody. Mutations for increasing FcRn binding and thus in vivo half-life may also be present. The modifications may further include modification in the glycosylation profile of the antibody. The natural Fc fragment is glycosylated in the $CH_2$ domain with the presence, on each of the two heavy chains, of an N-glycan bound to the asparagine residue at position 297 (Asn297). In the context of the present disclosure, the antibody may be glyco-modified, i.e. engineered to have a particular glycosylation profile, which, for example, leads to improved properties, e.g. improved effector function, or improved serum half-life.

The antibodies described herein are isolated. An "isolated" antibody is one which has been separated (e.g. by purification means) from a component of its natural environment.

The term "antibody" encompasses monovalent, i.e. antibodies comprising only one antigen binding domain (e.g. one-armed antibodies comprising a full-length heavy chain and a full-length light chain interconnected, also termed "half-antibody"), and multivalent antibodies, i.e. antibodies comprising more than one antigen binding domain.

The term "antibody" according to the invention also encompasses antigen-binding fragments of antibodies. Antigen-binding fragments of antibodies include single chain antibodies (e.g. scFv, and dsscfv), Fab, Fab', $F(ab')_2$, Fv, single domain antibodies or nanobodies (e.g. $V_H$ or $V_L$, or $V_{HH}$ or $V_{NAR}$). Other antibody fragments for use in the present invention include the Fab and Fab' fragments described in International patent applications WO2011/117648, WO2005/003169, WO2005/003170 and WO2005/003171.

The methods for creating and manufacturing these antibody fragments are well known in the art (see for example Verma et al., 1998, Journal of Immunological Methods, 216, 165-181).

The term "Fab fragment" as used herein refers to an antibody fragment comprising a light chain fragment comprising a $V_L$ (variable light) domain and a constant domain of a light chain (CL), and a $V_H$ (variable heavy) domain and a first constant domain (CH₁) of a heavy chain.

A typical "Fab' fragment" comprises a heavy and a light chain pair in which the heavy chain comprises a variable region $V_H$, a constant domain CH₁ and a natural or modified hinge region and the light chain comprises a variable region $V_L$ and a constant domain CL. Dimers of a Fab' according to the present disclosure create a F(ab')₂ where, for example, dimerisation may be through the hinge.

The term "single domain antibody" as used herein refers to an antibody fragment consisting of a single monomeric variable antibody domain. Examples of single domain antibodies include $V_H$ or $V_L$ or $V_H$H or V-NAR.

The term "Fv" refers to two variable domains, for example co-operative variable domains, such as a cognate pair or affinity matured variable domains, i.e. a $V_H$ and $V_L$ pair. "Single chain variable fragment" or "scFv" as employed herein refers to a single chain variable fragment, comprising or consisting of a heavy chain variable domain ($V_H$) and a light chain variable domain ($V_L$) which is stabilised by a peptide linker between the $V_H$ and $V_L$ variable domains. The $V_H$ and $V_L$ variable domains may be in any suitable orientation, for example the C-terminal of $V_H$ may be linked to the N-terminal of $V_L$ or the C-terminal of $V_L$ may be linked to the N-terminal of $V_H$.

"Disulphide-stabilised single chain variable fragment" or "dsscFv" as employed herein refers to a single chain variable fragment which is stabilised by a peptide linker between the $V_H$ and $V_L$ variable domains and also includes an inter-domain disulphide bond between $V_H$ and $V_L$. (see for example, Weatherill et al., Protein Engineering, Design & Selection, 25 (321-329), 2012, WO2007109254.

"Disulphide-stabilised variable fragment" or "dsFv" as employed herein refers to a single chain variable fragment which does not include a peptide linker between the $V_H$ and $V_L$ variable domains and is instead stabilised by an inter-domain disulphide bond between $V_H$ and $V_L$.

In one embodiment, the multi-specific antibody of the present invention is an antagonistic antibody. As used herein, the term "antagonistic antibody" describes an antibody that is capable of inhibiting or neutralising the biological signaling activity of one or more antigens, for example by blocking binding, or reducing binding of IL-13, IL-17A and/or IL-17F to their receptors.

Antibodies for use in the present invention may be, but are not limited to, monoclonal, humanised, fully human or chimeric antibodies.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp77-96, Alan R Liss, Inc., 1985).

Antibodies may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15):7843-78481; WO92/02551; WO2004/051268 and International Patent Application number WO2004/106377.

Screening for antibodies can be performed using assays to measure binding to an antigen, and/or assays to measure the ability to block the binding of an antigen to one or more of it's receptors. An example of a binding assay is an ELISA, for example, using a fusion protein of IL-13, which is immobilized on plates, and employing a conjungated secondary antibody to detect anti-IL-13 antibody bound to the IL-13. An example of a blocking assay is a flow cytometry based assay measuring the blocking of IL-13 ligand protein binding to an IL-13R. A fluorescently labelled secondary antibody is used to detect the amount of IL-13 ligand protein binding to the IL-13R.

Humanised antibodies (which include CDR-grafted antibodies) are antibody molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

Chimeric antibodies are composed of elements derived from two different species such that the element retains the characteristics of the species from which it is derived. Generally a chimeric antibody will comprise a variable region from one species, for example a mouse, rat, rabbit or similar and constant region from another species such as a human.

Antibodies can also be generated using various. phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

Fully human antibodies are those antibodies in which the variable regions and the constant regions (where present) of both the heavy and the light chains are all of human origin, or substantially identical to sequences of human origin, but not necessarily from the same antibody. Examples of fully human antibodies may include antibodies produced, for example by the phage display methods described above and antibodies produced by mice in which the murine immunoglobulin variable and optionally the constant region genes have been replaced by their human counterparts eg. as described in general terms in EP 0546073, U.S. Pat. Nos. 5,545,806, 5,569,825, 5,625,126, 5,633,425, 5,661,016, 5,770,429, EP 0438474 and EP 0463151.

Multi-Specific Antibodies

The antibody of the present invention is a multi-specific antibody. "Multispecific or Multi-specific antibody" as employed herein refers to an antibody as described herein which has at least two binding domains, i.e. two or more binding domains, for example two or three binding domains, wherein the at least two binding domains independently bind two different antigens or two different epitopes on the same antigen. Multi-specific antibodies are generally monovalent for each specificity (antigen). Multi-specific antibodies described herein encompass monovalent and multivalent, e.g. bivalent, trivalent, tetravalent multi-specific antibodies.

A paratope is a region of an antibody which recognises and binds to an antigen. An antibody of the invention may be a multi-paratopic antibody. "Multi-paratopic antibody" as employed herein refers to an antibody as described herein which comprises two or more distinct paratopes, which interact with different epitopes either from the same antigen or from two different antigens. Multi-paratopic antibodies described herein may be biparatopic, triparatopic, tetraparatopic.

"Antigen binding domain" as employed herein refers to a portion of the antibody, which comprises a part or the whole of one or more variable domains, for example a part or the whole of a pair of variable domains $V_H$ and $V_L$, that interact specifically with the target antigen. A binding domain may comprise a single domain antibody. In one embodiment, each binding domain is monovalent. Preferably each binding domain comprises no more than one VH and one $V_L$.

"Specifically" as employed herein refers to a binding domain that only recognises the antigen to which it is specific, or a binding domain that has significantly higher binding affinity for the antigen to which it is specific compared to affinity for antigens to which it is non-specific. Binding affinity may be measured by standard assays, for example surface plasmon resonance, such as BIAcore.

A variety of multi-specific antibody formats have been generated. Different classifications have been proposed, but multispecific IgG antibody formats generally include bispecific IgG, appended IgG, multispecific (e.g. bispecific) antibody fragments, multispecific (e.g. bispecific) fusion proteins, and multispecific (e.g. bispecific) antibody conjugates, as described for example in Spiess et al., Alternative molecular formats and therapeutic applications for bispecific antibodies. Mol Immunol. 67(2015):95-106.

Techniques for making bispecific antibodies include, but are not limited to, CrossMab technology (Klein et al. Engineering therapeutic bispecific antibodies using CrossMab technology, Methods 154 (2019) 21-31), Knobs-in-holes engineering (e.g. WO1996027011, WO1998050431), Duo-Body technology (e.g. WO2011131746), Azymetric technology (e.g. WO2012058768). Further technologies for making bispecific antibodies have been described for example in Godar et al., 2018, Therapeutic bispecific antibody formats: a patent applications review (1994-2017), Expert Opinion on Therapeutic Patents, 28:3, 251-276. Bispecific antibodies include in particular CrossMab antibodies, DAF (two-in-one), DAF (four-in-one), DutaMab, DT-IgG, Knobs-in-holes common LC, Knobs-in-holes assembly, Charge pair, Fab-arm exchange, SEEDbody, Triomab, LUZ-Y, Fcab, KA-body and orthogonal Fab.

Appended IgG classically comprise full-length IgG engineered by appending additional antigen-binding domain or antigen-binding fragment to the N- and/or C-terminus of the heavy and/or light chain of the IgG. Examples of such additional antigen-binding fragments include sdAb antibodies (e.g. $V_H$ or $V_L$), Fv, scFv, dsscFv, Fab, scFav. Appended IgG antibody formats include in particular DVD-IgG, IgG (H)-scFv, scFv-(H)IgG, IgG(L)-scFv, scFv-(L)IgG, IgG(L, H)-Fv, IgG(H)-V, V(H)—IgG, IgC(L)-V, V(L)-IgG, KIH IgG-scFab, 2scFv-IgG, IgG-2scFv, scFv4-Ig, Zybody and DVI-IgG (four-in-one), for example as described in Spiess et al., Alternative molecular formats and therapeutic applications for bispecific antibodies. Mol Immunol. 67(2015):95-106.

Multispecific antibody fragments include nanobody, nanobody-HAS, BiTEs, diabody, DART, TandAb, scDiabody, sc-Diabody-CH3, Diabody-CH3, Triple Body, Miniantibody; Minibody, Tri Bi minibody, scFv-CH3 KIH, Fab-scFv, scFv-CH-CL-scFv, F(ab')2, F(ab')2-scFV3, scFv-KIH, Fab-scFv-Fc, Tetravalent HCAb, scDiabody-Fc, Diabody-Fc, Tandem scFv-Fc; and intrabody, as described, for example, Spiess et al., Alternative molecular formats and therapeutic applications for bispecific antibodies. Mol Immunol. 67(2015):95-106. Multispecific fusion proteins include Dock and Lock, ImmTAC, HSAbody, scDiabody-HAS, and Tandem scFv-Toxin.

Multispecific antibody conjugates include IgG-IgG; Cov-X-Body; and scFv1-PEG-scFv2. Additional multispecific antibody formats have been described for example in Brinkmann and Kontermann, The making of bispecific antibodies, mAbs, 9:2, 182-212 (2017), in particular in FIG. 2, for example tandem scFv, triplebody, Fab-VHH, taFv-Fc, scFv$_4$-Ig, scFv$_2$-Fcab, scFv$_4$-IgG. Bibodies, tribodies and methods for producing the same are disclosed for example in WO99/37791.

The invention provides a multi-specific antibody which binds human IL-13, human IL-17A, and/or human IL-17F.

In one embodiment, the multi-specific antibody comprises an antigen binding site that binds to human IL-13, wherein the IL-13 binding site comprises a light chain variable region comprising the sequence given in SEQ ID NO:15 for CDR-L1, the sequence given in SEQ ID NO:16 for CDR-L2 and the sequence given in SEQ ID NO:17 for CDR-L3.

In one embodiment, the multi-specific antibody comprises an antigen-binding site that binds to human IL-13, wherein the IL-13 binding site comprises a heavy chain variable region comprising the sequence given in SEQ ID NO:18 for CDR-H1, the sequence given in SEQ ID NO:19 for CDR-H2 and the sequence given in SEQ ID NO:20 for CDR-H3.

In one embodiment, the IL-13 binding site comprises a light chain variable region comprising the sequence given in SEQ ID NO:27.

In one embodiment, the IL-13 binding site comprises a heavy chain variable region comprising the sequence given in SEQ ID NO:28.

In one embodiment, the IL-13 binding site comprises a light chain variable region comprising the sequence given in SEQ ID NO:31.

In one embodiment, the IL-13 binding site comprises a heavy chain variable region comprising the sequence given in SEQ ID NO:32.

In one embodiment, the multi-specific antibody comprises an antigen binding site that binds to human IL-17A and human IL-17F comprising:
a light chain variable region comprising the sequence given in SEQ ID NO:1 for CDR-L1, the sequence given in SEQ ID NO:2 for CDR-L2 and the sequence given in SEQ ID NO:3 for CDR-L3.

In one embodiment, the multi-specific antibody comprises an antigen binding site that binds to human IL-17A and human IL-17F comprising:
a heavy chain variable region comprising the sequence given in SEQ ID NO:4 for CDR-H1, the sequence given in SEQ ID NO:5 for CDR-H2 and the sequence given in SEQ ID NO:6 for CDR-H3.

In one embodiment, the antigen binding site that binds to human IL-17A and human IL-17F comprises a light chain variable region comprising the sequence given in SEQ ID NO:7.

In one embodiment, the antigen binding site that binds to human IL-17A and human IL-17F comprises a heavy chain variable region comprising the sequence given in SEQ ID NO:9.

In one embodiment, the multi-specific antibody lacks an Fc-domain and half-life is provided by an antigen binding site that binds to serum albumin.

In one embodiment, the multi-specific antibody comprises the sequence given in SEQ ID NO:57 or SEQ ID NO: 59.

In one embodiment, the multi-specific antibody comprises the sequence given in SEQ ID NO:61 or SEQ ID NO: 63.

In one embodiment, the multi-specific antibody comprises the sequence given in SEQ ID NO:59 and the sequence given in SEQ ID NO: 63.

In one embodiment, the multi-specific antibody comprises or consists of:

a polypeptide chain of formula (I):

$$V_H\text{-}CH_1\text{-}(CH_2)_s\text{-}(CH_3)_t\text{-}X\text{-}(V_1)p;\text{ and}$$

a polypeptide chain of formula (II):

$$V_L\text{-}C_L\text{-}Y\text{-}V_2;$$

wherein:

$V_H$ represents a heavy chain variable domain;

$CH_1$ represents domain 1 of a heavy chain constant region;

$CH_2$ represents domain 2 of a heavy chain constant region;

$CH_3$ represents domain 3 of a heavy chain constant region;

X represents a bond or linker;

$V_1$ represents a dsscFv, a dsFv, or a scFv;

$V_L$ represents a light chain variable domain;

$C_L$ represents a domain from a light chain constant region, such as Ckappa;

Y represents a bond or linker;

$V_2$ represents a dsscFv, a dsFv, or a scFv;

p represents 0 or 1;

s represents 0 or 1;

t represents 0 or 1;

wherein when p is 0, X is absent and when q is 0, Y is absent; and wherein the polypeptide chain of formula (I) comprises a protein A binding domain; and wherein the polypeptide chain of formula (II) does not bind protein A.

In one embodiment when s is 0 and t is 0, the multi-specific antibody according to the present disclosure is provided as a dimer of a heavy and light chain of:

Formula (I) and (II) respectively, wherein the $V_H$-$CH_1$ portion together with the $V_L$-$C_L$ portion form a functional Fab or Fab' fragment.

In one embodiment when s is 1 and t is 1, the multi-specific antibody according to the present disclosure is provided as a dimer of two heavy chains and two light chains of:

Formula (I) and (II) respectively, wherein the two heavy chains are connected by interchain interactions, notably at the level of $CH_2$-$CH_3$, and wherein the $V_H$-$CH_1$ portion of each heavy chain together with the $V_L$-$C_L$ portion of each light chain, form a functional Fab or Fab' fragment. In such embodiment, the two $V_H$-$CH_1$-$CH_2$-$CH_3$ portions together with the two $V_L$-$C_L$ portions form a functional full-length antibody. In such embodiment, the full-length antibody may comprise a functional Fc region.

$V_H$ represents a heavy chain variable domain. In one embodiment $V_H$ is humanised. In one embodiment the $V_H$ is fully human.

$V_L$ represents a light chain variable domain. In one embodiment $V_L$ is humanised. In one embodiment the $V_L$ is fully human.

Generally, $V_H$ and $V_L$ together form an antigen binding domain. In one embodiment $V_H$ and $V_L$ form a cognate pair.

"Cognate pair" as employed herein refers to a pair of variable domains from a single antibody, which was generated in vivo, i.e. the naturally occurring pairing of the variable domains isolated from a host. A cognate pair is therefore a $V_H$ and $V_L$ pair. In one example, the cognate pair bind the antigen co-operatively.

"Variable region" or "variable domain" as employed herein refers to the region in an antibody chain comprising the CDRs and a framework, in particular a suitable framework.

Variable regions for use in the present disclosure will generally be derived from an antibody, which may be generated by any method known in the art.

"Derived from" as employed herein refers to the fact that the sequence employed or a sequence highly similar to the sequence employed was obtained from the original genetic material, such as the light or heavy chain of an antibody.

"Highly similar" as employed herein is intended to refer to an amino acid sequence which over its full length is 95% similar or more, such as 96, 97, 98 or 99% similar.

Variable regions for use in the present invention, as described herein above for $V_H$ and $V_L$ may be from any suitable source and may be for example, fully human or humanised.

In one embodiment, the binding domain formed by $V_H$ and $V_L$ are specific to a first antigen.

In one embodiment, the binding domain of $V_1$ is specific to a second antigen.

In one embodiment, the binding domain of $V_2$ is specific to a third antigen.

In one embodiment, each one of $V_H$-$V_L$, $V_1$, and $V_2$, as present, separately binds its respective antigen.

In one embodiment, the $CH_1$ domain is a naturally occurring domain 1 from an antibody heavy chain or a derivative thereof. In one embodiment, the $CH_2$ domain is a naturally occurring domain 2 from an antibody heavy chain or a derivative thereof. In one embodiment, the $CH_3$ domain is a naturally occurring domain 3 from an antibody heavy chain or a derivative thereof.

In one embodiment, the $C_L$ fragment, in the light chain, is a constant kappa sequence or a derivative thereof. In one embodiment, the $C_L$ fragment, in the light chain, is a constant lambda sequence or a derivative thereof.

A derivative of a naturally occurring domain as employed herein is intended to refer to where at least one amino acid in a naturally occurring sequence have been replaced or deleted, for example to optimize the properties of the domain such as by eliminating undesirable properties but wherein the characterizing feature(s) of the domain is/are retained. In one embodiment, a derivative of a naturally occurring domain comprises two, three, four, five, six, seven, eight, ten, eleven or twelve amino acid substitutions or deletions compared to a naturally occurring sequence.

In one embodiment, one or more natural or engineered inter chain (i.e. inter light and heavy chain) disulphide bonds are present in the functional Fab or Fab' fragment.

In one embodiment, a "natural" disulfide bond is present between a $CH_1$ and $C_L$ in the polypeptide chains of Formula (I) and (II).

When the $C_L$ domain is derived from either Kappa or Lambda, the natural position for a bond forming cysteine is 214 in human cKappa and cLambda (Kabat numbering 4th edition 1987).

The exact location of the disulfide bond forming cysteine in $CH_1$ depends on the particular domain actually employed. Thus, for example in human gamma-1 the natural position of the disulfide bond is located at position 233 (Kabat numbering 4th edition 1987). The position of the bond forming cysteine for other human isotypes such as gamma 2, 3, 4, IgM and IgD are known, for example position 127 for human IgM, IgE, IgG2, IgG3, IgG4 and 128 of the heavy chain of human IgD and IgA2B.

Optionally, there may be a disulfide bond between the $V_H$ and $V_L$ of the polypeptides of formula I and II.

In one embodiment, the multi-specific antibody according to the disclosure has a disulfide bond in a position equivalent or corresponding to that naturally occurring between $CH_1$ and $C_L$.

In one embodiment, a constant region comprising $CH_1$ and a constant region such as $C_L$ has a disulfide bond which is in a non-naturally occurring position. This may be engineered into the molecule by introducing cysteine(s) into the amino acid chain at the position or positions required. This non-natural disulfide bond is in addition to or as an alternative to the natural disulfide bond present between $CH_1$ and $C_L$. The cysteine(s) in natural positions can be replaced by an amino acid such as serine which is incapable on forming a disulfide bridge.

Introduction of engineered cysteines can be performed using any method known in the art. These methods include, but are not limited to, PCR extension overlap mutagenesis, site-directed mutagenesis or cassette mutagenesis (see, generally, Sambrook et al., Molecular Cloning, A Laboratory Manual, Cold Spring Harbour Laboratory Press, Cold Spring Harbour, NY, 1989; Ausbel et al., Current Protocols in Molecular Biology, Greene Publishing & Wiley-Interscience, NY, 1993). Site-directed mutagenesis kits are commercially available, e.g. QuikChange® Site-Directed Mutagenesis kit (Stratagene, La Jolla, CA). Cassette mutagenesis can be performed based on Wells et al., 1985, Gene, 34:315-323. Alternatively, mutants can be made by total gene synthesis by annealing, ligation and PCR amplification and cloning of overlapping oligonucleotides.

In one embodiment, a disulfide bond between $CH_1$ and $C_L$ is completely absent, for example the interchain cysteines may be replaced by another amino acid, such as serine. Thus, in one embodiment there are no interchain disulphide bonds in the functional Fab fragment of the molecule. Disclosures such as WO2005/003170, incorporated herein by reference, describe how to provide Fab fragments without an inter chain disulphide bond.

Examples of antibody formats for use in the present invention include appended IgG and appended Fab, wherein a whole IgG or a Fab fragment, respectively, is engineered by appending at least one additional antigen-binding domain (e.g. one, two, three or four additional antigen-binding domains), for example a single domain antibody (such as $V_H$ or $V_L$, or VHH), a scFv, a dsscFv, a dsFv to the N- and/or C-terminus of the light chain of said IgG or Fab, and optionally to the heavy chain of said IgG or Fab, for example as described in WO2009/040562, WO2010035012, WO2011/030107, WO2011/061492, WO2011/061246 and WO2011/086091 all incorporated herein by reference. An appended IgG comprising a full-length IgG engineered by appending a dsFv to the C-terminus of the light chain (and optionally to the heavy chain) of the IgG, was first disclosed in WO2015/197789, incorporated herein by reference.

A preferred antibody format for use in the present invention comprises a Fab linked to two scFvs or dsscFvs, each scFv or dsscFv binding the same or a different target (e.g., one scFv or dsscFv binding a therapeutic target and one scFv or dsscFv that increases half-life by binding, for instance, albumin). Such antibody fragments are described in International Patent Application Publication No WO2015/

197772, which is hereby incorporated by reference in its entirety and particularly with respect to the discussion of antibody fragments.

$V_1$ represents a dsscFv, a dsFv, or a scFv.

$V_2$ represents a dsscFv, a dsFv, or a scFv.

In one embodiment, when $V_1$ and/or $V_2$ are a dsFv or a dsscFv, the disulfide bond between the variable domains $V_H$ and $V_L$ of $V_1$ and/or $V_2$ is between two of the residues listed below (unless the context indicates otherwise Kabat numbering is employed in the list below).

Wherever reference is made to Kabat numbering the relevant reference is Kabat et al., 1991 ($5^{th}$ edition, Bethesda, Md.), in Sequences of Proteins of Immunological Interest, US Department of Health and Human Services, NIH, USA.

In one embodiment the disulfide bond is in a position selected from the group comprising:

$V_H37+V_L95C$ see for example Protein Science 6, 781-788 Zhu et al (1997);

$V_H44+V_L100$ see for example; for example, Weatherill et al., Protein Engineering, Design & Selection, 25 (321-329), 2012);

$V_H44+V_L105$ see for example J Biochem. 118, 825-831 Luo et al (1995);

$V_H45+V_L87$ see for example Protein Science 6, 781-788 Zhu et al (1997);

$V_H55+V_L101$ see for example FEBS Letters 377 135-139 Young et al (1995);

$V_H100+V_L50$ see for example Biochemistry 29 1362-1367 Glockshuber et al (1990);

$V_H100b+V_L49$; see for example Biochemistry 29 1362-1367 Glockshuber et al (1990);

$V_H98+V_L 46$; see for example Protein Science 6, 781-788 Zhu et al (1997);

$V_H101+V_L46$; see for example Protein Science 6, 781-788 Zhu et al (1997);

$V_H105+V_L43$ see for example; Proc. Natl. Acad. Sci. USA Vol. 90 pp. 7538-7542 Brinkmann et al (1993); or Proteins 19, 35-47 Jung et al (1994), $V_H106+V_L57$ see for example FEBS Letters 377 135-139 Young et al (1995) and a position corresponding thereto in a variable region pair located in the molecule.

In one embodiment, the disulphide bond is formed between positions $V_H44$ and $V_L100$.

The amino acid pairs listed above are in the positions conducive to replacement by cysteines such that disulfide bonds can be formed. Cysteines can be engineered into these desired positions by known techniques. In one embodiment, therefore, an engineered cysteine according to the present disclosure refers to where the naturally occurring residue at a given amino acid position has been replaced with a cysteine residue.

Introduction of engineered cysteines can be performed using any method known in the art. These methods include, but are not limited to, PCR extension overlap mutagenesis, site-directed mutagenesis or cassette mutagenesis (see, generally, Sambrook et al., Molecular Cloning, A Laboratory Manual, Cold Spring Harbour Laboratory Press, Cold Spring Harbour, NY, 1989; Ausbel et al., Current Protocols in Molecular Biology, Greene Publishing & Wiley-Interscience, NY, 1993). Site-directed mutagenesis kits are commercially available, e.g. QuikChange® Site-Directed Mutagenesis kit (Stratagen, La Jolla, CA). Cassette mutagenesis can be performed based on Wells et al., 1985, Gene, 34:315-323.

Alternatively, mutants can be made by total gene synthesis by annealing, ligation and PCR amplification and cloning of overlapping oligonucleotides.

Accordingly, in one embodiment when $V_1$ and/or $V_2$ are a dsFv or a dsscFv, the variable domains $V_H$ and $V_L$ of $V_1$ and/or the variable domains $V_H$ and $V_L$ of $V_2$, may be linked by a disulfide bond between two cysteine residues, wherein the position of the pair of cysteine residues is selected from the group consisting of: $V_H37$ and $V_L95$, $V_H44$ and $V_L100$, $V_H44$ and $V_L105$, $V_H45$ and $V_L87$, $V_H100$ and $V_L50$, $V_H100b$ and $V_L49$, $V_H98$ and $V_L46$, $V_H101$ and $V_L46$, $V_H105$ and $V_L43$ and $V_H106$ and $V_L57$.

In one embodiment when $V_1$ and/or $V_2$ are a dsFv or a dsscFv, the variable domains $V_H$ and $V_L$ of $V_1$ and/or the variable domains $V_H$ and $V_L$ of $V_2$ may be linked by a disulfide bond between two cysteine residues, one in $V_H$ and one in $V_L$, which are outside of the CDRs wherein the position of the pair of cysteine residues is selected from the group consisting of $V_H37$ and $V_L95$, $V_H44$ and $V_L100$, $V_H44$ and $V_L105$, $V_H45$ and $V_L87$, $V_H100$ and $V_L50$, $V_H98$ and $V_L46$, $V_H105$ and $V_L43$ and $V_H106$ and $V_L57$.

In one embodiment when $V_1$ is a dsFv or a dsscFv, the variable domains $V_H$ and $V_L$ of $V_1$ are linked by a disulphide bond between two engineered cysteine residues, one at position $V_H44$ and the other at $V_L100$. In one embodiment when $V_2$ is a dsFv or a dsscFv, the variable domains $V_H$ and $V_L$ of $V_2$ are linked by a disulphide bond between two engineered cysteine residues, one at position $V_H44$ and the other at $V_L100$.

In one embodiment when $V_1$ is a dsscFv, a dsFv, or a scFv, the $V_H$ domain of $V_1$ is attached to X.

In one embodiment when $V_1$ is a dsscFv, a dsFv, or a scFv, the $V_L$ domain of $V_1$ is attached to X.

In one embodiment when $V_2$ is a dsscFv, a dsFv, or a scFv, the $V_H$ domain of $V_2$ is attached to Y.

In one embodiment when $V_2$ is a dsscFv, a dsFv, or a scFv, the $V_L$ domain of $V_2$ is attached to Y.

The skilled person will appreciate that when $V_1$ and/or $V_2$ represents a dsFv, the multi-specific antibody will comprise a third polypeptide encoding the corresponding free $V_H$ or $V_L$ domain which is not attached to X or Y. When $V_1$ and $V_2$ are a dsFv then the "free variable domain" (i.e. the domain linked to via a disulphide bond to the remainder of the polypeptide) will be common to both chains. Thus, whilst the actual variable domain fused or linked via X or Y to the polypeptide may be different in each polypeptide chain, the free variable domains paired therewith will generally be identical to each other.

In some embodiments, p is 1. In some embodiments, p is 0.

In some embodiments, s is 1. In some embodiments, s is 0.

In some embodiments, t is 1. In some embodiments, t is 0.

In some embodiments, s is 1 and t is 1. In some embodiments, s is 0 and t is 0.

In one embodiment, p is 1, q is 1, r is 0, s is 0 and t is 0, and $V_1$ and $V_2$ both represent a dsscFv. Thus, in one aspect, there is provided a multi-specific antibody which binds human IL-13, human IL-17A and/or human IL-17F comprising or consisting of:

a) a polypeptide chain of formula (Ia):

$$V_H\text{-}CH_1\text{-}X\text{-}V_1; \text{ and}$$

b) a polypeptide chain of formula (IIa):

$$V_L\text{-}C_L\text{-}Y\text{-}V_2;$$

wherein:
$V_H$ represents a heavy chain variable domain;
$CH_1$ represents domain 1 of a heavy chain constant region;
X represents a bond or linker;
Y represents a bond or linker;
$V_1$ represents a scFv, a dsscFv, or a dsFv;
$V_L$ represents a light chain variable domain;
$C_L$ represents a domain from a light chain constant region, such as Ckappa;
$V_2$ represents a scFv, a dsscFv or a dsFv;
wherein at least one of $V_1$ or $V_2$ is a dsscFv or a dsFv;
wherein the polypeptide chain of formula (Ia) comprises a protein A binding domain; and
wherein the polypeptide chain of formula (IIa) does not bind protein A.

In such embodiment, $V_2$ does not bind protein A, i.e. the scFv, dsscFv or dsFv of $V_2$ does not comprise a protein A binding domain. In one embodiment, $V_2$, i.e. the scFv, dsscFv or dsFv of $V_2$, comprises a VH1 domain. In another embodiment, $V_2$, i.e. the scFv, dsscFv or dsFv of $V_2$, comprises a VH3 domain which does not bind protein A. In one embodiment, $V_2$, i.e. the scFv, dsscFv or dsFv of $V_2$, comprises a VH2 domain. In one embodiment, $V_2$, i.e. the scFv, dsscFv or dsFv of $V_2$, comprises a VH4 domain. In one embodiment, $V_2$, i.e. the scFv, dsscFv or dsFv of $V_2$, comprises a VH5 domain. In one embodiment, $V_2$, i.e. the scFv, dsscFv or dsFv of $V_2$, comprises a VH6 domain. In one embodiment, the polypeptide chain of formula (Ia) comprises only one protein A binding domain present in $V_H$ or $V_1$. In one embodiment, the polypeptide chain of formula (Ia) comprises only one protein A binding domain present in $V_1$. In another embodiment, the polypeptide chain of formula (Ia) comprises two protein A binding domains present in $V_H$ and $V_1$ respectively.

In another embodiment, p is 0, q is 1, r is 0, s is 1, t is 1, and $V_2$ is a dsscFv. Thus, in one aspect, there is provided a multi-specific antibody which binds human IL-13, human IL-17A and/or human IL-17F, and comprising or consisting of:

a) a polypeptide chain of formula (Ib):

$$V_H\text{-}CH_1\text{-}CH_2\text{-}CH_3; \text{ and}$$

b) a polypeptide chain of formula (IIb):

$$V_L\text{-}C_L\text{-}Y\text{-}V_2;$$

wherein:
$V_H$ represents a heavy chain variable domain;
$CH_1$ represents domain 1 of a heavy chain constant region;
$CH_2$ represents domain 2 of a heavy chain constant region;
$CH_3$ represents domain 3 of a heavy chain constant region;
Y represents a bond or linker;
$V_L$ represents a light chain variable domain;
$C_L$ represents a domain from a light chain constant region, such as Ckappa;
$V_2$ represents a dsscFv;
wherein the polypeptide chain of formula (Ib) comprises a protein A binding domain; and
wherein the polypeptide chain of formula (IIb) does not bind protein A.

In such embodiment, $V_2$ does not bind protein A, i.e. the dsscFv of $V_2$ does not comprise a protein A binding domain. In one embodiment, $V_2$, i.e. the dsscFv of $V_2$, comprises a VH1 domain. In another embodiment, $V_2$, i.e. the dsscFv of $V_2$, comprises a VH3 domain which does not bind protein A. In one embodiment, the polypeptide chain of formula (Ib) comprises only one protein A binding domain present in $V_H$ or $CH_2$-$CH_3$. In another embodiment, the polypeptide chain of formula (Ib) comprises two protein A binding domains present in $V_H$ and $CH_2$-$CH_3$ respectively.

In another embodiment, p is 0, q is 1, r is 0, s is 1, t is 1, and $V_2$ is a dsFv. Thus, in one aspect, there is provided a multi-specific antibody which binds human IL-13, human IL-17A and/or human IL-17F comprising or consisting of:

a) a polypeptide chain of formula (Ic):

$V_H\text{-}CH_1\text{-}CH_2\text{-}CH_3;$ and b) a polypeptide chain of formula (IIc):

$V_L\text{-}C_L\text{-}Y\text{-}V_2;$ wherein:
$V_H$ represents a heavy chain variable domain;
$CH_1$ represents domain 1 of a heavy chain constant region;
$CH_2$ represents domain 2 of a heavy chain constant region;
$CH_3$ represents domain 3 of a heavy chain constant region;
Y represents a bond or linker;
$V_L$ represents a light chain variable domain;
$C_L$ represents a domain from a light chain constant region, such as Ckappa;
$V_2$ represents a dsFv;
wherein the polypeptide chain of formula (Ic) comprises a protein A binding domain; and
wherein the polypeptide chain of formula (IIc) does not bind protein A.

In such embodiment, $V_2$, i.e. the dsFv of $V_2$, does not bind protein A. In one embodiment, the polypeptide chain of formula (Ic) comprises only one protein A binding domain present in $V_H$ or $CH_2$-$CH_3$. In another embodiment, the polypeptide chain of formula (Ic) comprises two protein A binding domains present in $V_H$ and $CH_2$-$CH_3$ respectively.

In one embodiment of the multi-specific antibody of the invention,
$V_L$ and $V_H$ comprise an antigen binding site that binds to human IL-17A and/or human IL-17F,
$V_1$ comprises an antigen binding site that binds to human serum albumin, and
$V_2$ comprises an antigen binding site that binds to human IL-13.

In one embodiment, $V_L$ comprises the sequence given in SEQ ID NO:1 for CDR-L1, the sequence given in SEQ ID NO:2 for CDR-L2 and the sequence given in SEQ ID NO:3 for CDR-L3; $V_H$ comprises the sequence given in SEQ ID NO:4 for CDR-H1, the sequence given in SEQ ID NO:5 for CDR-H2 and the sequence given in SEQ ID NO:6 for CDR-H3.

In one embodiment, $V_1$ comprises a light chain variable region comprising the sequence given in SEQ ID NO:39 for CDR-L1, the sequence given in SEQ ID NO:40 for CDR-L2 and the sequence given in SEQ ID NO:41 for CDR-L3; and a heavy chain variable region comprising the sequence given in SEQ ID NO:42 for CDR-H1, the sequence given in SEQ ID NO:43 for CDR-H2 and the sequence given in SEQ ID NO:44 for CDR-H3.

In one embodiment, $V_2$ comprises a light chain variable region comprising the sequence given in SEQ ID NO:15 for CDR-L1, the sequence given in SEQ ID NO:16 for CDR-L2 and the sequence given in SEQ ID NO:17 for CDR-L3; and a heavy chain variable region comprising the sequence given in SEQ ID NO:18 for CDR-H1, the sequence given in SEQ ID NO:19 for CDR-H2 and the sequence given in SEQ ID NO:20 for CDR-H3;

In one embodiment, $V_L$ comprises the sequence given in SEQ ID NO:7 and $V_H$ comprises the sequence given in SEQ ID NO:9.

In one embodiment, $V_1$ comprises a light chain variable region comprising the sequence given in SEQ ID NO:45 and a heavy chain variable region comprising the sequence given in SEQ ID NO:46.

In one embodiment, $V_1$ comprises a light chain variable region comprising the sequence given in SEQ ID NO:49 and a heavy chain variable region comprising the sequence given in SEQ ID NO:50.

In one embodiment, the light chain variable region and heavy chain variable region of $V_1$ are connected by a linker, said linker comprising the sequence given in SEQ ID NO:68.

In one embodiment, $V_1$ is a scFv comprising the sequence given in SEQ ID NO:53 or a dsscFv comprising the sequence given in SEQ ID NO:55.

In one embodiment, $V_2$ comprises a light chain variable region comprising the sequence given in SEQ ID NO:27 and a heavy chain variable region comprising the sequence given in SEQ ID NO:28.

In one embodiment, $V_2$ comprises a light chain variable region comprising the sequence given in SEQ ID NO:31 and a heavy chain variable region comprising the sequence given in SEQ ID NO:32.

In one embodiment, the light chain variable region and heavy chain variable region of $V_2$ are connected by a linker, said linker comprising the sequence given in SEQ ID NO:66.

In one embodiment, $V_2$ is a scFv comprising the sequence given in SEQ ID NO:35 or a dsscFv comprising the sequence given in SEQ ID NO:37.

In one embodiment, X is a linker comprising the sequence given in SEQ ID NO:67.

In one embodiment, Y is a linker comprising the sequence given in SEQ ID NO:65.

In one embodiment, the polypeptide chain of formula (Ia) comprises the sequence given in SEQ ID NO:57 or SEQ ID NO: 59.

In one embodiment, the polypeptide chain of formula (IIa) comprises the sequence given in SEQ ID NO:61 or SEQ ID NO: 63.

In one embodiment, the polypeptide chain of formula (Ia) comprises the sequence given in SEQ ID NO:59 and the polypeptide chain of formula (IIa) comprises the sequence given in SEQ ID NO: 63.

It will be appreciated that one or more amino acid substitutions, additions and/or deletions may be made to the sequences provided by the present invention without significantly altering the ability of the antibody to bind to an antigen and neutralise its biological activity. The effect of any amino acid substitutions, additions and/or deletions can be readily tested by one skilled in the art, for example by using the methods described herein, particularly those illustrated in the Examples, to determine antigen binding and inhibition of biological activity.

Accordingly, the present invention provides a multi-specific antibody comprising CDRs as defined by the sequences given in SEQ ID NOs:1, 2, 3, 4, 5, 6, 15, 16, 17, 18, 19, 20, 39, 40, 41, 42, 43 and 44, in which one or more amino acids in one or more of the CDRs has been substituted with another amino acid, for example a similar amino acid as defined herein below.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains). Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656,).

In one embodiment, the CDRs of the multi-specific antibody comprise sequences which have at least 70%, 80%, 90%, 95% or 98% identity or similarity to the sequences given in SEQ ID NOs:1, 2, 3, 4, 5, 6, 15, 16, 17, 18, 19, 20, 39, 40, 41, 42, 43 and 44.

In one embodiment, $V_L$ comprises a sequence which has at least 70%, 80%, 90%, 95% or 98% identity or similarity to the sequence given in SEQ ID NO:7 and $V_H$ comprises a sequence which has at least 70%, 80%, 90%, 95% or 98% identity or similarity to the sequence given in SEQ ID NO:9.

In one embodiment, $V_1$ comprises a light chain variable region comprising a sequence which has at least 70%, 80%, 90%, 95% or 98% identity or similarity to the sequence given in SEQ ID NO:45 and/or a heavy chain variable region comprising a sequence which has at least 70%, 80%, 90%, 95% or 98% identity or similarity to the sequence given in SEQ ID NO:46.

In one embodiment, $V_1$ comprises a light chain variable region comprising a sequence which has at least 70%, 80%, 90%, 95% or 98% identity or similarity to the sequence given in SEQ ID NO:49 and/or a heavy chain variable region comprising a sequence which has at least 70%, 80%, 90%, 95% or 98% identity or similarity to the sequence given in SEQ ID NO:50.

In one embodiment, the light chain variable region and heavy chain variable region of $V_1$ are connected by a linker, said linker comprising a sequence which has at least 70%, 80%, 90%, 95% or 98% identity or similarity to the sequence given in SEQ ID NO:68.

In one embodiment, $V_1$ is a scFv comprising a sequence which has at least 70%, 80%, 90%, 95% or 98% identity or similarity to the sequence given in SEQ ID NO:53 or a dsscFv comprising a sequence which has at least 70%, 80%, 90%, 95% or 98% identity or similarity to the sequence given in SEQ ID NO:55.

In one embodiment, $V_2$ comprises a light chain variable region comprising a sequence which has at least 70%, 80%, 90%, 95% or 98% identity or similarity to the sequence given in SEQ ID NO:27 and/or a heavy chain variable region comprising a sequence which has at least 70%, 80%, 90%, 95% or 98% identity or similarity to the sequence given in SEQ ID NO:28.

In one embodiment, $V_2$ comprises a light chain variable region comprising a sequence which has at least 70%, 80%, 90%, 95% or 98% identity or similarity to the sequence given in SEQ ID NO:31 and/or a heavy chain variable region comprising a sequence which has at least 70%, 80%, 90%, 95% or 98% identity or similarity to the sequence given in SEQ ID NO:32.

In one embodiment, the light chain variable region and heavy chain variable region of $V_2$ are connected by a linker, said linker comprising a sequence which has at least 70%, 80%, 90%, 95% or 98% identity or similarity to the sequence given in SEQ ID NO:66.

In one embodiment, $V_2$ is a scFv comprising a sequence which has at least 70%, 80%, 90%, 95% or 98% identity or similarity to the sequence given in SEQ ID NO:35 or a dsscFv comprising a sequence which has at least 70%, 80%, 90%, 95% or 98% identity or similarity to the sequence given in SEQ ID NO:37.

In one embodiment, X is a linker comprising a sequence which has at least 70%, 80%, 90%, 95% or 98% identity or similarity to the sequence given in SEQ ID NO:67.

In one embodiment, Y is a linker comprising a sequence which has at least 70%, 80%, 90%, 95% or 98% identity or similarity to the sequence given in SEQ ID NO:65.

In one embodiment, the polypeptide chain of formula (Ia) comprises a sequence which has at least 70%, 80%, 90%, 95% or 98% identity or similarity to the sequence given in SEQ ID NO:57 or SEQ ID NO: 59.

In one embodiment, the polypeptide chain of formula (IIa) comprises a sequence which has at least 70%, 80%, 90%, 95% or 98% identity or similarity to the sequence given in SEQ ID NO:61 or SEQ ID NO: 63.

In one embodiment, the polypeptide chain of formula (Ia) comprises a sequence which has at least 70%, 80%, 90%, 95% or 98% identity or similarity to the sequence given in SEQ ID NO:59 and the polypeptide chain of formula (IIa) comprises a sequence which has at least 70%, 80%, 90%, 95% or 98% identity or similarity to the sequence given in SEQ ID NO: 63.

Epitope

An epitope is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

One can easily determine whether an antibody binds to the same epitope as, or competes for binding with, a reference antibody by using routine methods known in the art. For example, to determine if a test antibody binds to the same epitope as a reference antibody of the invention, the reference antibody is allowed to bind to a protein or peptide under saturating conditions. Next, the ability of a test antibody to bind to the protein or peptide is assessed. If the test antibody is able to bind to the protein or peptide following saturation binding with the reference antibody, it can be concluded that the test antibody binds to a different epitope than the reference antibody. On the other hand, if the test antibody is not able to bind to protein or peptide following saturation binding with the reference antibody, then the test antibody may bind to the same epitope as the epitope bound by the reference antibody of the invention.

To determine if an antibody competes for binding with a reference antibody, the above-described binding methodology is performed in two orientations. In a first orientation, the reference antibody is allowed to bind to a protein/peptide under saturating conditions followed by assessment of binding of the test antibody to the protein/peptide molecule. In a second orientation, the test antibody is allowed to bind to the protein/peptide under saturating conditions followed by assessment of binding of the reference antibody to the protein/peptide. If, in both orientations, only the first (saturating) antibody is capable of binding to the protein/peptide, then it is concluded that the test antibody and the reference antibody compete for binding to the protein/peptide. As will be appreciated by the skilled person, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50%, 75%, 90% or even 99% as measured in a competitive binding assay (see, e.g., Junghans et al., Cancer Res, 1990: 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Antibodies may compete for binding to IL-17A or IL-17F with, or bind to the same epitope as, a multi-specific antibody which comprises a CDR-L1/CDR-L2/CDR-L3/CDR-H1/CDR-H2/CDR-H3 sequence combination of SEQ ID NOs: 1/2/3/4/5/6.

Antibodies may compete for binding to IL-13 with, or bind to the same epitope as, a multi-specific antibody which comprises a CDR-L1/CDR-L2/CDR-L3/CDR-H1/CDR-H2/CDR-H3 sequence combination of SEQ ID NOs: 15/16/17/18/19/20.

Antibodies may compete for binding to serum albumin with, or bind to the same epitope as, a multi-specific antibody which comprises a CDR-L1/CDR-L2/CDR-L3/CDR-H1/CDR-H2/CDR-H3 sequence combination of SEQ ID NOs: 39/40/41/42/43/44.

Effector Molecules

If desired, a multi-specific antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03031581. Alternatively, where the effector molecule is a protein or polypeptide the linkage may be achieved using recombinant DNA procedures, for example as described in WO 86/01533 and EP 0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, *pseudomonas* exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiosta- tin or endostatin, or, a biological response modifier such as a lymphokine, interleukin-1 (IL-1), interleukin-2 (IL-2), granulocyte macrophage colony stimulating factor (GM- CSF), granulocyte colony stimulating factor (G-CSF), nerve growth factor (NGF) or other growth factor and immuno- globulins.

Other effector molecules may include detectable sub- stances useful for example in diagnosis. Examples of detect- able substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741, 900 for metal ions which can be conjugated to antibodies for use as diagnostics. Suitable enzymes include horseradish peroxidase, alkaline phosphatase, beta-galactosidase, or ace- tylcholinesterase; suitable prosthetic groups include strepta- vidin, avidin and biotin; suitable fluorescent materials include umbelliferone, fluorescein, fluorescein isothiocya- nate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}I$, $^{131}I$, $^{111}n$ and $^{99}Tc$.

In another example the effector molecule may increase the half-life of the antibody in vivo, and/or reduce immunoge- nicity of the antibody and/or enhance the delivery of an antibody across an epithelial barrier to the immune system. Examples of suitable effector molecules of this type include polymers, albumin, albumin binding proteins or albumin binding compounds such as those described in WO 05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include option- ally substituted straight or branched chain poly(ethylenegly- col), poly(propyleneglycol) poly(vinylalcohol) or deriva- tives thereof, especially optionally substituted poly (ethyleneglycol) such as methoxypoly(ethyleneglycol) or derivatives thereof.

Specific naturally occurring polymers include lactose, amylose, dextran, glycogen or derivatives thereof.

"Derivatives" as used herein is intended to include reac- tive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly (ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO 98/25971). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules may be covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disul- phide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, AL, USA) or may be prepared from commer- cially available starting materials using conventional chemi- cal procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment or diFab which is PEGylated, i.e. has PEG (poly (ethyleneglycol)) covalently attached thereto, e.g. according to the method disclosed in EP 0948544 or EP 1090037 [see also "Poly(ethyleneglycol) Chemistry, Biotechnical and Biomedical Applications", 1992, J. Milton Harris (ed), Ple- num Press, New York, "Poly(ethyleneglycol) Chemistry and Biological Applications", 1997, J. Milton Harris and S. Zalipsky (eds), American Chemical Society, Washington DC and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethylenegly-col) polymer having a molecular weight of approximately 20,000 Da. The total molecular weight of the PEG attached to the Fab fragment may therefore be approximately 40,000 Da.

In one embodiment the multi-specific antibody is not attached an effector molecule.

Polynucleotides/Vectors/Host Cells

The present invention also provides an isolated polynucle-otide encoding a polypeptide chain of an IL-13/IL-17AF multi-specific antibody molecule.

A variant polynucleotide may comprise 1, 2, 3, 4, 5, up to 10, up to 20, up to 30, up to 40, up to 50, up to 75 or more nucleic acid substitutions and/or deletions from the sequences given in the sequence listing. Generally, a variant has 1-20, 1-50, 1-75 or 1-100 substitutions and/or deletions.

Suitable variants may be at least about 70% homologous to a polynucleotide of any one of nucleic acid sequences disclosed herein, typically at least about 80 or 90% and more suitably at least about 95%, 97% or 99% homologous thereto. Variants may retain at least about 90%, 91%, 92%, 93%, 94%, 95%, 96%, 97%, 98% or 99% identity. Variants typically retain about 60%-about 99% identity, about 80%-about 99% identity, about 90%-about 99% identity or about 95%-about 99% identity. Homology and identity at these levels is generally present at least with respect to the coding regions of the polynucleotides. Methods of measuring homology are well known in the art and it will be understood by those of skill in the art that in the present context, homology is calculated on the basis of nucleic acid identity. Such homology may exist over a region of at least about 15, at least about 30, for instance at least about 40, 60, 100, 200 or more contiguous nucleotides (depending on the length). Such homology may exist over the entire length of the unmodified polynucleotide sequence.

The homologue may differ from a sequence in the relevant polynucleotide by less than about 3, 5, 10, 15, 20 or more mutations (each of which may be a substitution, deletion or insertion). For example, the homologue may differ by 3-50 mutations, often 3-20 mutations. These mutations may be measured over a region of at least 30, for instance at least about 40, 60 or 100 or more contiguous nucleotides of the homologue.

The DNA sequence of the present invention may com-prise synthetic DNA, for instance produced by chemical processing, cDNA, genomic DNA or any combination thereof.

General methods by which the vectors may be con-structed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publish-ing.

Also provided is a host cell comprising one or more cloning or expression vectors comprising one or more DNA sequences encoding an IL-13/IL-17AF multi-specific anti-body. Any suitable host cell/vector system may be used for expression of the DNA sequences encoding the IL-13/IL-17AF multi-specific antibody. Bacterial, for example E. coli, and other microbial systems may be used or eukaryotic, for example mammalian, host cell expression systems may also be used. Suitable mammalian host cells include CHO cells.

The present invention also provides a process for the production of an IL-13/IL-17AF multi-specific antibody, comprising culturing a host cell containing a vector under conditions suitable for expression of protein from DNA encoding the IL-13/IL-17AF multi-specific antibody, and isolating the IL-13/IL-17AF multi-specific antibody.

Production of Multispecific Antibodies

There are a number of approaches for generating multi-specific, notably bi-specific antibodies. Morrison et al (Co-loma and Morrison 1997, Nat Biotechnol. 15, 159-163) describes the fusion of single chain variable fragments (scFv) to whole antibodies, e.g. IgG. Schoonjans et al., 2000, Journal of Immunology, 165, 7050-7057, describes the fusion of scFv to antibody Fab fragments. WO2015/197772 describes the fusion of disulphide stabilised scFv (dsscFv) to Fab fragments.

Standard approaches described in the prior art comprise the expression in a host cell of at least two polypeptides, each one coding for a heavy chain (HC) or a light chain (LC) of a whole antibody or antigen binding fragment thereof e.g. a Fab, to which an additional antigen binding fragment of an antibody can be fused to the N- and/or C-terminal position of the heavy chain and/or the light chain. When trying to recombinantly produce such multi-specific antibodies by expressing two (one light chain and one heavy chain to form an appended Fab) or four polypeptides (two light chains and two heavy chains to form an appended IgG), it usually requires expressing the light chain in excess over the heavy chain, in order to ensure the proper folding of the heavy chain upon assembly with its corresponding light chain. In particular, the $CH_1$ (domain 1 of the heavy chain constant region) is prevented from folding on itself by BIP proteins, which can be displaced by a corresponding LC; therefore, the correct folding of the $CH_1$/HC is dependent on the availability of its corresponding LC (Lee et al., 1999, Molecular Biology of the Cell, Vol. 10, 2209-2219).

We have observed that those methods of expressing multi-specific antibodies may result in the production of the light chain in excess over the heavy chain, which remains in the host cell harvest, and that the excess of light chain tends to form dimeric complexes (or "LC dimers") which are present as a by-product of the production process with the desired multi-specific antibody, notably monomeric, and thus need to be purified away.

Importantly, the technical problem associated with the formation of dimers of light chains, when fused on N- and/or C-terminal to additional antigen binding fragment(s), has not been identified so far, and the commonly used analytical methods have not allowed the detection and quantification of those appended LC dimers amongst the heterogenous prod-ucts of the production process. This may result in a signifi-cant bias when estimating the amount of the products using standard analytical methods.

Thus, there is a need to improve multi-specific antibodies and methods of production thereof, which allow the isola-tion and removal of the appended LC dimers easily and efficiently at the earliest steps of the production process, and thus improve the yield of the protein of interest for use in therapy, which is the multi-specific antibody, in particular in its monomeric form.

The multi-specific antibodies of the present invention have been engineered to provide improved multi-specific antibodies with equivalent functionality and stability, whilst increasing the yield of "multi-specific antibody" material, notably monomeric, obtained after purification, notably after a one-step purification comprising a protein A affinity chromatography.

Advantageously, the multi-specific antibodies of the present disclosure can be more efficiently purified with a purification method which is improved over the methods commonly used in the prior art, notably in that the improved method comprises fewer steps, which is cost and time effective at the industrial scale. In particular, the multi-specific antibodies of the present disclosure maximise the quantity of proteins of interest (i.e, the correct multi-specific antibody format) obtained after a one-step purification method comprising a protein A affinity chromatography, whereby the purification of the multi-specific antibodies of interest and the removal of the appended LC dimers occur concurrently. Advantageously, the methods of production and purification of the multi-specific antibodies of the present disclosure do not require an additional purification step to capture the free, unbound light chains in excess, notably the appended LC dimers.

Protein A

Protein A is a 42 kDa surface protein originally found in the cell wall of the bacteria *Staphylococcus aureus*. Protein A has been widely used to detect, quantify and purify immunoglobulins. Protein A has been reported to bind the Fab portion derived from the VH3 family antibodies, and the Fc gamma region in the constant region portion of IgG (between the $CH_2$ and $CH_3$ domains). The crystal structure of the complex formed by protein A and the Fab has been described for example in Graille et al., 2000, PNAS, 97(10): 5399-5404.

In the context of the present disclosure, protein A encompasses natural protein A and any variant or derivative thereof, to the extent that the protein A variant or derivative maintains its ability to bind VH3 domains and/or Fc gamma domains.

The polypeptide chain of formula (I) of the present invention comprises a protein A binding domain. In one embodiment, the polypeptide chain of formula (I) comprises one, two or three protein A binding domains.

"Protein A binding domain" as employed herein is intended to refer to a binding domain which specifically binds to protein A. A Protein A binding domain may refer to a VH3 domain or a portion of a VH3 domain which binds protein A, i.e. which comprises a protein A binding interface. The portion of a VH3 domain which binds protein A does not comprise the CDRs of the VH3 domain, i.e. the protein A binding interface of the VH3 does not involve the CDRs; consequently, it will be understood that a protein A binding domain does not compete with an antigen binding domain as disclosed in the present application.

In one embodiment, the polypeptide chain of formula (I) comprises a protein A binding domain which is present in $V_H$ and/or $CH_2$-$CH_3$ and/or $V_1$. In one embodiment, the polypeptide chain of formula (I) comprises one, two or three protein A binding domains, which is/are present in $V_H$ and/or $CH_2$-$CH_3$ and/or V1. In one embodiment, the polypeptide chain of formula (I) comprises only one protein A binding domain which is present in $V_H$ or $V_1$. In one embodiment, s is 0, t is 0 and the polypeptide chain of formula (I) comprises only one protein A binding domain which is present in $V_H$ or $V_1$. In one embodiment, the polypeptide chain of formula (I) comprises only one protein A binding domain which is present in $V_H$. In one embodiment, s is 0, t is 0, p is 0, and the polypeptide chain of formula (I) comprises only one protein A binding domain which is present in $V_H$. In one embodiment, the polypeptide chain of formula (I) comprises only one protein A binding domain which is present in $V_1$. In one embodiment, s is 0, t is 0, p is 1, and the polypeptide chain of formula (I) comprises only one protein A binding domain which is present in $V_1$.

In one embodiment, the polypeptide chain of formula (I) comprises two protein A binding domains. In one embodiment, the polypeptide chain of formula (I) comprises two protein A binding domains which are present in $V_H$ and $CH_2$-$CH_3$ respectively. In another embodiment, the polypeptide chain of formula (I) comprises two protein A binding domains which are present in $V_H$ and $V_1$ respectively. In another embodiment, the polypeptide chain of formula (I) comprises two protein A binding domains which are present in $CH_2$-$CH_3$ and V, respectively.

In one embodiment, the polypeptide chain of formula (I) comprises three protein A binding domains, each one being present in $V_H$, $CH_2$-$CH_3$ and $V_1$.

Natural protein A can interact in particular with the Fc gamma region, in the constant region portion of IgG. More particularly, protein A can interact with a binding domain between the $CH_2$ and the $CH_3$. In one embodiment when s is 1, t is 1, both $CH_2$ and $CH_3$ are naturally occurring domains of the IgG class.

In some embodiments, the protein A binding domain(s) comprise(s) or consist(s) of a VH3 domain or variant thereof which binds protein A. In some embodiments, the protein A binding domain(s) comprise(s) or consist(s) of a naturally occurring VH3 domain. In some embodiments, a variant of a VH3 domain which binds protein A is a variant of a naturally occurring VH3 domain, said naturally occurring VH3 domain being unable to bind protein A.

The polypeptide chain of formula (II) of the present disclosure does not bind protein A. In one embodiment, the binding domain of $V_2$ does not bind protein A.

In some embodiments, $V_2$ comprises or consists of a VH1 and/or a VH2 and/or a VH4 and/or a VH5 and/or a VH6 and does not comprise a VH3 domain. In some embodiments, $V_2$ comprises or consists of a VH3 domain or variant thereof which does not bind protein A. In some embodiments, $V_2$ comprises or consists of a naturally occurring VH3 domain being unable to bind protein A. In some embodiments, a variant of a VH3 domain which does not bind protein A is a variant of a naturally occurring VH3, said naturally occurring VH3 domain being able to bind protein A.

Human VH3 germline genes and VH3 domains (or frameworks) have been well characterized. Many of the naturally occurring VH3 domains have the capacity to bind protein A but certain naturally occurring VH3 domains do not have the capacity to bind protein A (see Roben et al., 1995, J Immunol.;154(12):6437-6445).

A VH3 domain for use in the present disclosure can be obtained by several methods. In one embodiment, a VH3 domain for use in the present disclosure is a naturally occurring VH3 domain, selected for its ability or inability to bind protein A, depending on its position within the polypeptide (I) and/or (II) of the disclosure. For example, a panel of antibodies may be generated against an antigen of interest by immunisation of a non-human animal, then humanised, and the humanised antibodies may be screened and selected based on their ability or inability to bind protein A via the humanised VH3 domain, for example against a protein A affinity column. Alternatively, display technologies (e.g. phage display, yeast display, ribosome display, bacterial display, mammalian cell surface display, mRNA display, DNA display) may be used to screen antibody libraries and select antibodies comprising a VH3 domain which binds, notably via a protein A binding interface which does not involve the CDRs, or does not bind protein A.

Alternatively, a VH3 domain for use in the present disclosure is a variant of a naturally occurring VH3. In one embodiment, a VH3 variant comprises a sequence of a naturally occurring VH3 able to bind protein A, and further comprising at least one amino acid mutation, which abolishes its ability to bind protein A. In one embodiment, a VH3 variant which binds protein A comprises a sequence of a naturally occurring VH3 unable to bind protein A, and further comprises at least one amino acid mutation. In such embodiment, the mutation(s) is/are responsible for the VH3 domain to gain the ability to bind protein A, i.e. the mutation(s) contribute(s) to the generation of a protein A binding domain which was not naturally present.

In one embodiment, a VH3 variant comprises 1, 2, 3, 4, 5, 6, 7, 8, 9, 10, 11, or 12 amino acid mutations. In one embodiment, a VH3 variant comprises a mutation at the position 15, 17, 19, 57, 59, 64, 65, 66, 68, 70, 81 or 82 on the VH3, numbering according to Kabat and as described for example in Graille et al., 2000, PNAS, 97(10): 5399-5404). The mutation may be a substitution, a deletion, or an insertion. In one embodiment, the VH3 variant comprises a substitution at the position 15, 17, 19, 57, 59, 64, 65, 66, 68, 70, 81 or 82 on the VH3, numbering according to Kabat.

Naturally occurring VH1, VH2, VH4, VH5 and VH6 do not bind protein A. In one embodiment, a $V_H$ domain which does not bind protein A is a VH1. In one embodiment, a $V_H$ domain which does not bind protein A is a VH2. In one embodiment, a $V_H$ domain which does not bind protein A is a VH4. In one embodiment, a $V_H$ domain which does not bind protein A is a VH5. In one embodiment, a $V_H$ domain which does not bind protein A is a VH6.

Pharmaceutical Compositions, Dosages and Dosage Regimes

A multi-specific antibody of the invention may be provided in a pharmaceutical composition. The pharmaceutical composition will normally be sterile and will typically include a pharmaceutically acceptable carrier and/or adjuvant. A pharmaceutical composition of the present invention may additionally comprise a pharmaceutically acceptable adjuvant and/or carrier.

As used herein, "pharmaceutically acceptable carrier" includes any and all solvents, dispersion media, coatings, antibacterial and antifungal agents, isotonic and absorption delaying agents, and the like that are physiologically compatible. The carrier may be suitable for parenteral, e.g. intravenous, intramuscular, intradermal, intraocular, intraperitoneal, subcutaneous, spinal or other parenteral routes of administration, for example by injection or infusion. Alternatively, the carrier may be suitable for non-parenteral administration, such as a topical, epidermal or mucosal route of administration. The carrier may be suitable for oral administration. Depending on the route of administration, the modulator may be coated in a material to protect the compound from the action of acids and other natural conditions that may inactivate the compound.

The pharmaceutical compositions of the invention may include one or more pharmaceutically acceptable salts. A "pharmaceutically acceptable salt" refers to a salt that retains the desired biological activity of the parent compound and does not impart any undesired toxicological effects. Examples of such salts include acid addition salts and base addition salts.

Pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. In many cases, it will be desirable to include isotonic agents, for example, sugars, polyalcohols such as mannitol, sorbitol, or sodium chloride in the composition.

Therapeutic compositions typically must be sterile and stable under the conditions of manufacture and storage. The composition can be formulated as a solution, microemulsion, liposome, or other ordered structure suitable to high drug concentration.

Pharmaceutical compositions of the invention may comprise additional active ingredients.

Also within the scope of the present invention are kits comprising antibodies or modulatory agents of the invention and instructions for use. The kit may further contain one or more additional reagents, such as an additional therapeutic or prophylactic agent as discussed above.

The modulators and/or antibodies of the invention or formulations or compositions thereof may be administered for prophylactic and/or therapeutic treatments.

In therapeutic applications, compounds are administered to a subject already suffering from a disorder or condition as described above, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as a "therapeutically effective amount".

In prophylactic applications, formulations are administered to a subject at risk of a disorder or condition as described above, in an amount sufficient to prevent or reduce the subsequent effects of the condition or one or more of its symptoms. An amount adequate to accomplish this is defined as a "prophylactically effective amount". Effective amounts for each purpose will depend on the severity of the disease or injury as well as the weight and general state of the subject.

A subject for administration may be a human or non-human animal. The term "non-human animal" includes all vertebrates, e.g., mammals and non-mammals, such as non-human primates, sheep, dogs, cats, horses, cows, chickens, amphibians, reptiles, etc. Administration to humans is typical.

An antibody/modulator or pharmaceutical composition of the invention may be administered via one or more routes of administration using one or more of a variety of methods known in the art. As will be appreciated by the skilled artisan, the route and/or mode of administration will vary depending upon the desired results. Examples of routes of administration for compounds or pharmaceutical compositions of the invention include intravenous, intramuscular, intradermal, intraocular, intraperitoneal, subcutaneous, spinal or other parenteral routes of administration, for example by injection or infusion. The phrase "parenteral administration" as used herein means modes of administration other than enteral and topical administration, usually by injection. Alternatively, antibody/modulatory agent or pharmaceutical composition of the invention can be administered via a non-parenteral route, such as a topical, epidermal or mucosal route of administration. The antibody/modulatory agent or pharmaceutical composition of the invention may be for oral administration.

A suitable dosage of an antibody/modulatory agent or pharmaceutical composition of the invention may be determined by a skilled medical practitioner. Actual dosage levels of the active ingredients in the pharmaceutical compositions of the present invention may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A suitable dose may be, for example, in the range of from about 0.01 µg/kg to about 1000 mg/kg body weight, typically from about 0.1 µg/kg to about 100 mg/kg body weight, of the patient to be treated. For example, a suitable dosage may be from about 1 µg/kg to about 10 mg/kg body weight per day or from about 10 µg/kg to about 5 mg/kg body weight per day.

Dosage regimens may be adjusted to provide the optimum desired response (e.g., a therapeutic response). For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Administration may be in single or multiple doses. Multiple doses may be administered via the same or different routes and to the same or different locations. Alternatively, doses can be via a sustained release formulation, in which case less frequent administration is required. Dosage and frequency may vary depending on the half-life of the antagonist in the patient and the duration of treatment desired.

As mentioned above, modulators/antibodies or pharmaceutical compositions of the invention may be co-administered with one or other more other therapeutic agents.

Combined administration of two or more agents may be achieved in a number of different ways. Both may be administered together in a single composition, or they may be administered in separate compositions as part of a combined therapy. For example, the one may be administered before, after or concurrently with the other.

Therapeutic Indications

Antibodies of present invention may be used in treating, preventing or ameliorating any condition that is associated with IL-13 and/or IL-17A and/or IL-17F activity; for example, any condition which results in whole or in part from signalling through an IL-13, IL-17A and/or IL-17F receptor.

Such diseases include primary and metastatic cancers, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), solid tumors arising from hematopoietic malignancies such as leukemias, and lymphomas (both Hodgkin's and non-Hodgkin's lymphomas), rheumatoid arthritis, osteoarthritis, juvenile chronic arthritis, septic arthritis, Lyme arthritis, psoriatic arthritis, reactive arthritis, spondyloarthropathy, systemic lupus erythematosus, ulcerative colitis, inflammatory bowel disease, insulin dependent diabetes mellitus, thyroiditis, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein *purpurea*, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, Addison's disease, sporadic, polyglandular deficiency type I and polyglandular deficiency type II, Schmidt's syndrome, adult (acute) respiratory distress syndrome, alopecia, alopecia areata, arthropathy, Reiter's disease, psoriatic arthropathy, ulcerative colitic arthropathy, enteropathic synovitis, *chlamydia, yersinia* and *salmonella* associated arthropathy, atheromatous disease/arteriosclerosis, atopic allergy, autoimmune bullous disease, pemphigus vulgaris, pemphigus *foliaceus*, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, acquired immunodeficiency related diseases, hepatitis B, hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis *nigricans*, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjorgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcoholinduced liver injury, choleosatatis, idiosyncratic liver disease, drug-induced hepatitis, non-alcoholic steatohepatitis, allergy, group B streptococci (GBS) infection, mental disorders, depression, schizophrenia, Th2 Type and Th1 Type mediated diseases, acute and chronic pain, different forms of pain, cancers, lung cancer, breast cancer, stomach cancer, bladder cancer, colon cancer, pancreatic cancer, ovarian cancer, prostate cancer, rectal cancer, hematopoietic malignancies, leukemia, lymphoma, Abetalipoprotemia, acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcoholinduced hepatitis, allergic conjunctivitis, allergic contact dermatitis, allergic rhinitis (including seasonal allergic rhinitis), non-allergic rhinitis, allograft rejection, alpha-l-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aortic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, CreutzfeldtJakob disease, culture negative sepsis, cystic fibrosis, cytokine therapy associated disorders, dementia pugilistica, demyelinating diseases, dengue hemorrhagic fever, dermatitis, dermatologic conditions, diabetes, diabetes mellitus, diabetic ateriosclerotic disease, diffuse Lewy body disease, dilated congestive cardiomyopathy, disorders of the basal ganglia, Down's syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallervorden-Spatz disease, Hashimoto's thyroiditis, hay fever, heart transplant rejection, hemachromatosis, hemodialysis, hemolytic uremic syndrome/thrombolytic thrombocytopenic purpura, hemorrhage, hepatitis A, His bundle arrythmias, HIV infection/HIV neuropathy, Hodgkin's disease, hyperkinetic movement disorders, hypersensitity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, *legionella*, leishmaniasis, leprosy, lesions of the corticospinal system, lipedema, liver transplant rejection, lymphederma, malaria, malignamt lymphoma, malignant histiocytosis, malignant melanoma, meningitis, meningococcemia, metabolic/idiopathic, migraine headache, mitochondrial multi. system disorder, mixed connective tissue disease, monoclonal gammopathy, multiple myeloma, multiple systems degenerations (Mencel Dejerine-Thomas Shi-Drager and Machado-Joseph), *Mycobacterium avium intracellulare, Mycobacterium tuberculosis*, myelodyplastic syndrome, myocardial infarction, myocardial ischemic disorders, nasopharyngeal carcinoma, neonatal chronic lung disease, nephritis, nephrosis, neurodegenerative diseases, neurogenic muscular atrophies, neutropenic fever, nonhodgkins lymphoma, occlusion of the abdominal aorta and its branches, occlusive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, *Pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, progressive supranucleo palsy, primary pulmonary hypertension, radiation therapy, Raynaud's phenomenon and disease, Raynoud's disease, Refsum's disease, regular narrow QRS tachycardia, renovascular hypertension, reperfusion injury, restrictive cardiomyopathy, sarcomas, senile chorea, senile dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, subacute sclerosing panencephalitis, syncope, syphilis of the cardiovascular system, systemic anaphalaxis, systemic inflammatory response syndrome, systemic onset juvenile rheumatoid arthritis, T-cell or FAB ALL telangiectasia, thromboangitis obliterans, thrombocytopenia, toxicity, transplants, trauma/hemorrhage, type Ill hypersensitivity reactions, type IV hypersensitivity, unstable angina, uremia, urosepsis, valvular heart diseases, varicose veins, vasculitis, venous diseases, venous thrombosis, ventricular fibrillation, viral and fungal infections, vital encephalitis/aseptic meningitis, vitalassociated hemaphagocytic syndrome, Wernicke-Korsakoff syndrome, Wilson's disease, xenograft rejection of any organ or tissue, acute coronary syndromes, acute idiopathic polyneuritis, acute inflammatory demyelinating polyradiculoneuropathy, acute ischemia, adult Still's disease, anaphylaxis, antiphospholipid antibody syndrome, aplastic anemia, atopic eczema, atopic dermatitis, autoimmune dermatitis, autoimmune disorder associated with *streptococcus* infection, autoimmune enteropathy, autoimmune hearing loss, autoimmune lymphoproliferative syndrome (ALPS), autoimmune myocarditis, autoimmune premature ovarian failure, blepharitis, bronchiectasis, bullous pemphigoid, cardiovascular disease, catastrophicantiphospholipid syndrome, celiac disease, cervical spondylosis, chronic ischemia, cicatricial pemphigoid, clinically isolated syndrome (cis) with risk for multiple sclerosis, childhood onset psychiatric disorder, dacryocystitis, dermatomyositis, diabetic retinopathy, disk herniation, disk prolaps, drug induced immune hemolytic anemia, endometriosis, endophthalmitis, episcleritis, erythema multiforme, erythema multiforme major, gestational pemphigoid, Guillain-Barre syndrome (GBS), Hughes syndrome, idiopathic Parkinson's disease, idiopathic interstitial pneumonia, IgE-mediated allergy, immune hemolytic anemia, inclusion body myositis, infectious ocular inflammatory disease, inflammatory demyelinating disease, inflammatory heart disease, inflammatory kidney disease, IPF/UIP, iritis, keratitis, keratojuntivitis sicca, Kussmaul disease or Kussmaul-Meier disease, Landry's paralysis, Langerhan's cell histiocytosis, livedo *reticularis*, macular degeneration, microscopic polyangiitis, morbus bechterev, motor neuron disorders, mucous membrane pemphigoid, multiple organ failure, myasthenia gravis, myelodysplastic syndrome, myocarditis, nerve root disorders, neuropathy, non-A non-B hepatitis, optic neuritis, osteolysis, pauciarticular JRA, peripheral artery occlusive disease (PAOD), peripheral vascular disease (PVD), peripheral artery, disease (PAD), phlebitis, polyarteritis nodosa (or periarteritis nodosa), polychondritis, poliosis, polyarticular JRA, polyendocrine deficiency syndrome, polymyositis, polymyalgia rheumatica (PMR), primary Parkinsonism, prostatitis, pure red cell aplasia, primary adrenal insufficiency, recurrent neuromyelitis optica, restenosis, rheumatic heart disease, sapho (synovitis, acne, pustulosis, hyperostosis, and osteitis), secondary amyloidosis, shock lung, scleritis, sciatica, secondary adrenal insufficiency, silicone associated connective tissue disease, sneddon-wilkinson dermatosis, spondilitis ankylosans, Stevens-Johnson syndrome (SJS), temporal arteritis, toxoplasmic retinitis, toxic epidermal necrolysis, transverse myelitis, TRAPS (tumor necrosis factor receptor, type 1 allergic reaction, type II diabetes, urticaria, usual interstitial pneumonia (UIP), vasculitis, vernal conjunctivitis, viral retinitis, Vogt-Koyanagi-Harada syndrome (VKH syndrome), wet macular degeneration, or wound healing, aspirin sensitive asthma, atopic asthma, chronic hand eczema, allergic bronchopulmonary aspergillosis, coeliac disease, Churg-Strauss syndrome (periarteritis nodosa plus atopy), eosinophilic myalgia syndrome, hypereosinophilic syndrome, oedematous reactions including episodic angiodema, helminth infections, onchocercal dermatitis, Eosinophil-Associated Gastrointestinal Disorders, eosinophilic esophagitis, eosinophilic gastritis, eosinophilic gastroenteritis, eosinophilic enteritis, eosinophilic colitis, nasal micropolyposis and polyposis, food allergy, aspirin intolerance, and obstructive sleep apnoea, chronic asthma, Crohn's disease and endomyocardial fibrosis, cancer (e.g., glioblastoma (such as glioblastoma multiforme), non-Hodgkin's lymphoma (NHL)), fibrosis, inflammatory bowel disease, pulmonary fibrosis (including idiopathic pulmonary fibrosis (IPF) and pulmonary fibrosis secondary to sclerosis), COPD, and hepatic fibrosis.

Multi-specific antibodies of the present invention may be especially useful for treating or preventing atopic dermatitis, chronic hand eczema, nasal micropolyposis or polyposis, food allergy, or eosinophilic esophagitis. Thus, in one embodiment, a multi-specific antibody or pharmaceutical composition of the present invention is provided for use in a method of treatment of the human or animal body by therapy. In one embodiment, the multi-specific antibody or pharmaceutical composition is provided for use in a method of treating atopic dermatitis, chronic hand eczema, nasal micropolyposis or polyposis, food allergy, or eosinophilic esophagitis. In one embodiment, the invention provides a method of treating or preventing atopic dermatitis, chronic hand eczema, nasal micropolyposis or polyposis, food allergy, or eosinophilic esophagitis, comprising administering a therapeutically effective amount of a multi-specific antibody or pharmaceutical composition to a patient in need thereof.

The following Examples illustrate the invention.

EXAMPLES

Example 1. Generation and Selection of Therapeutic Anti-IL-13 Antibody CA650

Rats were immunised with either purified human IL-13 (Peprotech) or rat fibroblasts expressing human IL-13 (expressing approx 1 ug/ml in culture supernatant), or in some cases, a combination of the two. Following 3 to 6 shots, animals were sacrificed and PBMC, spleen, bone marrow and lymph nodes harvested. Sera was monitored for binding to human IL-13 in ELISA and also for the ability to neutralise hIL-13 in the HEK-293 IL-13R-STAT-6 reporter cell assay (HEK-Blue assay, Invivogen).

B cell cultures were set up and supernatants were first screened for their ability to bind hIL-13 in a bead-based assay in an Applied Biosystems FMAT assay. This was a homogeneous assay using biotinylated human IL-13 coated onto streptavidin beads and a goat anti-rat Fc-Cy5 conjugate as a reveal agent. Positives from this assay were then progressed into a HEK-293 IL-13R-STAT-6 reporter cell assay (HEK-Blue assay, Invivogen) to identify neutralisers. Neutralising supernatants were then profiled in the Biacore to estimate off-rate and also to characterise the mode of action of neutralisation. Neutralisation was categorised as either bin 1 or bin 2. Bin 1 represents an antibody that binds to human IL-13 and prevents binding of IL-13Rα1 and as a result also blocks IL-4R from binding. Bin 1 antibodies may also prevent binding of IL-13 to IL-13Rα2. Bin 2 represents an antibody that binds hIL-13 in such a way that allows binding to IL-13Rα1 but prevents recruitment of IL-4R into the complex. We were selecting antibodies that operated via bin 1.

Approx. 7500 IL-13-specific positives were identified in the primary FMAT screen from a total of 27×100-plate SLAM experiments. 800 wells demonstrated neutralisation in the HEK-blue assay. 170 wells had desirable Biacore profiles, i.e. bin 1 antibodies with off-rates $<5\times10^{-4}$ s$^{-1}$. Variable region cloning from these 170 wells was attempted and 160 successfully yielded fluorescent foci. 100 wells generated heavy and light chain variable region gene pairs following reverse transcription (RT)-PCR. These V-region genes were cloned as mouse IgG1 full-length antibodies and re-expressed in a HEK-293 transient expression system. Sequence analysis revealed that there were 27 unique families of anti-human IL-13 antibody. These recombinant antibodies were then retested for their ability to block recombinant hIL-13 (*E. coli*-derived and mammalian-derived), recombinant variant hIL-13 (R130Q) (*E. coli*-derived), natural wild type and variant hIL-13 (human donor-derived) and cynomolgus IL-13 (mammalian-derived) in the cell-based assay. Recombinant antibodies were also tested for their ability to bind variant human IL-13 (R130Q) and cynomolgus IL-13 in the Biacore. Following this characterisation, antibody families were selected to fulfil our criteria, i.e. sub-100 pM antibody with minimal drop-off in potency and affinity for all human and cynomolgus IL-13 preparations.

Based on neutralisation potency, affinity and donor content in humanised grafts (see below), humanised CA650 was selected for further progression.

Example 2. Antibody CA650 Humanisation

Antibody 650 was humanised by grafting the CDRs from the rat V-region onto human germline antibody V-region frameworks. In order to recover the activity of the antibody, a number of framework residues from the rat V-region were also retained in the humanised sequence. These residues were selected using the protocol outlined by Adair et al. (1991) (Humanised antibodies. WO91/09967). Alignments of the rat antibody (donor) V-region sequences with the human germline (acceptor) V-region sequences are shown in FIG. 1, together with the designed humanised sequences. (FIG. 1(A) light chain graft 650 and FIG. 1(B) heavy chain graft 650). The CDRs grafted from the donor to the acceptor sequence are as defined by Kabat (Kabat et al., 1987), with the exception of CDR-H1 where the combined Chothia/Kabat definition is used (see Adair et al., 1991 Humanised antibodies. WO91/09967).

Genes encoding initial V-region sequences were designed and constructed by an automated synthesis approach by Entelechon GmbH, and modified to generate the grafted versions gL8 and gH9 by oligonucleotide directed mutagenesis. The gL8 sequence was sub-cloned into the UCB Celltech human light chain expression vector pVhCK, which contains DNA encoding the human C-Kappa constant region (Km3 allotype). The gH9 sequence was sub-cloned into pVhg1 Fab, which contains DNA encoding human heavy chain gamma-1 $CH_1$ constant region.

Human V-region IGKV1-39 plus JK2 J-region (International Immunogenetics Information System@IMGT, http://www.imqt.orq) was chosen as the acceptor for antibody 650 light chain CDRs. The light chain framework residues in graft gL8 are all from the human germline gene, with the exception of residues 58 and 71 (numbering according to Kabat), where the donor residues Isoleucine (I58) and Tysrosine (Y71) were retained, respectively. Retention of residues I58 and Y71 was essential for full potency of the humanised antibody.

Human V-region IGHV1-69 plus JH4 J-region (IMGT, http://www.imqt.orq) was chosen as the acceptor for the heavy chain CDRs of antibody 650. The heavy chain framework residues in grafts gH9 are all from the human germline gene, with the exception of residues 67, 69 and 71 (numbering according to Kabat), where the donor residues Alanine (A67), Phenylalanine (F69) and Valine (V71) were retained, respectively. Retention of residues A67, F69 and V71 was essential for full potency of the humanised antibody. The Glutamine residue at position 1 of the human framework was replaced with Glutamic acid (E1) to afford the expression and purification of a homogeneous product: the conversion of Glutamine to pyroGlutamate at the N-terminus of antibodies and antibody fragments is widely reported. The final selected variable graft sequences gL8 and gH9 are shown in FIG. 1(A) and FIG. 1(B) respectively.

The amino acid and DNA sequences encoding the CDRs, heavy and light variable regions, scFv and dsscFV formats of antibody 650 are shown in FIG. 2.

Example 3. Generation of Anti-IL-17AF Antibody 496.q3

The production of the antibody CA028_00496.g3 (also referred to herein as antibody 496.g3) against human IL-17A and human IL-17F has been previously described in WO2012/095662. The antibody binds human IL-17A, IL-17F and IL-17A/F heterodimer with pM affinity. The amino acid and DNA sequences encoding the CDRs, heavy and light variable regions and light chain and heavy chain of the Fab format of antibody 496.g3 are shown in FIG. 2. The 496.g3 (IL-17A/F binding) Fab constant regions comprised the human C-kappa constant region (K1m3 allotype) and the human gamma-1 $CH_1$ constant region and hinge (G1m17 allotype).

Example 4. Generation of Anti-Human Albumin Antibody 645

The production of the anti-human albumin antibody 645 has been previously described in WO2013/068571. The amino acid and DNA sequences encoding the CDRs, heavy and light variable regions, scFv and dsscFV formats of antibody 645 are shown in FIG. 2.

Example 5. Multi-Specific Antibody IL-13/IL-17AF—Construction of Transient Plasmids and Expression in Cells Multi-specific antibodies were designed with the anti-IL-17AF V-region (496.g3) fixed in the Fab position; the anti-albumin V-region (645 gL4gH5) and IL-13 (1539 gL8gH9) were reformatted into disulfide-linked scFv in the HL orientation (dsHL) and linked to the C-termini of the respective heavy and light chain constant regions of the Fab via a 11-amino acid glycine-serine rich linkers. (FIG. 7). The amino acid and DNA sequences encoding the full-length heavy chain and light chain of the multi-specific antibody are shown in FIG. 2.

The light chain and heavy chain genes were independently cloned into mammalian expression vectors for transient expression under the control of a hCMV promoter. Equal ratios of both plasmids were transfected into the CHO-S XE cell line (UCB) using the commercial ExpiCHO expifectamine transient expression kit (Thermo Scientific). The cultures were incubated in Corning roller bottles with vented caps at 37° C., 8.0% $CO_2$, 190 rpm. After 18-22 h, the cultures were fed with the appropriate volumes of CHO enhancer and feeds for the HiTiter method as provided by the manufacturer. Cultures were reincubated at 32° C., 8.0% $CO_2$, 190 rpm for an additional 10 to 12 days. The supernatant was harvested by centrifugation at 4000 rpm for 1 h at 4° C. prior to filter-sterilization through a 0.45 μm followed by a 0.2 μm filter. Expression titres were quantified by Protein G HPLC using a 1 ml GE HiTrap Protein G column (GE Healthcare) and Fab standards produced in-house. The expression titre is shown in Table 1.

TABLE 1

Expression titres from transient expression in CHO S -XE cell line

| Antibody | Concentration. (mg/L) |
|---|---|
| IL-17AF-IL-13 multi- specific antibody | 160 |

Example 6. IL-13/IL-17AF Multi-Specific Antibody—Mammalian Cell Line Development To demonstrate stable expression of IL-13/IL-17AF multi-specific antibody a stably expressing mammalian cell line was created. A CHO cell line was transfected with a vector containing 496.g3 Fab, 1539gH9gL8 dsscFv HL (LC, INS0025609), 645gH5gL4 dsscFv HL (HC, INS0025306) and a selectable marker. The cell lines were cloned and evaluated for fit to a suitable manufacturing process. To assess the quality and quantity of the protein and to ensure the optimal cell line was selected, the cell line was evaluated in a small scale model of a manufacturing fed-batch biore-actor. A CHO cell line was selected expressing IL-13/IL-17AF multi-specific antibody at greater than 1.8 g/L and greater than 75% monomer.

Example 7. Purification Process for IL-13/IL-17AF Multi-Specific Antibody

The multi-specific antibody protein was purified by native protein A capture step followed by a preparative size exclusion polishing step. Clarified supernatants from standard transient CHO expression were loaded onto a MabSelect (GE Healthcare) column giving a 5 min contact time and washed with binding buffer (20 mM Hepes pH7.4+150 mM NaCl). Bound material was eluted with a 0.1M sodium citrate pH3.1 step elution and neutralised with 2M Tris/HCl pH8.5 and quantified by absorbance at 280 nm.

Size exclusion chromatography (SE-UPLC) was used to determine the purity status of the eluted product. The antibody (~2 µg) was loaded on to a BEH200, 200 Å, 1.7 µm, 4.6 mm ID×300 mm column (Waters ACQUITY) and developed with an isocratic gradient of 0.2 M phosphate pH 7 at 0.35 mL/min. Continuous detection was by absorbance at 280 nm and multi-channel fluorescence (FLR) detector (Waters). The eluted multi-specific antibody was found to be 72% monomer.

The neutralised samples were concentrated using Amicon Ultra-15 concentrator (10 kDa molecular weight cut off membrane) and centrifugation at 4000×g in a swing out rotor. Concentrated samples were applied to a XK16/60 Superdex200 column (GE Healthcare) equilibrated in PBS, pH7.4 and developed with an isocratic gradient of PBS, pH7.4 at 1 ml/min. Fractions were collected and analysed by size exclusion chromatography on a BEH200, 200 Å, 1.7 µm, 4.6 mm ID×300 mm column (Aquity) and developed with an isocratic gradient of 0.2 M phosphate pH 7 at 0.35 mL/min, with detection by absorbance at 280 nm and multi-channel fluorescence (FLR) detector (Waters). Selected monomer fractions were pooled, 0.22 µm sterile filtered and final samples were assayed for concentration by A280 Scanning on DropSense96 (Trinean). Endotoxin level was less than 1.0EU/mg as assessed by Charles River's EndoSafe® Portable Test System with Limulus Amebocyte Lysate (LAL) test cartridges.

Monomer status of the final multi-specific antibody was determined by size exclusion chromatography on a BEH200, 200 Å, 1.7 µm, 4.6 mm ID×300 mm column (Aquity) and developed with an isocratic gradient of 0.2 M phosphate pH 7 at 0.35 mL/min, with detection by absorbance at 280 nm and multi-channel fluorescence (FLR) detector (Waters). The final multi-specific antibody was found to be >99% monomeric as shown in FIG. 3(A).

For analysis by sodium dodecyl sulphate-polyacrylamide gel electrophoresis (SDS-PAGE) samples were prepared by adding 4×Novex NuPAGE LDS sample buffer (Life Technologies) and either 10× NuPAGE sample reducing agent (Life Technologies) or 100 mM N-ethylmaleimide (Sigma-Aldrich) to ~5 µg purified protein, and were heated to 100° C. for 3 min. The samples were loaded onto a 10 well Novex 4-20% Tris-glycine 1.0 mm SDS-polyacrylamide gel (Life Technologies) and separated at a constant voltage of 225 V for 40 min in Tris-glycine SDS running buffer (Life Technologies). Novex Mark12 wide-range protein standards (Life Technologies) were used as standards. The gel was stained with Coomassie Quick Stain (Generon) and destained in distilled water.

On non-reducing SDS-PAGE the multi-specific antibody, theoretical molecular weight (MW) of ~100 kDa, migrated to ~120 kDa. When the multi-specific antibody protein was reduced, both chains migrated at a mobility rate approaching their respective theoretical MWs, heavy chain (HC)~52 kDa and light chain (LC)~51 kDa. Additional bands on the non-reduced gel at ~45-50 kDa are 'free' LC and HC missing the disulphide bond in the Fab portion of the molecule, they do not migrate to the same position as the LC and HC in lane 2 as they are not fully reduced. (FIG. 3(B)).

Example 8. Antigen Binding of IL-13/IL-17AF Multi-Specific Antibody Molecule (i) Antigen Binding Affinity The binding kinetics of human and cynomolgus IL-13, IL-17A, AF, F and albumin were assessed by surface plasmon resonance (Biacore T200).

A goat anti-human IgG, F(ab')$_2$ fragment specific antibody (Jackson ImmunoResearch) was immobilised on a CM5 Sensor Chip via amine coupling chemistry to a level of approximately 5000RU. Each analysis cycle consisted of capture of the IL-13/IL-17AF/albumin multi-specific antibody molecule to the anti F(ab')$_2$ surface, injection of analyte (at 25° C. at a flow rate of 30 µl per minute) followed by surface regeneration. Human and cynomolgus analytes were injected at 2-fold serial dilutions in HBS-EP+ running buffer (GE Healthcare) at concentrations of 10 nM to 0.3125 nM for IL-13, 5 nM to 0.156 nM for IL-17A, AF, F and 100 nM to 3.125 nM for albumin. Antigens were prepared in-house, with the exception of human IL-13 (R&D Systems), cyno IL-13 (Sinobiologicals) and human serum albumin (Jackson ImmunoResearch). Buffer blank injections were included to subtract instrument noise and drift.

Kinetic parameters were determined using a 1:1 binding model using Biacore T200 Evaluation software (version 3.0) and summarised in Tables 2(1) and 2(2). Where dissociation rates ($k_d$) were measured as less than $1.0×10^{-5}$ they were fixed to $1.0×10^{-5}$ (the limit of detection of the Biacore T200 instrument as defined by the manufacturer GE Healthcare) to calculate affinity ($K_D$).

The results demonstrated that the multi-specific antibody bound effectively to human and cynomolgus IL-17A, IL-17AF, IL-17F, IL-13 and albumin.

TABLE 2(1)

| Kinetic Constants of the IL-13/IL-17AF multi-specific antibody binding to human antigens. | | | | |
|---|---|---|---|---|
| Analyte | $k_a$ (1/Ms) | $k_d$ (1/s) | $K_D$ (pM) | n= |
| Human IL-17A | 2.26E+06 | 1.57E−05 | 9 | 7 |
| Human IL-17AF | 3.70E+06 | 4.54E−05 | 15 | 4 |
| Human IL-17F | 1.67E+06 | 1.98E−04 | 128 | 7 |
| Human IL-13 | 1.46E+06 | 3.84E−05 | 26 | 3 |
| Human albumin | 6.65E+04 | 1.54E−04 | 2508 | 3 |

Results represent the mean from the indicated number of determinations.

TABLE 2(2)

| Kinetic Constants of the IL-13/IL-17AF multi-specific antibody binding to cynomolgus antigens. | | | | |
|---|---|---|---|---|
| Analyte | $k_a$ (1/Ms) | $k_d$ (1/s) | $K_D$ (pM) | n= |
| Cyno IL-17A | 1.65E+06 | 1.24E−05 | 7 | 4 |
| Cyno IL-17AF | 2.25E+06 | 2.87E−05 | 14 | 4 |
| Cyno IL-17F | 1.14E+06 | 2.82E−04 | 283 | 4 |
| Cyno IL-13 | 9.48E+05 | 1.48E−04 | 156 | 3 |
| Cyno albumin | 8.18E+04 | 2.04E−04 | 2473 | 3 |

Results represent the mean from the indicated number of determinations.

(ii) Simultaneous Antigen Binding

Surface plasmon resonance was used to demonstrate that IL-17A, IL-13 and albumin can bind simultaneously to IL-13/IL-17AF multi-specific antibody using either human or cynomolgus forms of the proteins.

The method format for assessing simultaneous binding of analytes to IL-13/IL-17AF multi-specific antibody was to capture the antibody sample to an immobilized anti-human IgG F(ab')2 fragment specific antibody. Human or cynomolgus IL-13, IL-17A, and albumin were then injected singly or in a mixed solution of all three analytes (at 30 μl/min for 300 s) over the captured IL-13/IL-17AF multi-specific antibody (final concentrations of 30 nM IL-13, 15 nM IL-17A, 150 nM albumin).

At the end of each cycle the surface was regenerated at a flowrate of 10 μl/min using a 60 s injection of 50 mM HCl followed by a 30 s injection of 5 mM NaOH and a final 60 s injection of 50 mM HCl.

The binding response of each antigen when injected singly was determined, and the sum of the individual responses was compared to the binding response when a mixture of all three antigens was injected.

The mean binding response of a mixture of human IL-17A, IL-13 and albumin to IL-13/IL-17AF multi-specific antibody was 100% of the sum of the individual binding response (summarised in Table 3), indicating that IL-13/IL-17AF multi-specific antibody was able to simultaneously and independently bind each antigen.

TABLE 3

| Simultaneous Binding of IL-13/IL-17AF multi-specific antibody to Human IL-17A, IL-13 and Albumin | | | | |
|---|---|---|---|---|
| Analyte | Binding, n = 1 (RU) | Binding, n = 2 (RU) | Binding, n = 3 (RU) | Mean |
| IL-13 | 12 | 19 | 19 | |
| IL-17A | 33 | 53 | 51 | |

TABLE 3-continued

| Simultaneous Binding of IL-13/IL-17AF multi-specific antibody to Human IL-17A, IL-13 and Albumin | | | | |
|---|---|---|---|---|
| Analyte | Binding, n = 1 (RU) | Binding, n = 2 (RU) | Binding, n = 3 (RU) | Mean |
| Albumin | 36 | 60 | 59 | |
| IL-13 + IL-17A + Albumin | 81 | 131 | 129 | |
| Sum of Individual Binding Responses | 81 | 131 | 129 | |
| Binding of Mixture as a Percentage of Individual Binding Responses (%) | 100 | 100 | 100 | 100 |

The mean binding response of a mixture of cynomolgus IL-17A, IL-13 and albumin to IL-13/IL-17AF multi-specific antibody was 97% of the sum of the individual binding response (summarised in Table 4), indicating that IL-13/IL-17AF multi-specific antibody was able to simultaneously and independently bind each antigen.

TABLE 4

| Simultaneous Binding of IL-13/IL-17AF multi-specific antibody to Cynomolgus IL-17A, IL-13 and Albumin | | | | |
|---|---|---|---|---|
| Analyte | Binding, n = 1 (RU) | Binding, n = 2 (RU) | Binding, n = 3 (RU) | Mean |
| IL-13 | 31 | 30 | 30 | |
| IL-17A | 57 | 56 | 60 | |
| Albumin | 63 | 61 | 60 | |
| IL-13 + IL-17A + Albumin | 146 | 141 | 145 | |
| Sum of Individual Binding Responses | 151 | 146 | 150 | |
| Binding of Mixture as a Percentage of Individual Binding Responses (%) | 97 | 96 | 97 | 97 |

Example 9. Neutralisation of IL-13 by IL-13/IL-17AF Multi-Specific Antibody

The activity of the IL-13/IL-17AF multi-specific antibody to neutralise IL-13 was assessed using HEK 293 Human IL4/IL-13 SEAP reporter cell line assay. SEAP secretion was measured upon activation of the STAT6 pathway to assess IL-13 responses.

HEK 293 Human IL4/IL-13 SEAP reporter cells (#hkb-il413) were obtained from Invivogen, San Diego. Culturing, freezing and maintenance of the cell line followed manufacturers protocol.

Recombinant human IL-13 was obtained from R&D Systems, Minneapolis, MN. (#213-ILB)

Cells were plated such that cells were approximately 80% confluent upon stimulation in 96 flat bottom wells.

Cells were treated in duplicate with antibodies pre-incubated with 250 pg/mL IL-13 for 30 mins at 37° C., 5% CO2, 100% humidity, before adding to the cells for 24 hrs.

After 24 hours 20 μL of supernatant was pipetted from the cell stimulation and added to 180 μL of Quanti-blue #rep-qbs (Invivogen, San Diego), in accordance with manufacturers instructions.

Assay was developed until there was a visible colour change gradient and absorbance was read using a spectrophotometer at 620 nm. IC50s were calculated by non-linear regression using Graphpad prism (San Diego, CA). FIG. 4 shows a representative graph of % inhibition of STAT6 signalling by IL-13/IL-17AF multi-specific antibody.

TABLE 5

| IC50 value for inhibition of STAT6 signalling by IL-13/IL-17AF multi-specific antibody. | | | | |
|---|---|---|---|---|
| pM | +/− SEM | ng/ml | +/− SEM | n= |
| 4.118 | 1.319 | 0.4118 | 0.1319 | 3 |

Example 10. Neutralizing Effect of IL-13/IL-17AF Multi-Specific Antibody on IL-6 Responses by Human Dermal Fibroblasts to Human and Cynomolgus IL-17A and IL-17F The purpose of this study was to determine the neutralizing capacity of IL-13/IL-17AF multi-specific antibody against human and cynomolgus IL-17A and IL-17F in a human primary cell system. A pro-inflammatory response is induced when IL-17 is present in combination with other cytokines such as TNF-α. This synergistic effect was therefore harnessed to produce an IL-6 release assay from primary normal neonate human dermal fibroblasts (nHDF) stimulated with IL-17 and TNF-α.

The ability of IL-13/IL-17AF multi-specific antibody to inhibit IL-17 induced IL-6 release from nHDFs was measured in this assay. Specifically, nHDFs were stimulated with human or cynomolgus IL-17A (50 pM) or IL-17F (25,000 pM) in combination with TNF-α (25 pM) in the presence of a titration of IL-13/IL-17AF multi-specific antibody (concentration range 5000 pM to 0.25 pM for IL-17A study; 500,000 pM to 25 pM for IL-17F study). The resultant IL-6 response was then measured using homogeneous time-resolved FRET (HTRF).

nHDF cells (Sigma #106-05n) were cultured in complete media (DMEM+10% FCS+2 mM L-glutamine) and maintained in a tissue culture flask using standard techniques. Cells were harvested from the tissue culture flask using TrypLE (Invitrogen #12605036). The TrypLE was neutralised using complete medium (45 ml) and the cells were centrifuged at 300×g for 3 minutes. The cells were re-suspended in complete media (3-5 ml), counted and adjusted to a concentration of $3.125 \times 10^4$ cells/mL before addition to the 384-well assay plate (Corning #3701) at 40 μl/well. The cells were incubated for three hours at 37° C./5% $CO_2$, to adhere to the plate. IL-13/IL-17AF multi-specific antibody was serially diluted in complete media in a 384-well dilution plate (Greiner #781281) to a final concentration range of 5000 pM to 0.25 pM for assessment against IL-17A, and 500,000 pM to 25 pM for assessment against IL-17F. Mixtures of TNF-α and IL-17 cytokine were prepared in complete media to final concentrations of TNF-α 25 pM with either human or cynomolgus IL-17A 50 pM or IL-17F 25,000 pM. 30 μl/well of these solutions were then added to a 384-well reagent plate (Greiner #781281). 10 μl from the IL-13/IL-17AF multi-specific antibody serial dilution plate was then transferred to the reagent plate containing 30 μl of the diluted cytokines. IL-13/IL-17AF multi-specific antibody was then incubated with the cytokine mixture for one hour at 37° C./5% $CO_2$. After the incubation, 10 μl was transferred from the reagent plate to the assay plate containing cells. The assay plate was then incubated for 18 hours±2 hours at 37° C./5% $CO_2$. After the incubation was complete, the Europium cryptate and Alexa 665 antibodies from the Cisbio IL-6 HTRF kit (Cisbio #62IL6PEB) were diluted in reconstitution buffer and mixed 1:1; as per the kit insert. Subsequently, 10 μl/well of this antibody mixture was added to a white low volume 384-well HTRF plate (Greiner #784075). Supernatant from the assay plate was then transferred to the HTRF plate at 10 μl/well. The HTRF plate was then incubated at room temperature for 2 hours with gentle shaking. The HTRF plates were then read on a Synergy Neo 2 plate reader as per the manufacturer's instructions, measuring the fluorescence at reads of 330/620 nm and 330/665 nm. The ratio values were then calculated using the following equation (330/665 nm divided by 330/620 nm)×10,000 and used to determine the relative percentage inhibition as compared to the control wells, using Microsoft Excel. 4PL curve fitting and calculation of ICSO values was performed using GraphPad Prism 7.0.

Results shown are the mean (+/−SEM) of three independent experiments. The IC50 value of IL-13/IL-17AF multi-specific antibody was calculated as 42pM for human IL-17A and 49pM for cynomolgus IL-17A. The IC50 value of IL-13/IL-17AF multi-specific antibody was calculated as 28,030 pM for human IL-17F and 34,320 pM for cynomolgus IL-17F. (FIG. 5).

TABLE 6

| Summary of potency, efficacy and hill slope values for IL-13/IL-17AF multi-specific antibody. Values were calculated from three independent experiments. | | | |
|---|---|---|---|
| Assay | IC50 (pM) | Emax (%) | Slope |
| Human IL-17A | 42 | 100 | 2 |
| Cynomolgus IL-17A | 49 | 100 | 2.4 |
| Human IL-17F | 28030 | 100 | 3.2 |
| Cynomolgus IL-17F | 34320 | 100 | 2.6 |

Example 11. Simultaneous Neutralisation of IL-13, IL-17A and IL-17F by IL-13/IL-17AF Multi-Specific Antibody in an NHEK CXCL1 Release Bioassay The purpose of this assay was to assess the ability of IL-13/IL-17AF multi-specific antibody to simultaneously neutralise IL-13, IL-17A and IL-17F in a primary cell system. When NHEK are treated with IL-13 or IL-17A or IL-17F individually, they induce the secretion of CXCL1, a chemokine which is responsible for recruiting cells to sites of inflammation. In the context of atopic dermatitis, there is evidence that CXCL1 has a role in sensitising neurons such that they have a lower excitation threshold. This observation may be pertinent to the itch that patients experience (Yang T. B. and Kim B. S. 2019; "Pruritus in allergy and immunology" J Allergy Clin Immunol 144(2): 353-360).

NHEK (PromoCell, Heidelberg), were stored, cultured and used as per the manufacturers protocol. Cells were plated such that they were 100% confluent upon stimulation in 48 flat bottom well plates. Cells were pre-incubated with increasing concentrations of anti-IL-13, anti-IL-17A, anti-IL-17F, or IL-13/IL-17AF multi-specific antibody respectively for 30 minutes before treatment with 100 ng/mL IL-13 and 100 ng/mL IL-17A, 1 μg/mL IL-17F for 72 hours. After the elapsed time period, 50 μl cell-free supernatant was collected for quantification of CXCL1 concentration via ELISA as per the manufacturers protocol (R&D Systems). $IC_{50}$ of each experimental group was calculated by non-linear regression using Graphpad prism (San Diego, CA).

The results demonstrated that the IL-13/IL-17AF multi-specific antibody simultaneously neutralised IL-13, IL-17A and IL-17F activity. (FIG. 6). When normalising for the number of binding sites available in the assay, IL-13/IL-17AF multi-specific antibody (81.3%) was more effective than anti-IL-17A (52.7%), anti-IL-17F (0.7%) or anti-IL-13 (48.8%) at inhibiting CXCL1 release. Increasing the concentration of anti-IL-17A, anti-IL-17F or anti-IL-13 alone did not improve the maximal inhibition achieved. The results highlight the benefit of simultaneously inhibiting IL-13, IL-17A and IL-17F compared to a single cytokine neutralisation.

Example 12. Comparison of Multi-Specific IL-13/IL-17 Antibody with IL-13/IL-17 Antibodies of the Prior Art

INTRODUCTION

An example of an IL-13/IL-17AF multi-specific antibody according to the present invention is shown in FIG. 7. It comprises a Fab domain with dual specificity for IL-17A and IL-17F, linked to 2 scFv domains, one specific for IL-13 and the other for albumin. The anti-albumin domain confers the multi-specific antibody with an extended half-life.

Bi-specific antibodies which bind to IL-13 and IL-17 have previously been described by Abbvie (WO2013/102042A2) and Genentech (WO2015/127405A2). However, little is disclosed about how they bind and to what degree they bind to IL-13, IL-17A and IL-17F. In order to compare these properties, we made the antibodies described in the prior art and investigated their binding behaviours for the following characteristics:

Affinity for IL-13
Interaction of molecule with IL-13 and IL-13Rα1
Affinity for IL-17A
Affinity for IL-17F Generation of Comparator Antibodies BITS7201A (Genentech) was constructed using the sequences described in Example 6 of WO2015/127405A2.

DVD2166 and DVD2174 (Abbvie) were constructed using the sequences described in WO2013/102042A2, Table 6 and Table 7. These molecules were selected based on the reported activity of the individual arms of the bi-specifics against IL-13 and IL-17 being near-equivalent or equivalent to their respective parent antibody (WO2013/102042A2 Example 4, page 83 para 0195).

DNA constructs were transfected into CHO-SXE cells using the high titre protocol of the ExpiCHO transfection system (ThermoFisher Scientific). Upon harvest, cell cultures were centrifuged for at least an hour at 4 000 RPM and the supernatants were clarified by filtration using 0.22 μM Stericup filter units.

DVD2166+DVD2174 Purification

DVD-IgG proteins were purified by applying clarified supernatants over a 10 ml MabSelect Sure column and washed with PBS, pH 7.4 for 3 column volumes (CVs).

Proteins were eluted off the column with 0.1 M NaCitrate pH 3.6 step elution and neutralised with 2 M Tris-HCl, pH 8.5. Monomeric proteins were isolated by application onto a HiLoad 16×60 Superdex 200 pg column (Sigma) equilibrated with PBS, pH 7.4. Fractions containing monomeric proteins were pooled, sterile filtered and stored at 4° C.

BITS7201A purification

Parental knob and hole proteins were purified by applying clarified supernatants over a 10 mL MabSelect Sure column and washed with 3 CVs PBS, pH 7.4. Proteins were eluted off the column with 0.1 M NaCitrate pH 3.6. In order to neutralise and stabilise the protein, the samples were diluted 1:1 with 1 M arginine/succinate buffer, pH 8.7. The parental antibodies were then applied onto a HiLoad 26×60 Superdex 200 pg column (Sigma) equilibrated with 0.15 M sodium acetate, 0.5 M Arginine buffer, pH 8.5. The bispecific material was subsequently generated by mixing parental antibodies at a 1:1 ratio in the presence of 5 mM cysteamine and incubating overnight at room temperature. A second preparative gel filtration step was performed to remove any high molecular weight species from the exchanged bispecific material by applying to a HiLoad 26×60 Superdex 200 pg column equilibrated with PBS, pH 7.4. Fractions containing monomeric bispecific proteins were pooled, sterile filtered and stored at 4° C.

Comparison of Binding Characteristics

The binding kinetics of human IL-13, IL-17A, and IL-17F binding to IL-13/IL-17AF multi-specific antibody, termed "UCBXXXX", and prior art antibodies were assessed by surface plasmon resonance (Biacore T200) and directly compared within a single experiment. In addition, surface plasmon resonance was used to assess whether the binding of IL-13/IL-17AF multi-specific antibody UCBXXXX or comparator molecules to IL-13 resulted in blocking of the IL-13 interaction with IL-13 receptors.

A goat anti-human IgG, F(ab')$_2$ fragment specific antibody (Jackson ImmunoResearch) was immobilised on a CM5 Sensor Chip via amine coupling chemistry to a level of approximately 5000RU. For affinity assessment, each analysis cycle consisted of capture of IL-13/IL-17AF multi-specific antibody or comparator bispecific molecule to the anti F(ab')$_2$ surface (50 to 100RU), injection of analyte (at 25° C. at a flow rate of 30 μl per minute for 180s), after which dissociation was monitored for 1200 s for IL-13 and IL-17A, and 600s for IL-17F. At the end of each cycle the surface was regenerated at a flowrate of 10 μl/min using a 60s injection of 50 mM HCl followed by a 30s injection of 5 mM NaOH and a final 60s injection of 50 mM HCl. Analytes were injected at 2-fold serial dilutions in HBS-EP+ running buffer (GE Healthcare) at concentrations of 10 nM to 0.3125 nM for IL-13 and 5 nM to 0.156 nM for IL-17A and IL-17F. IL-17A and IL-17F were prepared in-house whereas human IL-13 was sourced from R&D Systems. Buffer blank injections were included to subtract instrument noise and drift.

Kinetic parameters were determined using a 1:1 binding model using Biacore T200 Evaluation software (version 3.0). The results are summarised in Table 7.

TABLE 7

Comparison of kinetic constants for binding to IL-13, IL-17A and IL-17F.

| Molecule | Analyte | $k_a$ (1/Ms) | $k_d$ (1/s) | $K_D$ (pM) |
|---|---|---|---|---|
| UCBXXXX* | IL-13 | 3.61E+06 | 1.11E−04 | 25.8 |
| BITS7210A* | | 2.05E+06 | 5.69E−05 | 27.5 |
| DVD2166 | | 8.16E+05 | 1.50E−05 | 18.35 |
| DVD2174 | | 6.50E+05 | 3.66E−05 | 56.34 |
| UCBXXXX* | IL-17A | 3.20E+06 | 3.45E−05 | 8.2 |
| BITS7210A* | | 1.27E+07 | 1.06E−03 | 84.4 |
| DVD2166 | | 5.59E+05 | 7.68E−05 | 137.4 |

TABLE 7-continued

| Comparison of kinetic constants for binding to IL-13, IL-17A and IL-17F. | | | | |
|---|---|---|---|---|
| Molecule | Analyte | $k_a$ (1/Ms) | $k_d$ (1/s) | $K_D$ (pM) |
| DVD2174 | | 4.76E+05 | 1.28E−04 | 268.4 |
| UCBXXXX* | IL-17F | 2.66E+06 | 2.19E−04 | 82.1 |
| BITS7210A* | | 7.71E+06 | 5.74E−04 | 74.4 |
| DVD2166 | | ←←←←←←←←←No Binding→→→→→→→→→ | | |
| DVD2174 | | ←←←←←←←←←No Binding→→→→→→→→→ | | |

*Results represent the mean from two technical replicates within the same experiment To assess IL-13Rα1 receptor blocking, each antibody molecule was captured to the goat anti-human IgG, F(ab')₂ surface (to approximately 50 to 100RU), followed by injection of IL-13 (25 nM for 180s at 10 µl/min) and injection of IL-13Rα1 (R&D Systems, 100 nM for 300s at 10 µl/min). Blank injections of both IL-13 and IL-13Rα1 were included to subtract any drift or background responses. As summarised in Table 8, UCBXXXX was able to block the interaction of IL-13 with IL-13Rα1, whereas BITS7210A, DVD2166 and DVD 2174 molecules were not.

TABLE 8

| IL-13Rα1 receptor blocking by IL-13/IL-17AF multi-specific antibody and comparator molecules. | | | | |
|---|---|---|---|---|
| Molecule | Capture (RU) | IL-13 Binding (RU) | IL-13Rα1 Binding (RU) | IL-13Rα1 Blocker |
| UCBXXXX | 65.4 | 7.3 | 0.2 | Yes |
| BITS7210A | 86 | 8.6 | 15.7 | No |
| DVD2166 | 115.2 | 11.7 | 13.8 | No |
| DVD2174 | 115.3 | 11.3 | 16.2 | No |

A further experiment was conducted to assess the ability of IL-13/IL-17AF multi-specific antibody to block binding to IL-13Rα1 and IL-13Rα2. In this experiment approximately 260RU of UCBXXXX was captured to an immobilised mouse anti human CH₁ antibody (UCB in-house), followed by injection of IL-13 (25 nM for 180s at 10 µl/min) then either IL-13Rα1 or IL-13Rα2 (R&D Systems, 100 nM for 300s at 10 µl/min). Blank injections of IL-13, IL-13Rα1 and IL-13Rα2 were included to subtract any drift or background responses. The results demonstrated that UCBXXXX was able to block the interaction of IL-13 with both IL-13Rα1 and IL-13Rα2. (Table 9).

TABLE 9

| IL-13Rα1 and IL-13Rα2 receptor blocking by IL-13/IL-17AF multi-specific antibody. | | | |
|---|---|---|---|
| Capture (RU) | IL-13 Binding (RU) | IL-13Rα1 Binding (RU) | IL-13Rα2 Binding (RU) |
| 264.4 | 27.0 | 0.8 | 0.3 |

DISCUSSION

The comparator study demonstrated that IL-13/IL-17AF multi-specific antibody UCBXXXX, bispecific antibody BITS7210A, and dual-variable-domain antibodies DVD2166 and DVD2174 were able to bind with high affinity to IL-13. However, the characteristics of the binding interactions were very different. UCBXXXX was able to block the interaction of IL-13 with IL-13-Rα1, whereas BITS7210A, DVD2166 and DVD2174 were not.

The comparator study further demonstrated that multi-specific antibody UCBXXXX, bispecific antibody BITS7210A, and dual-variable-domain antibodies DVD2166 and DVD2174 were able to bind to IL-17. Again however, the characteristics of the binding interactions were very different. The binding affinity of UCBXXXX for IL-17A was significantly higher than that of BITS7210A and the DVD antibodies. UCBXXXX and BITS7210A bound with similar affinity to IL-17F whereas the DVD antibodies were not able to bind to IL-17F at all.

The interaction between IL-13 and IL-13Rα1, in the presence of these antibodies, is important in the context of reducing potential immunogenicity. Evidence suggests that immunogenicity, particularly the generation of anti-drug-antibodies (ADA), should be closely considered when investigating potential new bispecific antibody therapeutics. A major driver for ADA generation is the engagement and subsequent internalisation of the therapeutic antibody with target antigens expressed on the cell surface (Schellekens, H., 2002; Clin Ther. 24(11):1720-40). Internalised therapeutic antibody/target antigen complexes undergo trafficking through various intracellular compartments, and can either be recycled back to the cell surface or undergo degradation (St Pierre et al, 2011); which can lead to peptide presentation by antigen presenting molecules and ADA generation.

In bispecific antibody BITS7201A, the IL-13 F(ab) portion of the molecule is the same as the anti-IL-13 antibody, lebrikizumab (see example 6 of WO2015/127405A2). It is believed that lebrikizumab binds to IL-13 at a site which allows IL-13 to bind to its receptors IL-13Rα1 and IL-13Rα2, but blocks the interaction with IL-4Ra receptor (Popovic et al., 2017; J Mol Biol. 429(2):208-19). This particular type of interaction may enable internalisation of the antibody/target antigen/receptor complex through IL-13Rα2 and thus increase the potential for an immunogenic response. In a phase I clinical trial, BITS7201A was associated with a high incidence of anti-drug antibodies (ADAs) and was withdrawn from clinical development.

Similarly, the dual-variable-domain antibodies DVD2166 and DVD2174 were not able to block the interaction of IL-13 with IL-13-Rα1.

To mitigate the potential immunogenicity risk, UCBXXXX has been specifically designed so that, on engagement with its respective target antigens IL-13, IL-17A and IL-17F, they are prevented from interacting with receptors on cells, thus decreasing the chance of internalisation, degradation and potential for ADA generation. The incidence of ADA with UCBXXXX in humans will only be known for certain once clinical data are available.

The data generated above indicates that IL-13/IL-17AF multi-specific antibody UCBXXXX has the correct properties to become an effective IL-13/IL-17 antibody therapeutic, with improved efficacy and lower risk of immunogenicity.

The invention claimed is:

1. A multi-specific antibody which binds human IL-13, human IL-17A and/or human IL-17F, comprising an IL-13 binding site which comprises:
 a light chain variable region comprising the sequence given in SEQ ID NO:15 for CDR-L1, the sequence given in SEQ ID NO:16 for CDR-L2 and the sequence given in SEQ ID NO:17 for CDR-L3, and
 a heavy chain variable region comprising the sequence given in SEQ ID NO:18 for CDR-H1, the sequence given in SEQ ID NO:19 for CDR-H2 and the sequence given in SEQ ID NO:20 for CDR-H3.

2. A multi-specific antibody according to claim 1, wherein the IL-13 binding site comprises a light chain variable region comprising the sequence given in SEQ ID NO:27 and a heavy chain variable region comprising the sequence given in SEQ ID NO:28.

3. A multi-specific antibody according to claim 1, wherein the IL-13 binding site comprises a light chain variable region comprising the sequence given in SEQ ID NO:31 and a heavy chain variable region comprising the sequence given in SEQ ID NO:32.

4. A multi-specific antibody according to claim 1, comprising an antigen binding site that binds to human IL-17A and human IL-17F which comprises:
 a light chain variable region comprising the sequence given in SEQ ID NO:1 for CDR-L1, the sequence given in SEQ ID NO:2 for CDR-L2 and the sequence given in SEQ ID NO:3 for CDR-L3, and
 a heavy chain variable region comprising the sequence given in SEQ ID NO:4 for CDR-H1, the sequence given in SEQ ID NO:5 for CDR-H2 and the sequence given in SEQ ID NO:6 for CDR-H3.

5. A multi-specific antibody according to claim 4, wherein the antigen binding site that binds to human IL-17A and human IL-17F comprises a light chain variable region comprising the sequence given in SEQ ID NO:7 and a heavy chain variable region comprising the sequence given in SEQ ID NO:9.

6. A multi-specific antibody according claim 1 which binds human IL-13, human IL-17A and/or human IL-17F, comprising:
 a) a polypeptide chain of formula (Ia):

$$V_H\text{-}CH_1\text{-}X\text{-}V_1;\text{ and}$$

b) a polypeptide chain of formula (IIa):

$$V_L\text{-}C_L\text{-}Y\text{-}V_2;$$

wherein:
 $V_H$ represents a heavy chain variable domain;
 $CH_1$ represents domain 1 of a heavy chain constant region;
 X represents a bond or linker;
 Y represents a bond or linker;
 $V_1$ represents a scFv, a dsscFv, or a dsFv;
 $V_L$ represents a light chain variable domain;
 $C_L$ represents a domain from a light chain constant region, such as Ckappa;
 $V_2$ represents a scFv, a dsscFv or a dsFv;
 wherein the polypeptide chain of formula (Ia) comprises a protein A binding domain; and
 wherein the polypeptide chain of formula (IIa) does not bind protein A.

7. A multi-specific antibody according to claim 6, wherein:
 $V_L$ and $V_H$ comprise an antigen binding site that binds to human IL-17A and human IL-17F, $V_2$ comprises an antigen binding site that binds to human IL-13, and $V_1$ comprises an antigen binding site that binds to human serum albumin;

wherein $V_L$ comprises the sequence given in SEQ ID NO:1 for CDR-L1, the sequence given in SEQ ID NO:2 for CDR-L2 and the sequence given in SEQ ID NO:3 for CDR-L3, and $V_H$ comprises the sequence given in SEQ ID NO:4 for CDR-H1, the sequence given in SEQ ID NO:5 for CDR-H2 and the sequence given in SEQ ID NO:6 for CDR-H3;

wherein $V_1$ comprises a light chain variable region comprising the sequence given in SEQ ID NO:39 for CDR-L1, the sequence given in SEQ ID NO:40 for CDR-L2 and the sequence given in SEQ ID NO:41 for CDR-L3; and a heavy chain variable region comprising the sequence given in SEQ ID NO:42 for CDR-H1, the sequence given in SEQ ID NO:43 for CDR-H2 and the sequence given in SEQ ID NO:44 for CDR-H3; and wherein $V_2$ comprises a light chain variable region comprising the sequence given in SEQ ID NO:15 for CDR-L1, the sequence given in SEQ ID NO:16 for CDR-L2 and the sequence given in SEQ ID NO:17 for CDR-L3, and a heavy chain variable region comprising the sequence given in SEQ ID NO:18 for CDR-H1, the sequence given in SEQ ID NO:19 for CDR-H2 and the sequence given in SEQ ID NO:20 for CDR-H3.

8. A multi-specific antibody according to claim 6, wherein $V_L$ comprises the sequence given in SEQ ID NO:7 and $V_H$ comprises the sequence given in SEQ ID NO:9.

9. A multi-specific antibody according to claim 6, wherein $V_2$ comprises a light chain variable region comprising the sequence given in SEQ ID NO:27 and a heavy chain variable region comprising the sequence given in SEQ ID NO:28.

10. A multi-specific antibody according to claim 6, wherein $V_2$ comprises a light chain variable region comprising the sequence given in SEQ ID NO:31 and a heavy chain variable region comprising the sequence given in SEQ ID NO:32.

11. A multi-specific antibody according to claim 6, wherein $V_1$ comprises a light chain variable region comprising the sequence given in SEQ ID NO:45 and a heavy chain variable region comprising the sequence given in SEQ ID NO:46.

12. A multi-specific antibody according to claim 6, wherein $V_1$ comprises a light chain variable region comprising the sequence given in SEQ ID NO:49 and a heavy chain variable region comprising the sequence given in SEQ ID NO:50.

13. A multi-specific antibody according to claim 6, wherein the light chain variable region and heavy chain variable region of $V_2$ are connected by a linker, said linker comprising the sequence given in SEQ ID NO:66.

14. A multi-specific antibody according to claim 13, wherein $V_2$ is a scFv comprising the sequence given in SEQ ID NO:35 or a dsscFv comprising the sequence given in SEQ ID NO:37.

15. A multi-specific antibody according to claim 6, wherein the light chain variable region and heavy chain variable region of $V_1$ are connected by a linker, said linker comprising the sequence given in SEQ ID NO:68.

16. A multi-specific antibody according to claim 15, wherein $V_1$ is a scFv comprising the sequence given in SEQ ID NO:53 or a dsscFv comprising the sequence given in SEQ ID NO:55.

17. A multi-specific antibody according to claim 6, wherein Y is a linker comprising the sequence given in SEQ ID NO:65.

18. A multi-specific antibody according claim 6, wherein X is a linker comprising the sequence given in SEQ ID NO:67.

19. A multi-specific antibody according to claim 1, comprising the sequence given in SEQ ID NO:57 or SEQ ID NO: 59.

20. A multi-specific antibody according to claim 1, comprising the sequence given in SEQ ID NO:61 or SEQ ID NO: 63.

21. A multi-specific antibody according to claim 1, comprising the sequence given in SEQ ID NO:59 and the sequence given in SEQ ID NO: 63.

22. An isolated polynucleotide encoding a multi-specific antibody as defined in claim 1.

23. An expression vector carrying the polynucleotide of claim 22.

24. A host cell comprising the vector as defined in claim 23.

25. A method of producing a multi-specific antibody, comprising culturing the host cell of claim 24 under conditions permitting production of the antibody, and recovering the antibody produced.

26. The method of claim 25 comprising a protein A purification step.

27. A pharmaceutical composition comprising an antibody as defined in claim 1 and a pharmaceutically acceptable adjuvant and/or carrier.

28. A method of treating atopic dermatitis, chronic hand eczema, nasal micropolyposis or polyposis, food allergy, or eosinophilic esophagitis, comprising administering a therapeutically effective amount of a multi-specific antibody according to claim 1 to a patient in need thereof.

* * * * *